(12) United States Patent
Loushin et al.

(10) Patent No.: US 12,023,224 B2
(45) Date of Patent: Jul. 2, 2024

(54) INSERTION SYSTEM FOR DEPLOYING A VENTILATION DEVICE

(71) Applicant: Preceptis Medical, Inc., Maple Grove, MN (US)

(72) Inventors: Michael K. H. Loushin, Shoreview, MN (US); Keith J. Leland, Medina, MN (US)

(73) Assignee: Preceptis Medical, Inc., Maple Grove, MN (US)

( * ) Notice: Subject to any disclaimer, the term of this patent is extended or adjusted under 35 U.S.C. 154(b) by 789 days.

(21) Appl. No.: 16/884,651

(22) Filed: May 27, 2020

(65) Prior Publication Data

US 2020/0281772 A1 Sep. 10, 2020

Related U.S. Application Data

(60) Continuation of application No. 15/094,085, filed on Apr. 8, 2016, now Pat. No. 10,695,224, which is a
(Continued)

(51) Int. Cl.
*A61F 11/20* (2022.01)

(52) U.S. Cl.
CPC .................. *A61F 11/202* (2022.01)

(58) Field of Classification Search
CPC ........... A61F 11/00–06; A61M 27/002; A61M 29/00; A61M 25/01; A61M 25/0662;
(Continued)

(56) References Cited

U.S. PATENT DOCUMENTS

| 3,530,860 A | 9/1970 | Majoros |
| 3,662,754 A | 5/1972 | Halloran |

(Continued)

FOREIGN PATENT DOCUMENTS

| CN | 102014795 A | 4/2011 |
| GB | 2437708 A | 11/2007 |

(Continued)

OTHER PUBLICATIONS

Canadian Office Action dated Apr. 16, 2020 for corresponding application Serial No. 2,876,865.
(Continued)

*Primary Examiner* — Sarah W Aleman
*Assistant Examiner* — Mikail A Mannan
(74) *Attorney, Agent, or Firm* — Leanne Taveggia Farrell; Westman, Champlin & Koeher, P.A.

(57) ABSTRACT

An insertion system includes a handle assembly and a nose assembly removably attached to the handle assembly and including an insertion end. The handle assembly includes a main body, a nose interface and an actuating element. The nose assembly includes a nose, a positioning rod extending from the nose to a distal end, a cutting sheath surrounding a distal end of the positioning rod and including a cutting edge, an actuation member having a proximal end coupled to the actuating element when the nose assembly is attached to the handle assembly and a distal end attached to the cutting sheath, a ventilation tube positioned distal to the distal end of the positioning rod and proximal to the insertion end. The cutting sheath retracts from around the ventilation tube and along the positioning rod when the actuating element on the handle assembly is moved.

12 Claims, 27 Drawing Sheets

Related U.S. Application Data division of application No. 13/826,497, filed on Mar. 14, 2013, now Pat. No. 9,370,448.

(60) Provisional application No. 61/660,280, filed on Jun. 15, 2012.

(58) Field of Classification Search
CPC . A61M 2025/0681; A61B 2017/00787; A61B 17/34–3498; A61B 2017/3405–3492; A61B 2017/0046; A61B 2017/292; A61B 2017/2922; A61B 17/2841
See application file for complete search history.

(56) References Cited

U.S. PATENT DOCUMENTS

| | | |
|---|---|---|
| 3,807,409 A | 4/1974 | Paparella et al. |
| 3,871,380 A | 3/1975 | Heros |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 4,174,716 A | 11/1979 | Treace |
| 4,334,538 A | 6/1982 | Juhn |
| 4,445,517 A | 5/1984 | Feild |
| 4,468,218 A | 8/1984 | Armstrong |
| 4,473,073 A | 9/1984 | Darnell |
| 4,580,568 A | 4/1986 | Gianturco |
| 4,695,275 A | 9/1987 | Bruce et al. |
| 4,744,792 A | 5/1988 | Sander et al. |
| 4,964,850 A | 10/1990 | Bouton et al. |
| 5,026,378 A | 6/1991 | Goldsmith, III |
| 5,053,040 A | 10/1991 | Goldsmith, III |
| 5,073,166 A | 12/1991 | Parks et al. |
| 5,139,502 A | 8/1992 | Berg et al. |
| 5,178,623 A | 1/1993 | Cinberg et al. |
| 5,207,685 A | 5/1993 | Cinberg et al. |
| 5,254,120 A | 10/1993 | Cinberg et al. |
| 5,466,239 A | 11/1995 | Cinberg et al. |
| 5,484,434 A | 1/1996 | Cartmell et al. |
| 5,496,329 A | 3/1996 | Reisinger |
| 5,566,094 A | 10/1996 | Kojima et al. |
| 5,578,053 A | 11/1996 | Yoon |
| 5,643,280 A | 1/1997 | Del Rio et al. |
| 5,601,568 A | 2/1997 | Chevillon et al. |
| 5,645,584 A | 7/1997 | Suyama |
| 5,665,094 A | 9/1997 | Goldenberg |
| 5,693,065 A | 12/1997 | Rains, III |
| D389,915 S | 1/1998 | Emerson et al. |
| 5,709,677 A | 1/1998 | Slatkine |
| 5,711,309 A | 1/1998 | Goldenberg |
| 5,916,150 A | 6/1999 | Sillman |
| 5,976,151 A | 11/1999 | Siegbahn |
| 6,027,532 A | 2/2000 | Hobeika |
| 6,156,064 A | 12/2000 | Chouinard |
| D439,337 S | 3/2001 | Jones |
| 6,238,402 B1 | 5/2001 | Sullivan, III et al. |
| 6,245,077 B1 | 6/2001 | East et al. |
| 6,258,067 B1 | 7/2001 | Hill |
| 6,292,072 B1 | 9/2001 | King et al. |
| D453,833 S | 2/2002 | Hess |
| 6,361,526 B1 | 3/2002 | Reisdorf et al. |
| 6,379,323 B1 * | 4/2002 | Patterson .............. A61F 11/202 623/1.37 |
| 6,390,975 B1 | 5/2002 | Walls et al. |
| 6,406,453 B1 | 6/2002 | Goode et al. |
| 6,443,970 B1 | 9/2002 | Schulze et al. |
| 6,527,780 B1 | 3/2003 | Wallace et al. |
| 6,692,455 B2 | 2/2004 | Goode et al. |
| 6,695,861 B1 | 2/2004 | Rosenberg et al. |
| D490,152 S | 5/2004 | Myall et al. |
| 6,730,056 B1 | 5/2004 | Ghaem et al. |
| 6,770,080 B2 | 8/2004 | Kaplan et al. |
| 6,776,797 B1 | 8/2004 | Blom et al. |
| 6,936,023 B2 | 8/2005 | Goode et al. |
| 6,939,494 B2 | 9/2005 | Goode et al. |
| D521,641 S | 5/2006 | Reschke et al. |
| D538,936 S | 3/2007 | Bohmel et al. |
| 7,235,099 B1 | 6/2007 | Duncavage et al. |
| 7,410,480 B2 | 8/2008 | Muni et al. |
| 7,419,497 B2 | 9/2008 | Muni et al. |
| 7,704,259 B2 | 4/2010 | Kaplan et al. |
| D619,579 S | 7/2010 | Flores Rodrigues Vieira |
| 7,879,033 B2 | 2/2011 | Sartor et al. |
| 8,052,693 B2 | 11/2011 | Shahoian |
| D664,657 S | 7/2012 | Vieira et al. |
| D673,676 S | 1/2013 | Goudreau et al. |
| 8,864,774 B2 | 10/2014 | Liu et al. |
| 8,979,868 B2 | 3/2015 | Loushin et al. |
| 9,011,363 B2 | 4/2015 | Clopp et al. |
| 9,907,700 B2 | 3/2018 | Clopp et al. |
| 2002/0058899 A1 | 5/2002 | Goode et al. |
| 2003/0018291 A1 | 1/2003 | Hill et al. |
| 2005/0004520 A1 | 1/2005 | Lemoine et al. |
| 2005/0049675 A1 | 3/2005 | Wallace |
| 2005/0256450 A1 | 11/2005 | Palasis et al. |
| 2006/0025793 A1 | 2/2006 | Gibson et al. |
| 2008/0051804 A1 | 2/2008 | Cottler et al. |
| 2008/0097295 A1 | 4/2008 | Makower et al. |
| 2008/0234708 A1 | 9/2008 | Houser et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2009/0209972 A1 | 8/2009 | Loushin et al. |
| 2009/0299141 A1 | 12/2009 | Downey et al. |
| 2009/0299379 A1 | 12/2009 | Katz et al. |
| 2010/0174290 A1 | 7/2010 | Wuebbeling et al. |
| 2010/0256653 A1 | 10/2010 | Kaplan et al. |
| 2011/0015645 A1 | 1/2011 | Liu |
| 2011/0282190 A1 * | 11/2011 | Caffey .................. A61B 5/0066 600/427 |
| 2011/0288559 A1 | 11/2011 | Shahoian |
| 2012/0179187 A1 | 7/2012 | Loushin et al. |

FOREIGN PATENT DOCUMENTS

| | | |
|---|---|---|
| WO | 03057082 A1 | 7/2003 |
| WO | 2008131195 A2 | 10/2008 |
| WO | 2009105619 A3 | 8/2009 |
| WO | 2012094666 A1 | 7/2012 |

OTHER PUBLICATIONS

Prosecution history of corresponding U.S. Appl. No. 15/094,085 including: Notice of Allowance dated Feb. 27, 2020, Non-Final Office Action dated Jul. 11, 2019, Final Office Action dated Oct. 4, 2018 and Non-Final Office Action dated Feb. 8, 2018.

Prosecution history of corresponding U.S. Appl. No. 13/826,497 including: Notice of Allowance dated Jan. 8, 2016 and Non-Final Office Action dated Apr. 13, 2015.

U.S. Appl. No. 14/145,427, filed Oct. 3, 2013, entitled Stablization System and Aspiration Device with Rapid Diagnostics, 51 pages.

Australian Patent Examination Report No. 1 dated Jul. 18, 2013 for Australian Patent Application No. 2009215468, 4 pages.

Canadian Office Action dated Apr. 5, 2019 for Canadian Patent Application No. 2,876,865, 4 pages.

Canadian Office Action dated Nov. 12, 2019 for Canadian Patent Application No. 2,876,865, 5 pages.

Chinese First Office Action dated Dec. 4, 2012 for Chinese Patent Application No. 200980113954.0, 7 pages.

Chinese Second Office Action dated Jul. 22, 2013 for Chinese Patent Application No. 200980113954.0, 9 pages.

Chinese First Office Action dated Nov. 18, 2015 for Chinese Patent Application No. 201380031471.2, 14 pages.

Chinese Second Office Action dated Jul. 7, 2016 for Chinese Patent Application No. 201380031471.2, 13 pages.

European Communication dated Sep. 13, 2011 for European Patent Application No. 09713274.0, 1 page.

(56) References Cited

OTHER PUBLICATIONS

European Communication dated Aug. 25, 2011 for European Patent Application No. 09713274.0, 7 pages.
European Communication dated Apr. 29, 2015 for European Patent Application No. 13733138.5, 2 pages.
European Communication dated May 25, 2018 for European Patent Application No. 13733138.5, 4 pages.
Korean Official Action dated Jun. 20, 2019 for Korean Patent Application No. 10-2015-7000954, 5 pages.
PCT Search Report and Written Opinion dated Oct. 1, 2009 for PCT Application No. PCT/US2009/034648, 13 pages.
PCT Research Report and Written Opinion dated Apr. 25, 2012 for PCT Application No. PCT/US2012/020629, 13 pages.
PCT Research Report and Written Opinion dated Sep. 18, 2013 for PCT Application No. PCT/US2013/045082, 13 pages.
First Examination Report dated Jun. 26, 2020 for corresponding Indian application Serial No. 67/MUMNP/2015.
European Summons to attend oral proceedings pursuant to Rule 115(1) EPC dated Jul. 1, 2021, 6 pages.
European Communication dated Aug. 23, 2022 for corresponding European application Serial No. 13733138.5, 4 pages.
Office Action dated Aug. 19, 2022 for corresponding U.S. Appl. No. 16/830,803, 31 pages.
Office Action dated Mar. 16, 2023 for corresponding U.S. Appl. No. 16/830,803, 25 pages.
PCT Notification of Transmittal of the International Search Report and the Written Opinion of the International Searching Authority, or the Declaration and Search Report dated Sep. 18, 2023 for corresponding PCT application Serial No. PCT/US2023/018487, 7 pages.
PCT Written Opinion dated Sep. 18, 2023 for corresponding PCT application Serial No. PCT/US2023/018487, 7 pages.

\* cited by examiner

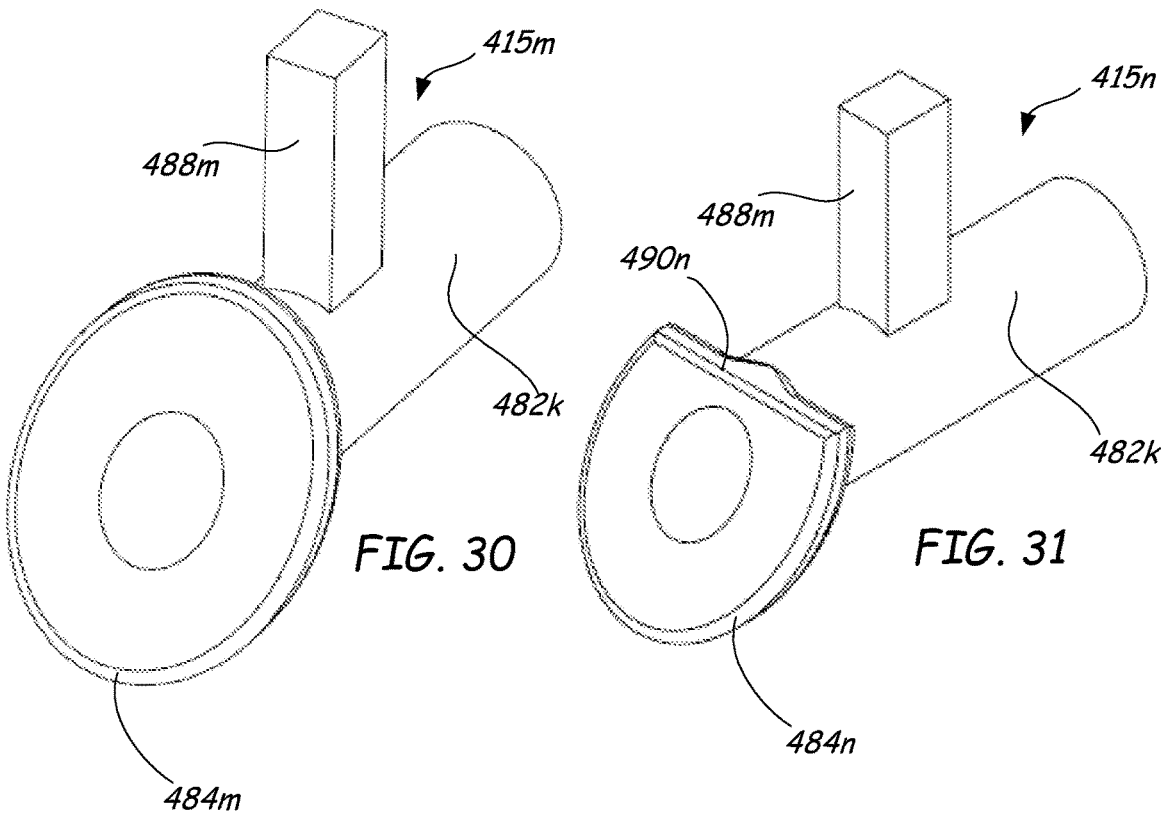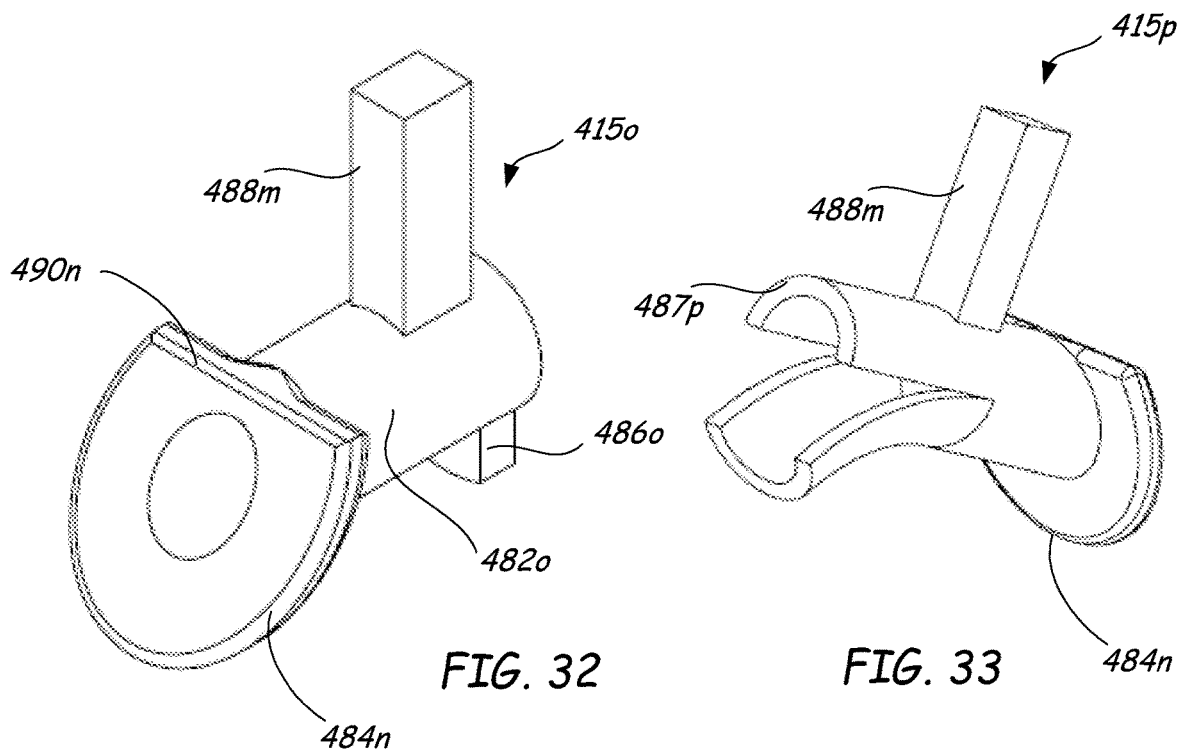

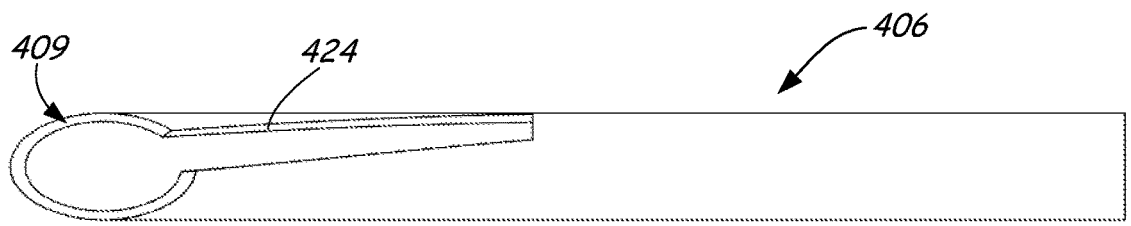
FIG. 57
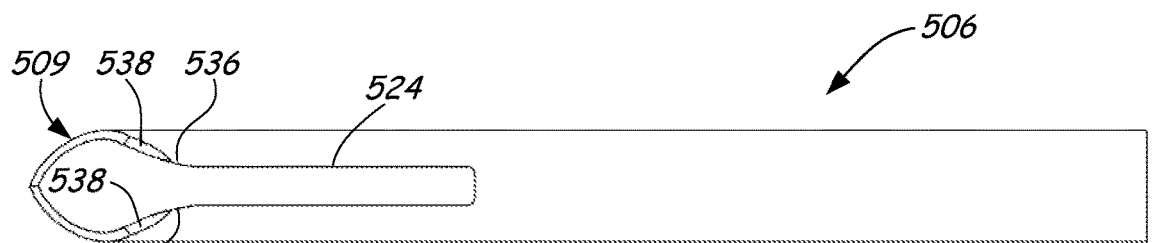
FIG. 58
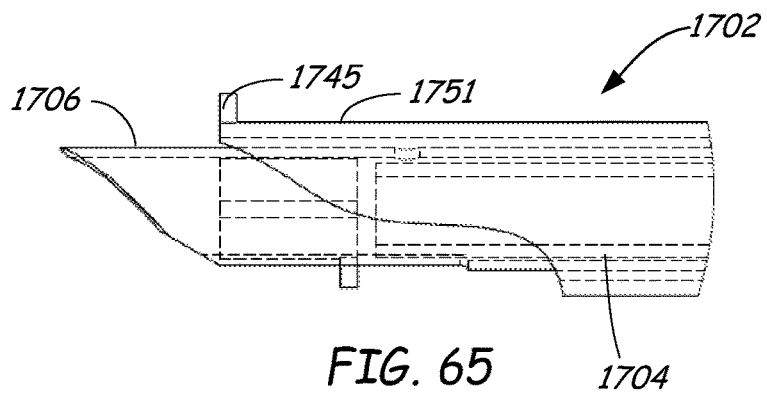
FIG. 65
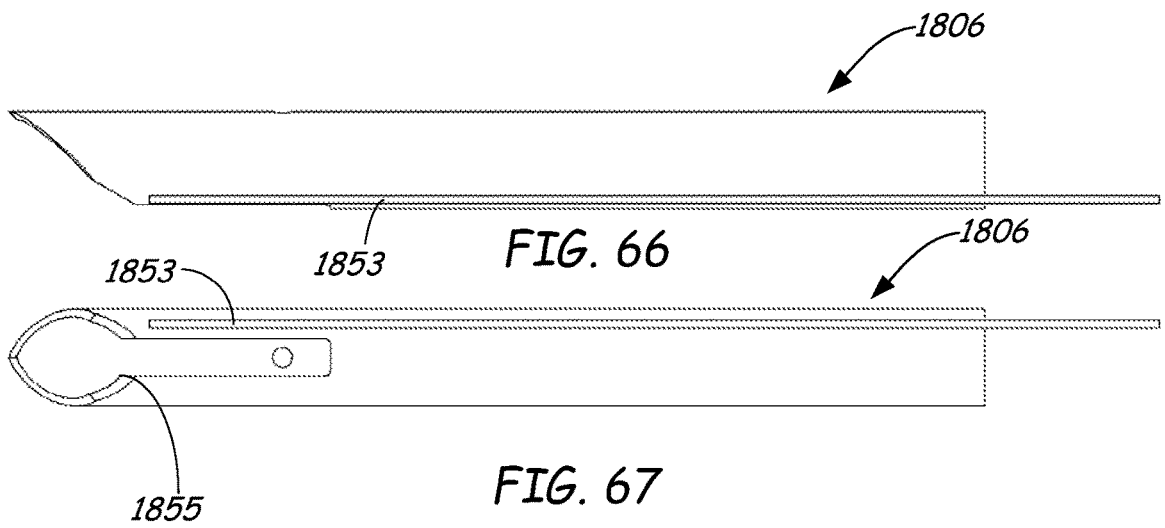
FIG. 66
FIG. 67

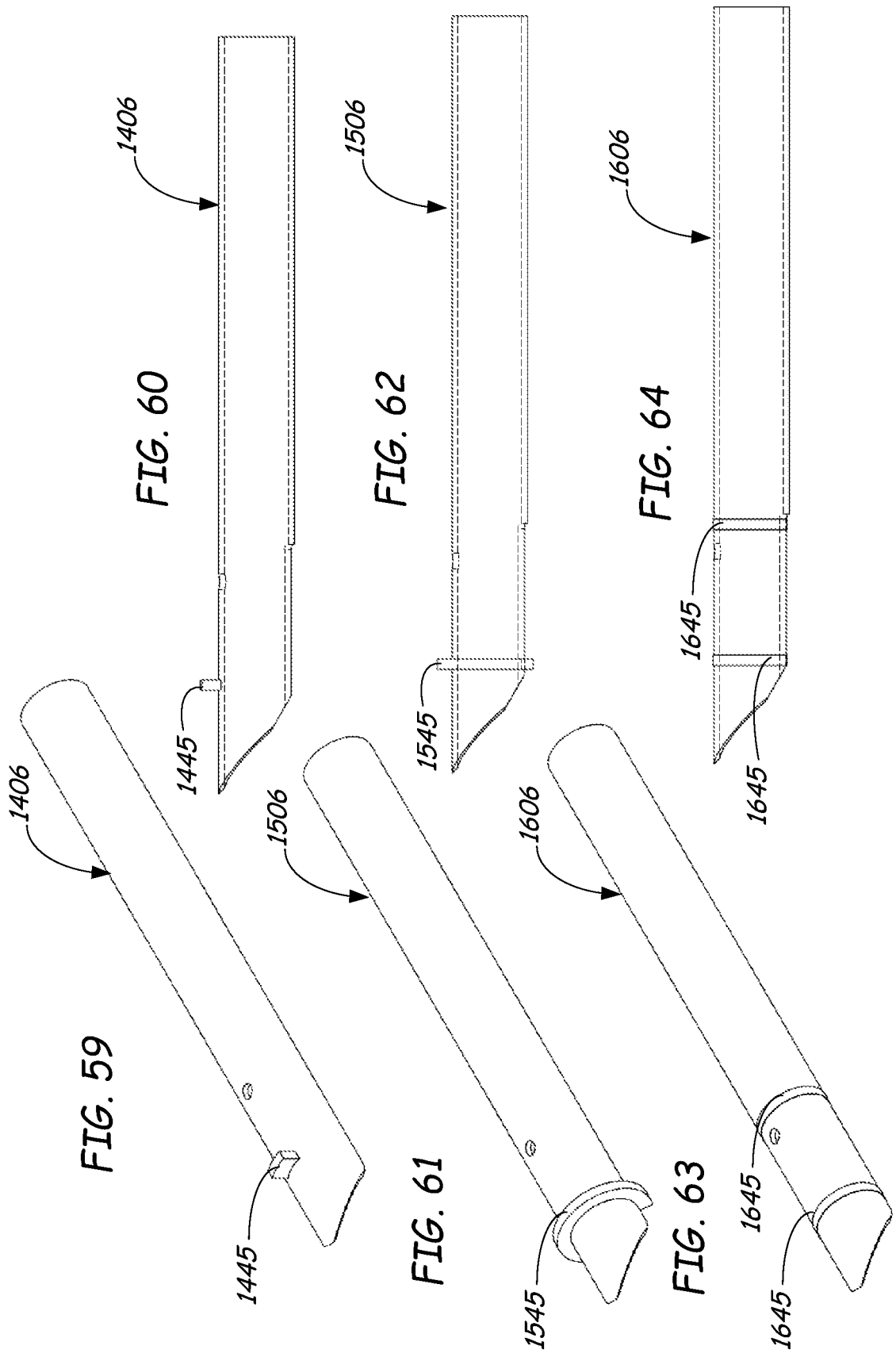

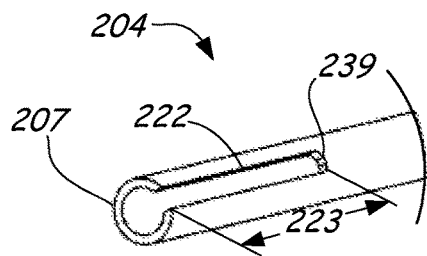
FIG. 70
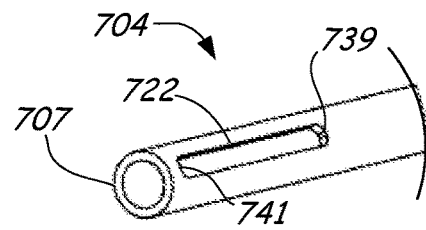
FIG. 71
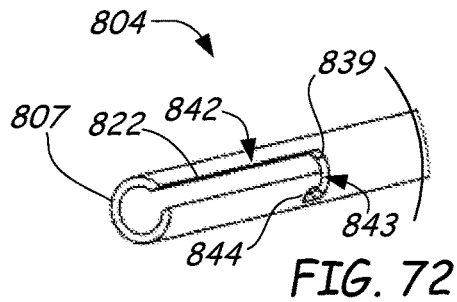
FIG. 72
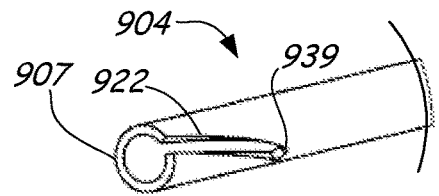
FIG. 73
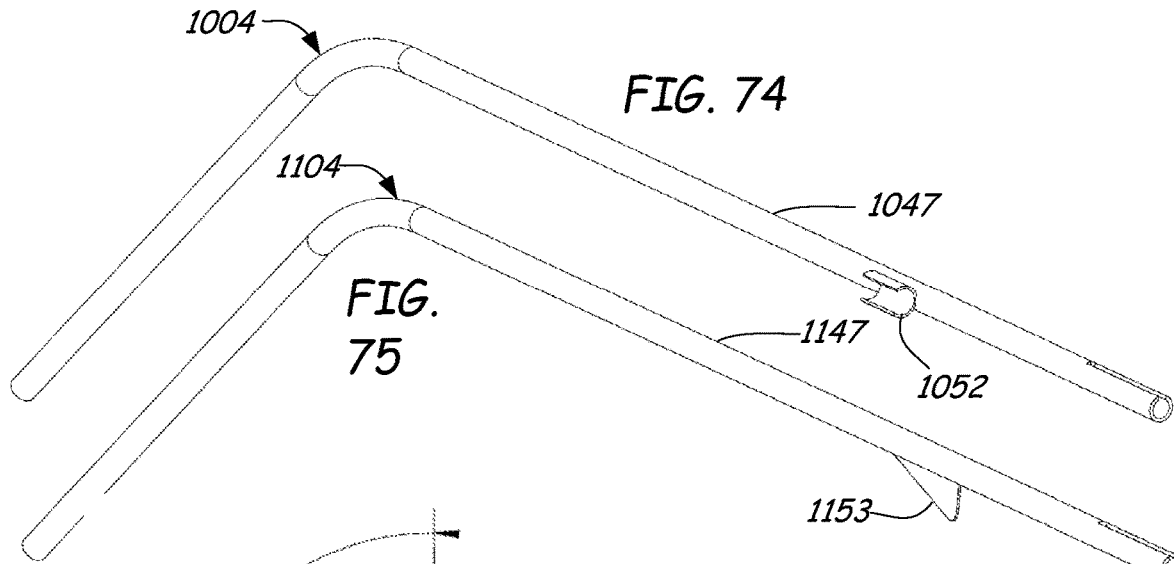
FIG. 74
FIG. 75
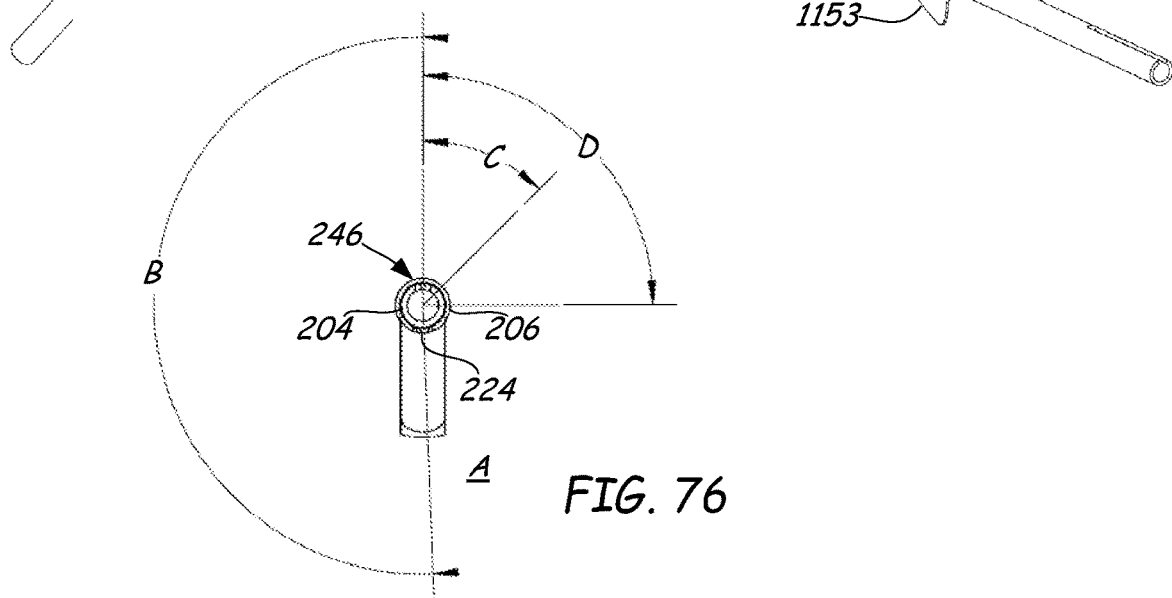
FIG. 76

INSERTION SYSTEM FOR DEPLOYING A VENTILATION DEVICE

CROSS-REFERENCE TO RELATED APPLICATION

The present application is a continuation of and claims priority to U.S. patent application Ser. No. 15/094,085, filed Apr. 8, 2016, which is a divisional application of and claims priority to U.S. patent application Ser. No. 13/826,497, filed Mar. 14, 2013, which is based on and claims the benefit of U.S. provisional patent application Ser. No. 61/660,280, filed Jun. 15, 2012, the contents of which are hereby incorporated by reference in their entireties.

BACKGROUND

Placement of middle ear ventilation tubes in the tympanic membrane is a common pediatric surgical procedure for the treatment of middle ear infection or otitis media. Also known as tympanostomy tubes or pressure equalizing (PE) tubes, the procedure involves creating an incision (i.e., a myringotomy) in the tympanic membrane and placing a tube in the incision to allow ventilation, pressure equalization and drainage from the middle ear out through the ear canal. The tube can remain in the ear for months or years.

A tube is placed in the tympanic membrane via visualization through a microscope. A sharp blade is used to create the incision and various surgical instruments are used to manipulate the tube into the incision. In the confined space of the ear canal, placement of the tube can be difficult, especially in aligning the flange at one end of the tube with the incision and the need for multiple different surgical instruments to perform the procedure. It is also not uncommon for the tube to dislodge from the surgical instrument or for it to accidentally extract from the tympanic membrane before being fully seated, requiring multiple attempts before successful placement is achieved. In addition, the large retention flanges included in most tubes make them difficult to maneuver in the ear canal and will actually block the clinician's view of the incision site.

Because the middle ear is highly innervated, repeated manipulation of the tympanic membrane is painful enough that patients, especially young children, who make up the majority of tube recipients, require general anesthesia. Such a drug therapy is costly and poses additional risks.

The discussion above is merely provided for general background information and is not intended to be used as an aid in determining the scope of the claimed subject matter.

SUMMARY

An insertion system includes a handle assembly and a nose assembly. The handle assembly includes a main body, a nose interface and an actuating element that moves from a first position to a second position. The nose assembly is removably attached to the handle assembly and having an insertion end. The nose assembly includes a nose, a positioning rod extending from the nose to a distal end, a cutting sheath surrounding a distal end of the positioning rod and including a cutting edge, an actuation member having a proximal end coupled to the actuating element when the nose assembly is attached to the handle assembly and a distal end attached to the cutting sheath, a ventilation tube located distal to the distal end of the positioning rod and proximal to the insertion end. The cutting sheath retracts from around the ventilation tube and along the positioning rod when the actuating element on the handle assembly is moved from the first position to the second position.

A method of maintaining an opening in a membrane of the body includes assembling the nose on the nose assembly to the nose interface on the main body of the handle assembly. The ventilation tube is loaded into the cutting sheath such that the ventilation tube is distal to the distal end of the positioning rod and proximal insertion end. The insertion end of the nose assembly is advanced into the body so that the cutting edge pierces the membrane and the ventilation tube is located across the membrane. The actuating element is rotated from a first position to a second position to retract the cutting sheath from around the ventilation tube and along the positioning rod. The insertion end is removed from the body.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIGS. 20-36 illustrate further embodiments of ventilation tubes having specific features that coordinate with an insertion system, such as the insertion systems illustrated in FIGS. 2-5.

FIG. 57 illustrates a bottom view of an alternative embodiment of a cutting sheath.

FIG. 58 illustrates a bottom view of another alternative embodiment of a cutting sheath.

FIGS. 59-64 illustrate different embodiments of a cutting sheath with a visual indicator or physical stop so as to provide the user with the ability to determine depth of penetration.

FIG. 65 illustrates an enlarged view of another embodiment of an insertion end a visual indicator or physical stop provided by a cutting sheath or other element positioned outwardly from the cutting sheath.

FIG. 66 illustrates a side view of one embodiment of a cutting sheath with a sensing element for detecting when the cutting sheath has made sufficient penetration.

FIG. 67 illustrates a bottom view of the cutting sheath illustrated in FIG. 66.

FIGS. 70-73 illustrate enlarged views of various embodiments of a distal end of a positioning rod.

FIGS. 74-75 illustrate perspective views of various embodiments of positioning rods that include an interface for receiving an attachment of or positioning of other devices along its side.

FIG. 76 is an end view of the insertion end of the insertion system of FIGS. 2 and 3 illustrating the relationship between the cutting sheath and the positioning rod.

DETAILED DESCRIPTION

Embodiments described herein are directed to various ventilation devices or tubes, such as ear tubes, and insertion systems or devices for inserting ventilation devices or tubes into different membranes of a body. In one particular embodiment, a ventilation tube includes a material that allows the device to remain in a deformed state during insertion into a body. After insertion through a target membrane, it is allowed to re-form its flanges or members in-situ to anchor it in place. The deformed ear tube and the insertion device that places the ventilation tube in the membrane allows for minimally invasive ventilation tube placement, which reduces the pain, cost and risks associated with conventional procedures and devices.

Figure 1:
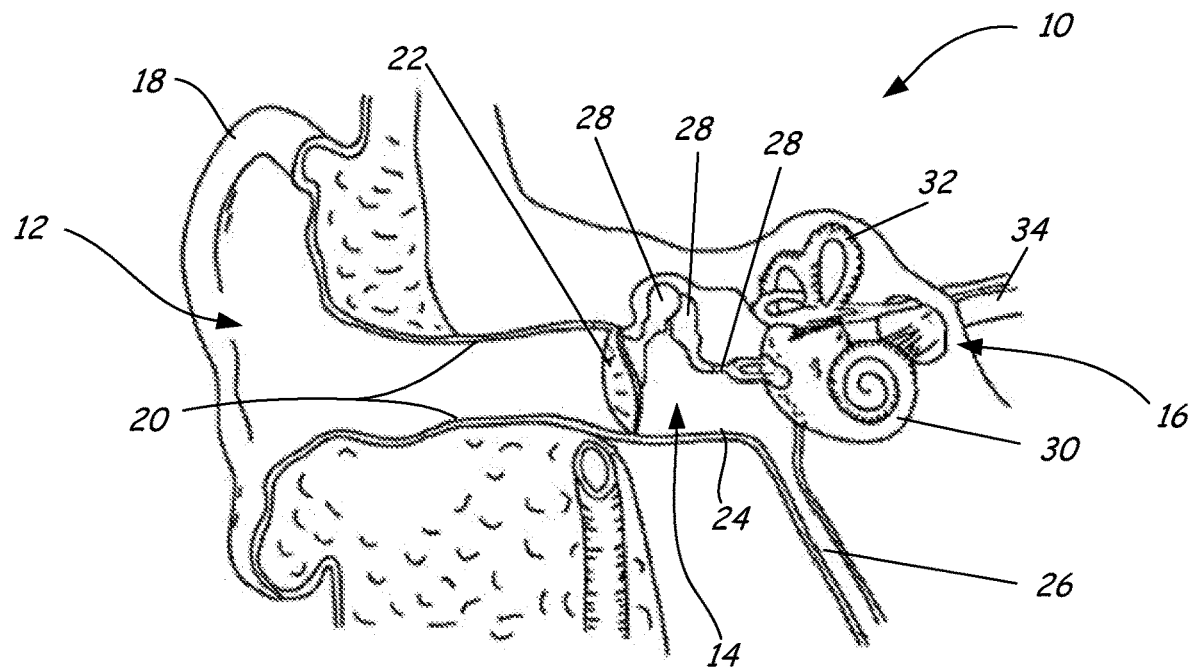
FIG. 1 is a simplified diagrammatic view of an ear.

FIG. 1 illustrates a system of organs in an ear 10 of a body that enables a person to detect sound. Ear 10 is able to change sound pressure waves into a signal of nerve impulses to be processed by the brain. Ear 10 includes an outer ear 12, a middle ear 14 and an inner ear 16. Outer ear 12 collects sound and includes the pinna 18, the ear canal 20 and an outer most layer of the ear drum or tympanic membrane (TM) 22. Pinna 18 helps direct sound through ear canal 20 to TM 22. Middle ear 14 includes an air-filled cavity 24 having an opening for the Eustachian tube 26 that is located behind TM 22. Middle ear 14 also includes ossicles bones 28. Inner ear 16 includes the fluid-filled cochlea 30 and the semicircular canals 32. Cochlea 30 is the auditory portion of the inner ear, while semicircular canals 32 are attuned to both gravity and motion. The ossicles bones 28 transmit sound from the air in cavity 24 to cochlea 30. Fluid in cochlea 30 moves in response to the vibrations coming from middle ear 14. The motion of the fluid is converted to electrical impulses, which travel along the auditory nerve 34 to structures in the brainstem for further processing. Eustachian tube 26 couples cavity 24 of middle ear 14 to the nose and mouth of a human. In a normal state, Eustachian tube 26 is collapsed. However, Eustachian tube 26 can open and close to equalize pressure in cavity 24.

An infection of the middle ear 14 can result in a buildup of fluid and increased pressure in cavity 24 causing severe pain. Children are often prone to infections of middle ear 14 because of their underdeveloped Eustachian tube 26. A myringotomy is a surgical procedure in which a tiny incision is created in TM 22 to relieve pressure caused by the excessive buildup of fluid due to an infection of the middle ear 14. If a patient requires a myringotomy, this generally suggests that Eustachian tube 26 is either partially or completely obstructed and is not able to perform its proper functions In some cases, besides making an incision in TM 22, a ventilation device or tube is inserted into the opening. Insertion of a ventilation or pressure equalizing (PE) device or tube can allow external ventilation of middle ear 14 for an extended period of time. However, in the confined space of ear canal 20, especially an ear canal of a child, insertion of a ventilation device or tube can be difficult. In one example, the incision made in TM 22 is often made larger than cross-section area of the ventilation device or tube. In such an example, the device will fall out much earlier than desired. In another example, many surgical tools need to be used to insert the device, such as a blade, a funnel (to visualize TM 22), forceps (to deliver the device), suction and a microscope. Therefore, much time is needed to prepare for the relatively simple surgery and additional time is needed during the procedure to switch between uses of the different instruments. Although this relatively brief procedure can be performed on an outpatient basis, in general, children require a general anesthetic such that they remain co-operative during the procedure. Administering anesthetic increases the time of the procedure as well as cost. A device that can alleviate these disadvantages can greatly enhance patient comfort as well as reduce procedural time and undue injury to TM 22, while simultaneously simplifying the procedure for physicians.

As discussed above, embodiments described are directed towards devices, systems and procedures for delivering a ventilation structure or tube to a membrane of a body, such as tympanic membrane 22 for treatment of a middle ear infection or otitis media. It should be realized, though, that embodiments described can be used to deliver and maintain an opening in any anatomical structure of the body whether the opening is naturally occurring or surgically created. Examples include maintaining an opening created by a tracheostomy, a cricothyrotomy and the like. In addition, embodiments are not limited to just ear ventilation, but could provide communication between any two areas in a body separated by a membrane or barrier. In addition, embodiments described can be used to deliver materials intended to communicate between two areas in a body, such as a 'wick', positioned through the TM to transport antibiotics from the ear canal into the middle ear. Embodiments described are also directed to the ventilation structure or tube itself.

While embodiments of the ventilation device or tube are illustrated as a hollow body, the device can also be a plug with no internal passageway for closing or plugging an opening. A plug can be used to block openings in a membrane, a vascular or vessel hole or create a mechanical communication between two spaces separated by a membrane, such as a membrane of a sinus cavity. The device can also be used to create communication between two lumens such as formation of vascular shunts or applied to the gastrointestinal tract and biliary system. The deployed distal members of the device may also provide better positioning of stents, in that, the larger ends can limit movement of the device/stent. For example, tracheal, bronchial, and esophageal stents are at high risk of movement from an originally deployed position. This is likely due to the symmetrical cylinder shape of the stent/device. Also, the device can be a minimally invasive way to deploy a trocar device/site.

Figure 2:
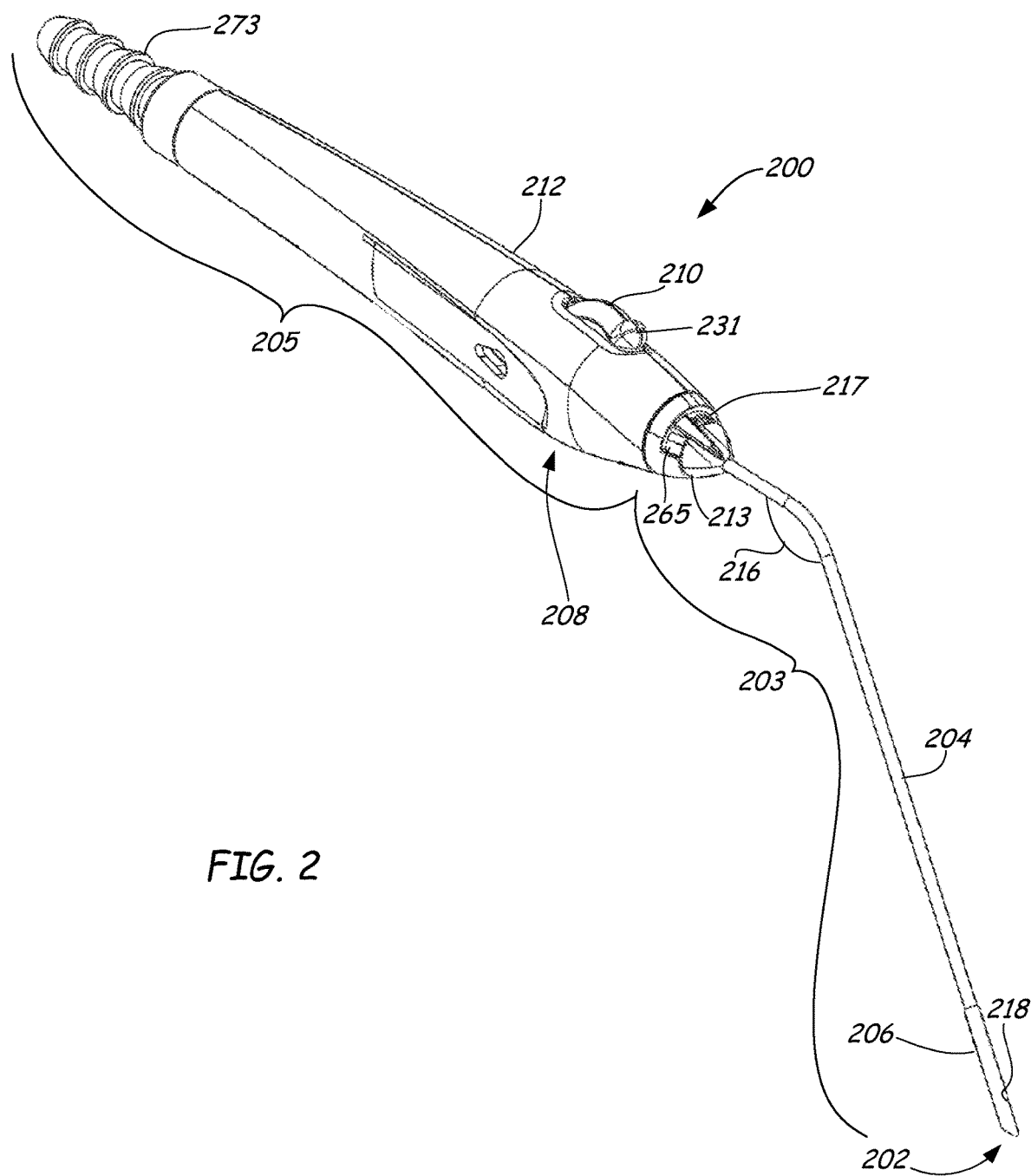
FIG. 2 illustrates a perspective view of one embodiment of an insertion system in an assembled configuration.
Figure 3:
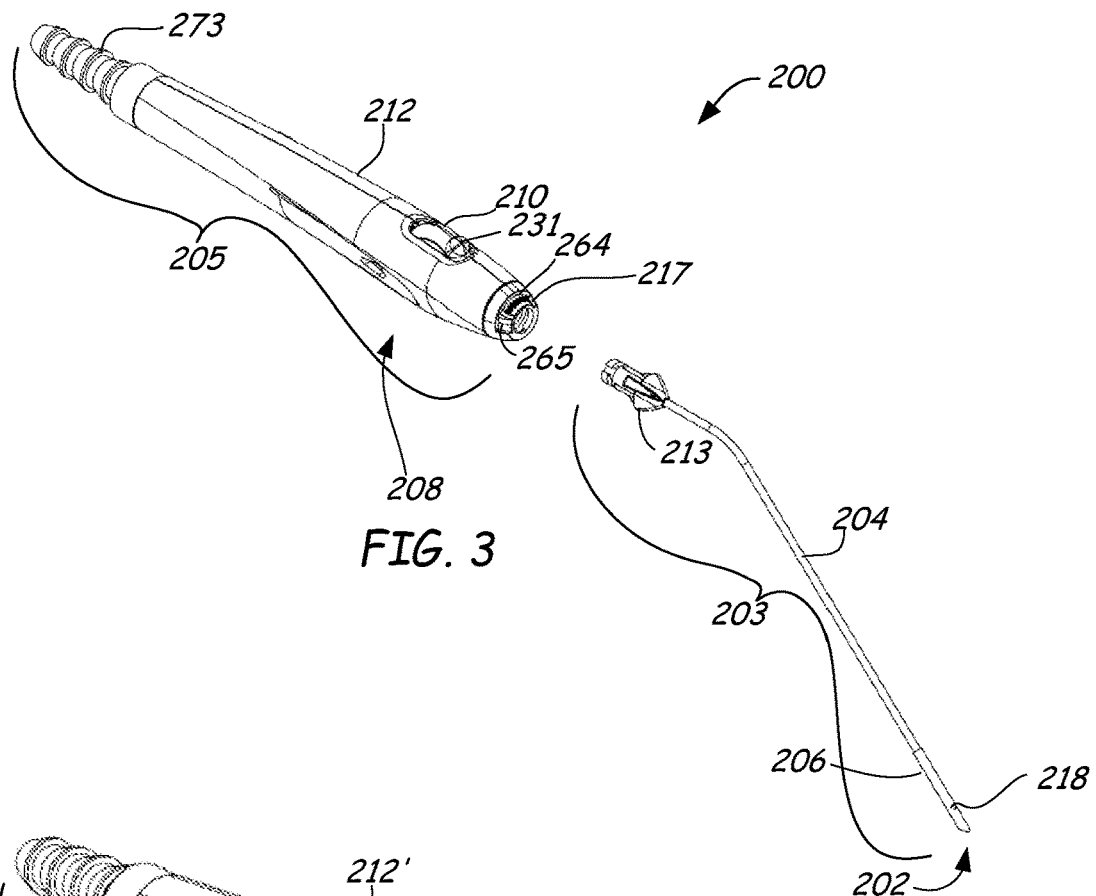
FIG. 3 illustrates a perspective view of the insertion system illustrated in FIG. 2 in a disassembled configuration.
Figure 5:
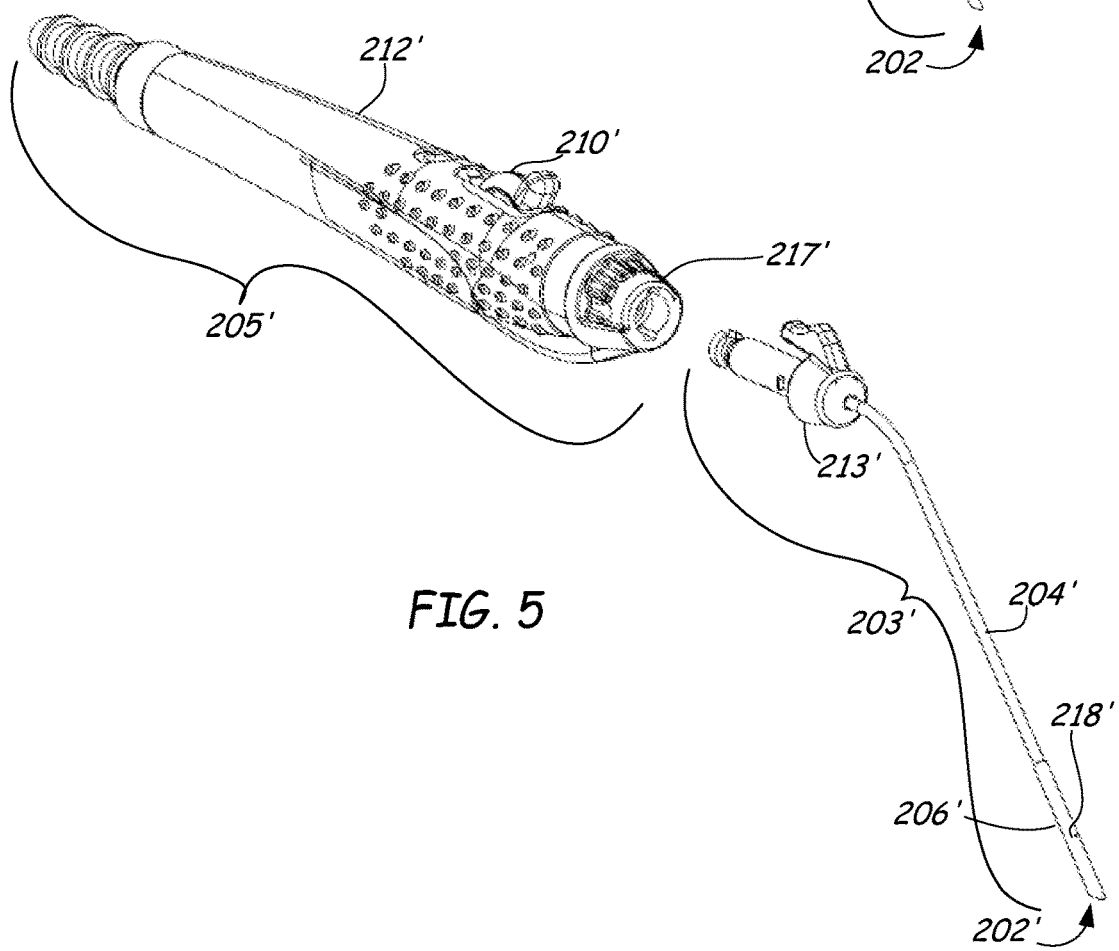
FIG. 5 illustrates a perspective view of the insertion system illustrated in FIG. 4 in a disassembled configuration.
Figure 4:
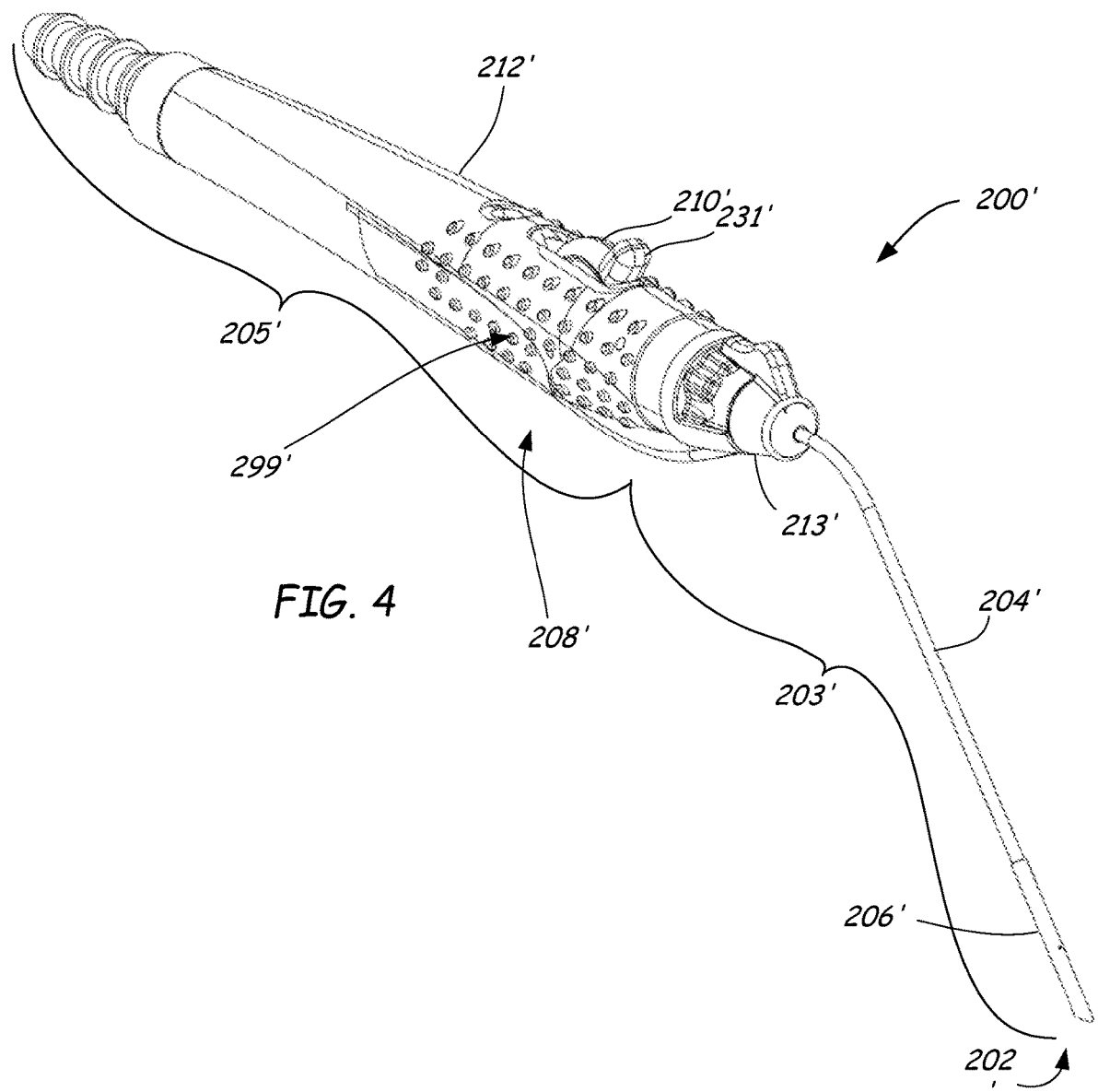
FIG. 4 illustrates a perspective view of another embodiment of an insertion system in an assembled configuration.

FIG. 2 illustrates a perspective view of one embodiment of an insertion system 200 for inserting a ventilation device or tube into an anatomical structure or membrane of a body. In FIG. 2, insertion system 200 is in an assembled configuration. FIG. 3 also illustrates a perspective view of insertion system 200, but in a disassembled configuration. FIG. 4 illustrates a perspective view of another embodiment of an insertion system 200' in an assembled configuration. FIG. 5 also illustrates a perspective view of insertion system 200', but in a disassembled configuration. Insertion system 200 or 200' includes two primary assemblies: a nose assembly 203 or 203' and a handle assembly 205 or 205'. As illustrated in FIG. 3, nose assembly 203 or 203' can be completely detached from handle assembly 205 or 205'.

Nose assembly 203 or 203' includes a hollow cutting sheath 206 or 206', a hollow positioning rod 204 or 204', a nose 213 or 213' and an actuation member 214 (illustrated in FIGS. 50, 51 and 52) that extends from nose 213 or 213' through the inside of positioning rod 204 or 204' to attach to cutting sheath 206 or 206'. An insertion end or distal end 202 or 202' of insertion system 200 or 200' defines the distal end of nose assembly 203 or 203' and is the end to which positioning rod 204 or 204', cutting sheath 206 or 206' and actuation member 214 interact to deploy a ventilation tube to a tissue or membrane of a body. In particular, cutting sheath 206 or 206' surrounds a distal portion of positioning rod 204 or 204' at insertion end 202 or 202'. Handle assembly 205 or 205' defines an actuation end or proximal end 208 or 208' of insertion system 200 or 200'. Handle assembly 208 or 208' includes a handle 212 or 212', an actuation mechanism (of which only a rotatable actuating element or scroll wheel 210 or 210' is illustrated in FIGS. 2, 3, 4 and 5) and a nose interface 217 or 217' for interfacing with nose assembly 203 or 203'. As illustrated in FIGS. 4 and 5, in one embodiment, a plurality of mechanical bumps 299' are located on an exterior surface of handle 212' to provide a better grip to a user or clinician during use, especially a user clinician who is wearing gloves. Mechanical bumps 299' can be raised portions of the material handle 212', made of an overmold material with high frictional properties, include stickers or labels and the like.

In order for insertion system 200 or 200' to function, at least a portion of a ventilation tube is deformed from its default or a rest state into a smaller constrained state. Cutting sheath 206 or 206' is the component that holds the portion of the ventilation tube in the deformed state. After cutting sheath 206 or 206' is advanced through the TM such that the ventilation tube is positioned correctly across the TM, cutting sheath 206 or 206' is retracted while the ventilation tube is held in place by positioning rod 204 or 204'.

During cutting sheath 206 or 206' retraction, the initial static friction between the ventilation tube and cutting sheath 206 or 206' needs to be overcome to allow the ventilation tube to start to slide out of the sheath. The sliding friction needs to be continuously overcome to allow cutting sheath 206 or 206' to be successfully retracted, leaving the ventilation tube in position across the TM. More specifically, The frictional force between the ventilation tube and cutting sheath 206 or 206' needs to be sufficient enough such that the ventilation tube is retained in cutting sheath 206 or 206' before cutting sheath 206 or 206' is retracted, but small enough that cutting sheath 206 or 206' can be retracted and be left in the TM.

Before discussing insertion system 200 and 200' in detail, the following is a detailed discussion of ventilation tubes in general and various embodiments of ventilation tubes that can be used with insertion system 200 or 200' for inserting into a tissue or membrane of the body. One way to control the frictional force is to control the surface area between the ventilation tube and cutting sheath 206 or 206'. As will be exemplified below, to keep frictional forces low, a majority of the length of a ventilation tube may be not in direct contact with cutting sheath 206 or 206' by slightly undersizing the axial body of the tube compared to an inner lumen diameter of cutting sheath 206 or 206'. Therefore, the only portions of the ventilation tube that are in a deformed state are the flange or flanges. It is also possible to control the surface area between the ventilation tube and cutting sheath 206 or 206' based on the geometry of the flange or flanges of the tube. The diameter of the flange or flanges can be made larger or smaller to increase or decrease contact area and therefore increase or decrease friction. Portions of the flange or flanges can be removed or added or other features that do not function as flanges can be added or removed to increase or decrease contact area.

Another way to control the frictional force is to control the normal force between the ventilation tube and cutting sheath 206 and 206'. As will be exemplified below, a thickness of the flange or flanges can be controlled. For example, a thicker, more structural flange exerts a larger outward force and increased friction. The choice of material for the ventilation tube also can impact friction forces. Tubes that resist deformation generate greater normal forces. For example, a tube material with a durometer appropriate for maintaining axial rigidity during deployment without generating excessive radial normal forces result can be chosen. The tube needs to be stiff enough that it can be pushed out of cutting sheath 206 or 206' without collapsing axially, but soft enough that the flange or flanges can be compressed without generating too high of a friction force.

A third way to control the frictional force is to control the coefficient of friction between the ventilation tube and cutting sheath 206 and 206' by altering the surface of one or both of the ventilation tube and cutting sheath 206 or 206', by selecting specific materials of one or both of the ventilation tube and cutting sheath 206 or 206' or introducing a surface modifying agent to one or both of the ventilation tube and cutting sheath 206 and 206'. For example, providing a fine texture to the inside of cutting sheath 206 or 206' can reduce friction between the ventilation tube and cutting sheath 206 or 206' by reducing the contact surface area on a microscopic level. Likewise, texturing one or more surfaces on the ventilation tube can have a similar effect. In another example, surface coatings or treatments can be applied to the ventilation tube or cutting sheath 206 or 206' to modify their frictional properties. For example, the tube could b molded from a material is naturally lubricious or has an inherent lubricant, such as self-lubricating silicone rubber (i.e., Nusil MED1-4955). Cutting sheath 206 or 206' could be coated with parylene to alter frictional properties without negatively impacting its cutting capabilities. In addition, tubes could be made from one or more materials with different properties to optimize for strength and surface properties where needed. For example the axial body could be made of a stiffer material, while the flange or flanges or other features that are to be compressed or deformed could be made of a softer material and/or of a material with a lower coefficient of friction. Further, lubricant, such as a silicone grease or oil, sterile saline or other suitable liquid can be placed on or between the tube and cutting sheath 206 or 206'. Still further, the tube can be given a partial "set" in the deformed position in cutting sheath 206 or 206'. This can be done over time or accelerated with heat. For example, a tube loaded into a sheath exhibits a certain normal force and resulting frictional resistance to deployment that can change over time as the material in the tube "relaxes" in the deformed state. This relaxation can be accelerated, for example, by exposing the tube to elevated temperatures.

Still further, axial compression of a ventilation tube, or other delivered object, may be desirable in certain applications. The friction between the ventilation tube and the cutting sheath can be used to axially compress the body of a tube, shortening the space between two points along it's body. For example, the distance between a medial flange and a visualization tab on a tube may be longer in its natural, relaxed state than when it is compressed inside a cutting sheath. In this embodiment, the tube would be loaded into the cutting sheath, and the cutting sheath may be retracted along the positioning rod such that the tube is compressed axially inside the cutting sheath, decreasing the distance between the medial flange and visualization tab. Additional retraction would result in no or minimal additional axial compression before restraining frictional forces would be overcome and the tube would be deployed.

FIGS. 6-49 illustrate ventilation or tympanostomy tubes with specific features that improve their ability to function in conjunction with insertion system 200 illustrated in FIGS. 2 and 3 and with insertion system 200' illustrated in FIGS. 4 and 5. In particular, FIGS.—6-17 describe grommet-type ventilation tubes. FIGS. 18-36 describe a variation of grommet-type ventilation tubes and FIGS. 37-43 describe T-tube type ventilation devices.

Figure 6:
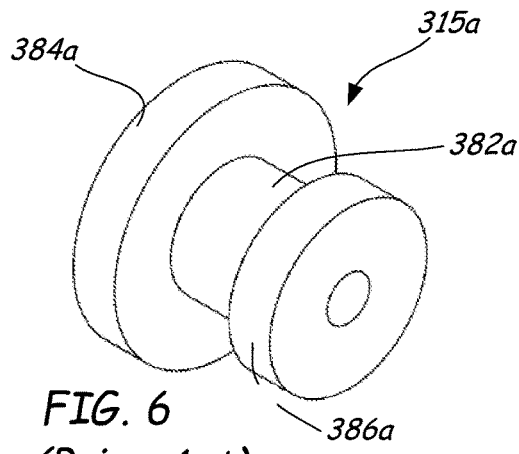
FIGS. 6-7 illustrate related art ventilation tubes having specific features that coordinate with an insertion system, such as the insertion systems illustrated in FIGS. 2-5.
Figure 7:
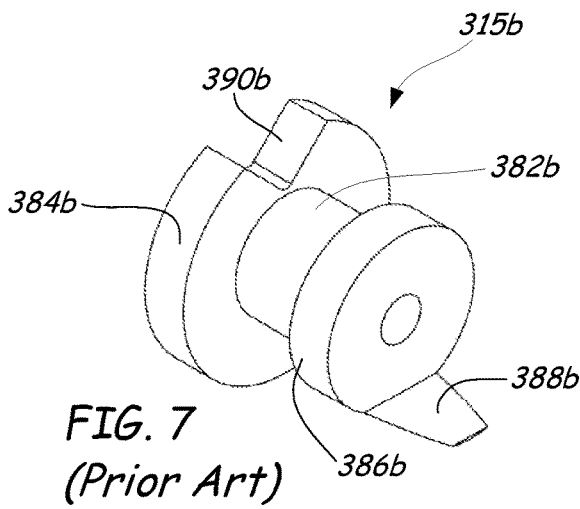

FIGS. 6 and 7 illustrate exemplary grommet-type tubes that exist in the prior art, while FIGS. 8-17 illustrate grommet-type tubes according to various embodiments of the disclosure. FIG. 6 illustrates exemplary prior art grommet-type ventilation tube 315a. Grommet tube 315a includes a hollow main body 382a having parallel flanges. In particular, grommet-type tube 315a includes a medial flange 384a that is to be located internal to the TM of a patient and a lateral flange 386a to be located external to the TM of a patient. As illustrated, medial flange 384a includes an outer diameter that is greater than an outer diameter of lateral flange 386a. In this way, grommet-type tube 315a is less likely to fall out of the TM too early.

FIG. 7 illustrates an exemplary prior art grommet-type ventilation tube 315b known as a Paparella grommet tube. Grommet tube 315b is commercially available through many ventilation tube manufacturers including, but not limited to, Summit Medical, Inc. of St. Paul, Minnesota Like tube 315a, tube 315b includes a hollow main body 382b having a medial flange 384b and a lateral flange 386b. Unlike tube 315a, grommet tube 315b also includes a tab 388b located on lateral flange 386b and a notch 390b located on medial flange 384b. In conventional applications, tab 388b is grasped with an instrument, such as a forceps, and notch 390b is provided to help insert medial flange 384b through the tissue. For use with insertion system 200, tab 388b is bent substantially perpendicularly from the outer diameter of lateral flange 386b when loaded into cutting sheath 206 such that tab 388b is allowed to protrude through a slot in cutting sheath 206 for purposes of visualization, while medial flange 384b and lateral flange 386b are compressed in the cutting sheath for later deployment.

Figure 8:
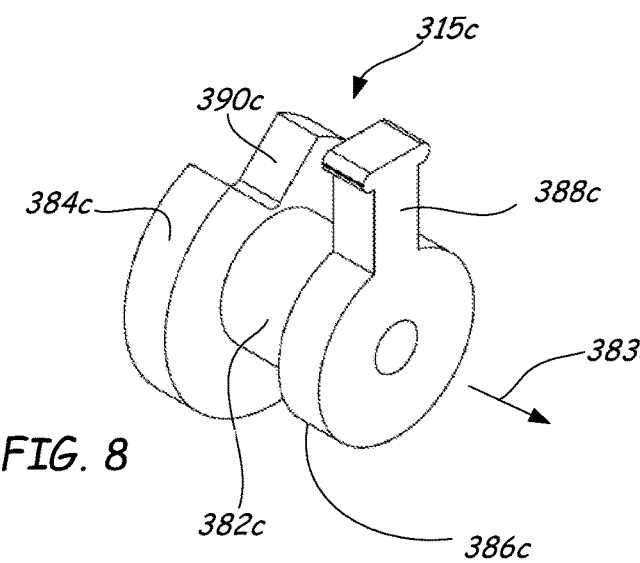
FIGS. 8-17 illustrate embodiments of ventilation tubes having specific features that coordinate with an insertion system, such as the insertion systems illustrated in FIGS. 2-5.
Figure 9:
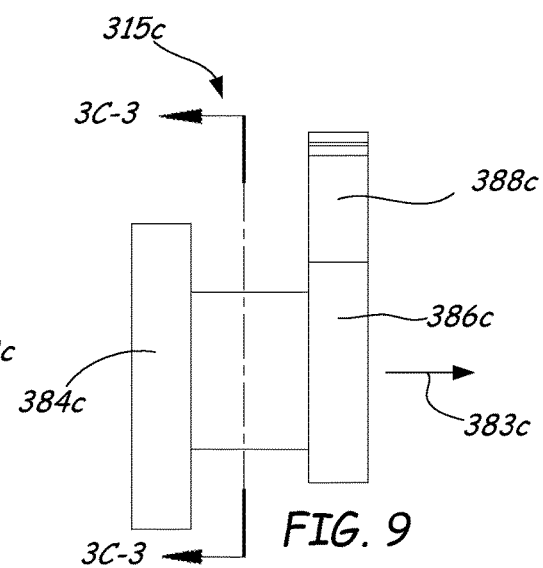
Figure 10:
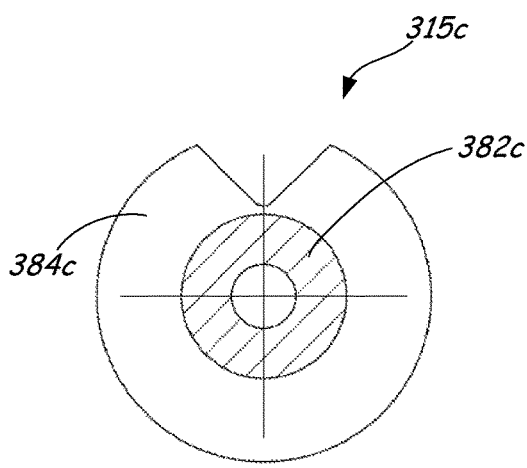

In the alternative, FIGS. 8, 9 and 10 illustrate a perspective view, a side view and a section view of a ventilation tube 315c according to one embodiment Like tubes 315a and 315b, tube 315c includes a hollow main body 382c having a medial flange 384c, a lateral flange 386c, a notch 390c and visualization tab 388c. Rather than having a tab that extends in a lateral direction 383c along the outer diameter of the lateral flange and must be bent substantially perpendicular from the lateral direction in its loaded configuration as is the case with tube 315b, visualization tab 388c is formed to extend from the outer diameter of the lateral flange 386c, but in a direction substantially perpendicular to the lateral direction 383c. In this way, visualization tab 388c need not be manipulated during loading to cause the tab to extend through the slot in the cutting sheath 206 because it is premade to do so. Visualization tab 388c includes a wider distal end than a proximal end that is coupled formed with lateral flange 386c. In one embodiment, the width at the proximal end approximately corresponds with the width of the slot in the cutting sheath through which visualization tab 388c protrudes through, while the width of the distal end is greater than the width of the slot in the cutting sheath.

Figure 11:
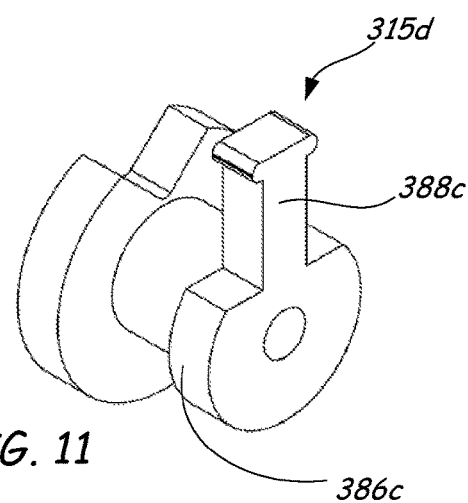
Figure 12:
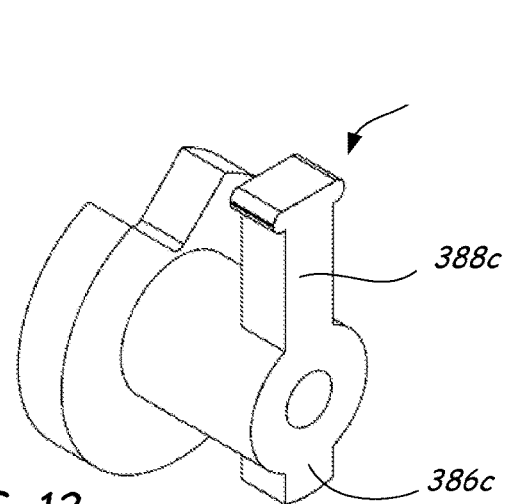
Figure 13:
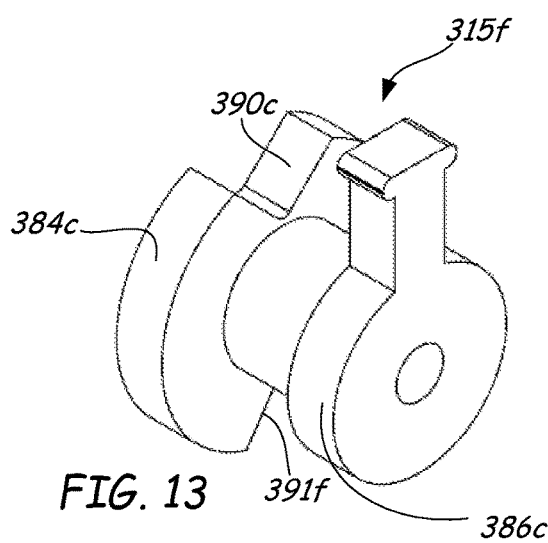

Compared to FIGS. 8-10, tube 315d and 315e of FIGS. 11 and 12 illustrate that some or all of lateral flange 386c could be removed when the tube is formed according to alternative embodiments. Compared to FIGS. 8-10, FIG. 13 illustrates a tube 315f with an additional notch 391f on medial flange 384c, which in FIG. 13 is located opposite notch 390c according to another alternative embodiment. Removing a portion or portions of the medial or proximal flanges 384c or 386c can reduce the amount of flange material that must be compressed inside the sheath component, making it easier to load and/or deploy the ventilation tube. In addition, the location of a notch can provide a preferential location for the flange to fold during loading into a cutting sheath. Predictable folding into a cutting sheath allows for a more repeatable process for loading and for deploying, and allows for a planned 'compressed' state that the ventilation tube flanges will occupy while constrained within the sheath.

Figure 14:
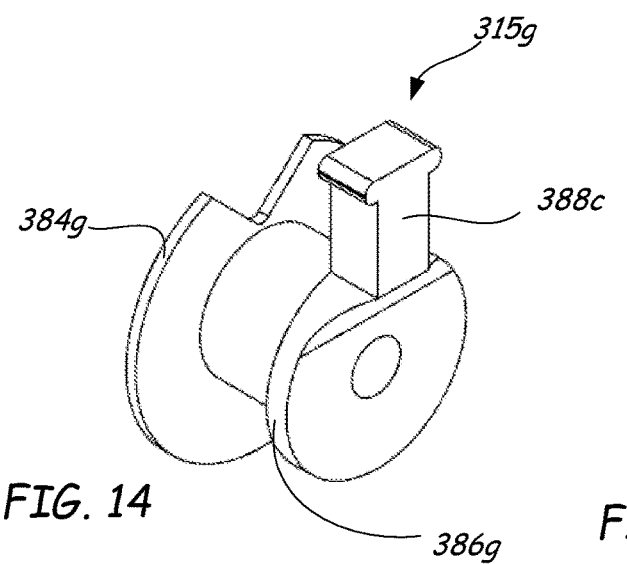

Compared to FIGS. 8-10, FIG. 14 illustrates a tube 315g with a medial flange 384g that is thinner than a standard ventilation tube, and a lateral flange 386g of varying thickness according to yet another alternative embodiment. It should be understood that one, both or none of the medial or lateral flanges could be thinner, or could be of varying thickness. Providing a thinner flange reduces the amount of material in the flange, allowing it to be constrained inside of a cutting sheath with a smaller inside diameter. Medial and lateral flanges of varying thickness combine the benefit of a thinner flange in reducing overall mass, while retaining strength and physical properties where needed. For example, the thicker part of the flange in FIG. 14 is located proximal to tab 388c that interfaces with the slot in the cutting sheath 206. To ensure that tab 388v remains positioned correctly, a slightly thicker flange support may be desirable.

Figure 15:
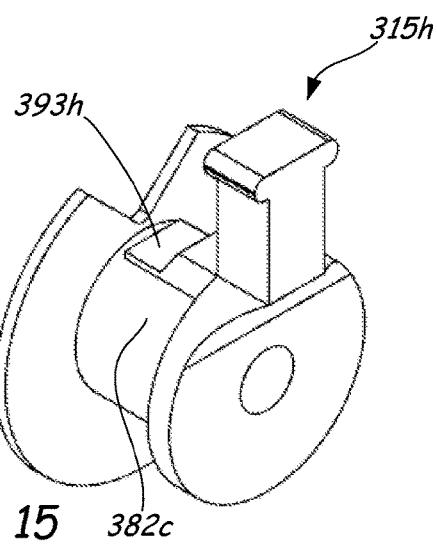

Compared to FIG. 14, FIG. 15 illustrates a tube 315h with a slot interface element 393h located along the length of hollow main body 382c according to yet another alternative embodiment. Slot interface element 393h may provide additional interface area between the tube 315h and a cutting sheath to maintain registration during loading or deployment. It may also provide additional strength along the length of the hollow main body 382c of the tube to prevent the tube from collapsing longitudinally during deployment from the cutting sheath.

Figure 16:
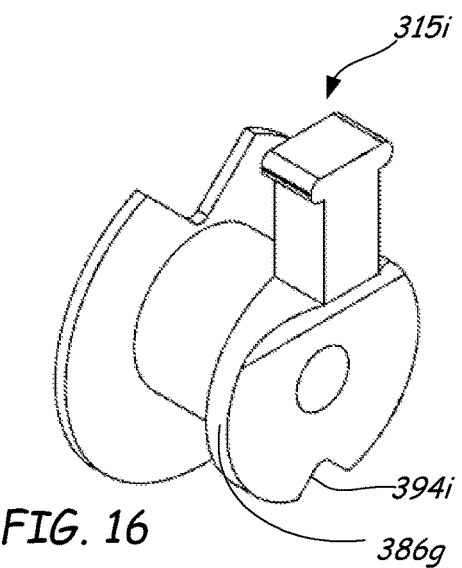
Figure 17:
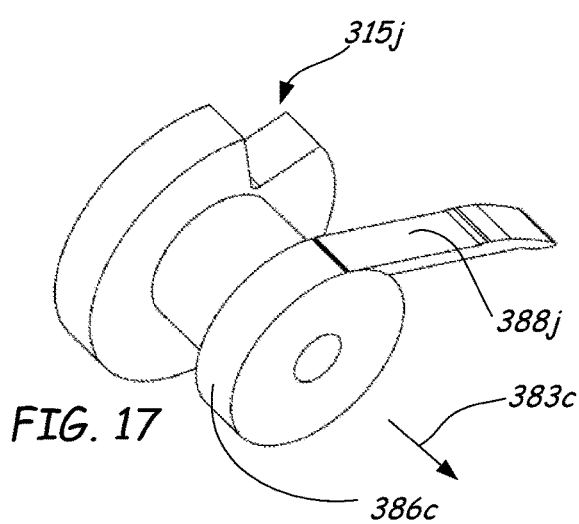

Compared to FIG. 14, FIG. 16 illustrates a ventilation tube with a notch 394i on lateral flange 386g. A notch or plurality of notches on lateral flange could provide a material reduction to allow the notch to fold along predictable bends during insertion into the sheath component. In addition, the location of notches, or gaps in the lateral flange could allow for loading tools or accessories to pass along and through the flange at those points. A notch or notches could also allow ventilation tube 315i to be registered to a loading tool or accessory to aid in subsequent registration and loading into a sheath component.

In yet another alternative embodiment and compared to FIGS. 7-10, FIG. 17 illustrates a ventilation tube 315j with a tab 388j that is different than tab 388b or visualization tab 388c of tubes 315b or 315c. Rather than having a tab that extends in a lateral direction 383c along the outer diameter of the lateral flange and must be bent substantially perpendicular from the lateral direction in its loaded configuration as is the case with tube 315b or a visualization tab 388c that extends from the outer diameter of the lateral flange 386c in a direction substantially perpendicular to the lateral direction 383c, visualization tab 388j has a thickness that corresponds with the thickness of the lateral flange 386c and extends outward at a tangent from the outer diameter of lateral flange 386c.

Figure 18:
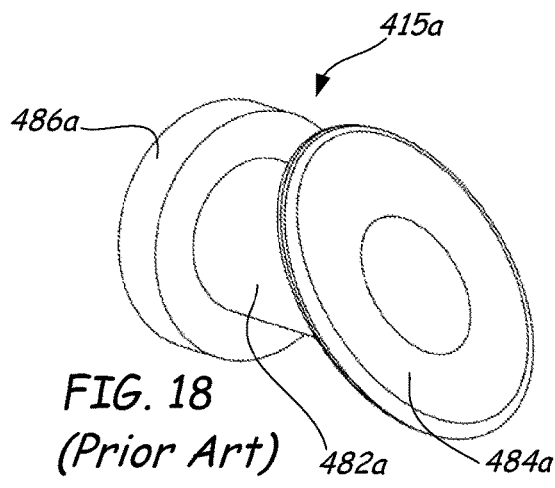
FIGS. 18-19 illustrate related art ventilation tubes having specific features that coordinate with an insertion system, such as the insertion systems illustrated in FIGS. 2-5.
Figure 19:
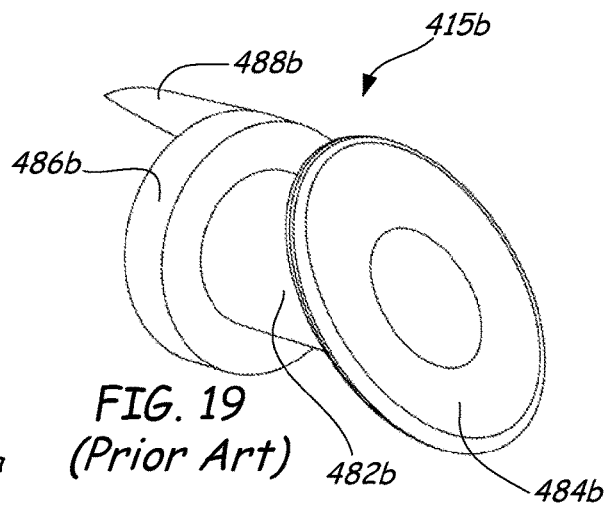

FIGS. 18 and 19 illustrate exemplary grommet-type tubes that exist in the prior art, while FIGS.—20-33 illustrate grommet-type tubes according to various embodiments of the disclosure. FIG. 18 illustrates exemplary prior art grommet-type ventilation tube 415a known as an Armstrong grommet tube that does not have parallel flanges. Grommet tube 415a is commercially available through many ventilation tube manufacturers including, but not limited to Summit Medical, Inc. of St. Paul, Minnesota Grommet tube 415a includes a hollow main body 482a having a medial flange 484a that is to be located internal to the TM of a patient and a lateral flange 486a to be located external to the TM of a patient. As illustrated, medial flange 484a includes a bevel that corresponds to an angle that makes it easier to insert tube 415a into a TM of a patient. While presenting a beveled medial end to a TM during insertion to make it easier to insert, the lateral end of the tube should be "squared" for presenting to the positioning rod of the insertion system. Of course, it is possible that the lateral end could be "non-square" as long as the frictional force resisting deployment is low enough.

FIG. 19 illustrates another exemplary prior art grommet-type ventilation tube 415b, which is the Armstrong grommet tube with a tab 488b. Grommet tube 415b is also commercially available through many ventilation tube manufacturers including, but not limited to Summit Medical, Inc. of St. Paul, Minnesota Like tube 415a, tube 415b includes a hollow main body 482b having a beveled medial flange 484b and a lateral flange 486b. Unlike tube 415a, grommet tube 415b also includes a tab 488b located on lateral flange 486b. In conventional applications, tab 488b is grasped with an instrument, such as a forceps. For use with insertion system 200, tab 488b is bent substantially perpendicularly from the outer diameter of lateral flange 486b when loaded into cutting sheath 206, such that tab 488b is allowed to protrude through a slot in cutting sheath 206 for purposes of visualization, while medial flange 484b and lateral flange 486b are compressed in the cutting sheath for later deployment.

Figure 20:
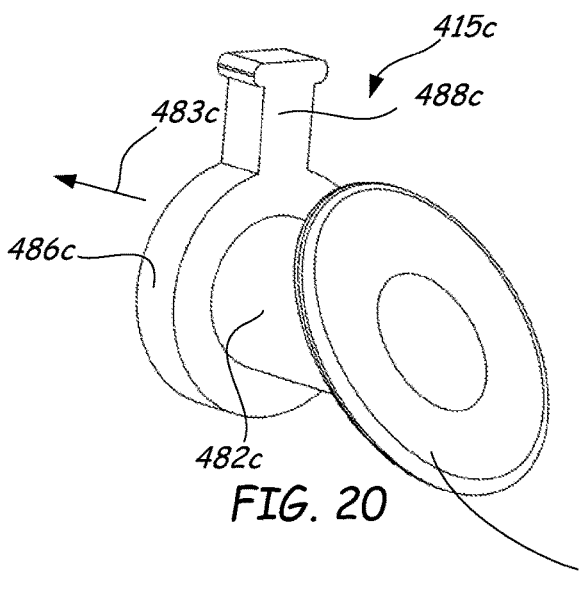

Similar modifications to those illustrated in figures—6-16 can be applied to tubes 415a and 415b. For example, FIG. 20 illustrates a ventilation tube 415c according to one embodiment. Like tubes 415a and 415b, tube 415c includes a hollow main body 482c having a medial flange 484c, a lateral flange 486c and visualization tab 488c. Rather than having a tab that extends in a lateral direction 483c along the outer diameter of the lateral flange and must be bent substantially perpendicular from the lateral direction in its loaded configuration as is the case with tube 415b, visualization tab 488c is formed to extend from the outer diameter of the lateral flange 486c, but in a direction substantially perpendicular to the lateral direction 483c. In this way, visualization tab 488c need not be manipulated during loading to cause tab 488c to extend through the slot in the cutting sheath 206 because it is premade to do so. Visualization tab 488c includes a wider distal end than a proximal end that is formed with lateral flange 486c. In one embodiment, the width at the proximal end approximately corresponds with the width of the slot in the cutting sheath through which visualization tab 488c protrudes through, while the width of the distal end is greater than the width of the slot in the cutting sheath.

Figure 21:
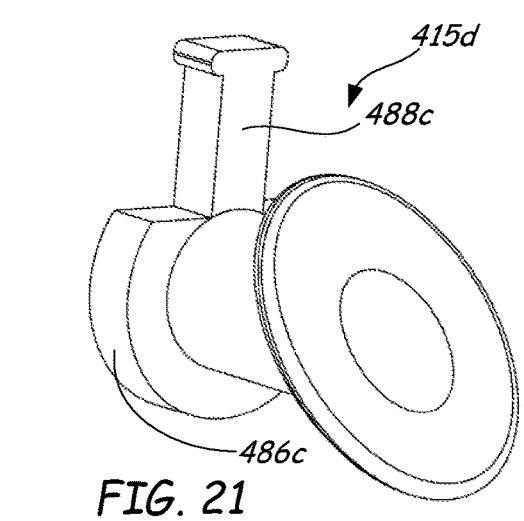
Figure 22:
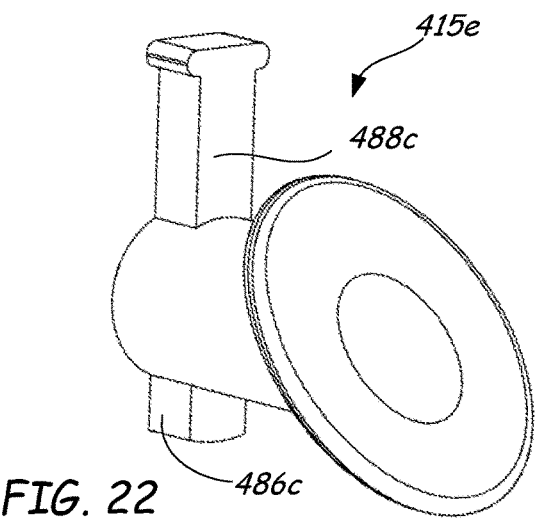
Figure 23:
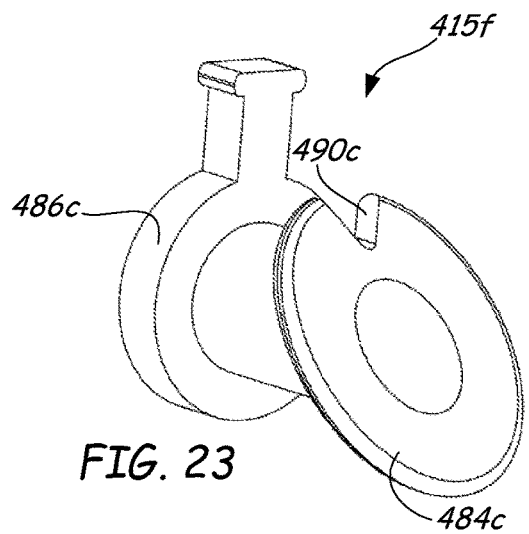

Compared to FIG. 20, tube 415d and 415e of FIGS. 21 and 22 illustrate that some or all of lateral flange 486c could be removed when the tube is formed according to alternative embodiments. Compared to FIG. 20, FIG. 23 illustrates a tube 415f with a notch 490f in medial flange 484c and FIG. 24 illustrates a tube 415g with a second notch 491g in medial flange 484c, which in FIG. 24 is located opposite notch 390c according to another alternative embodiment.

Figure 24:
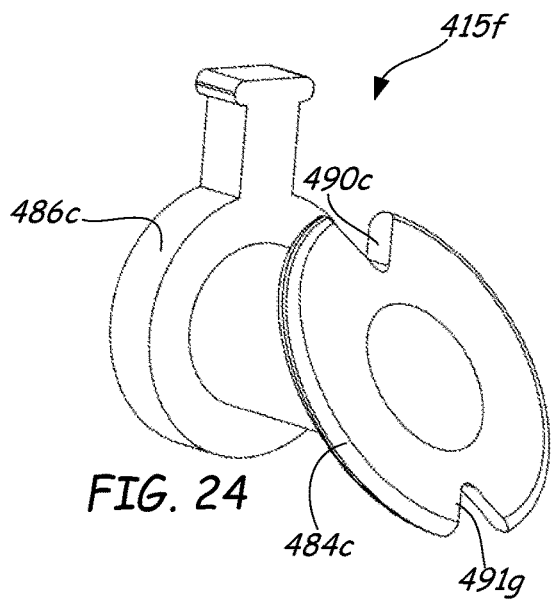
Figure 25:
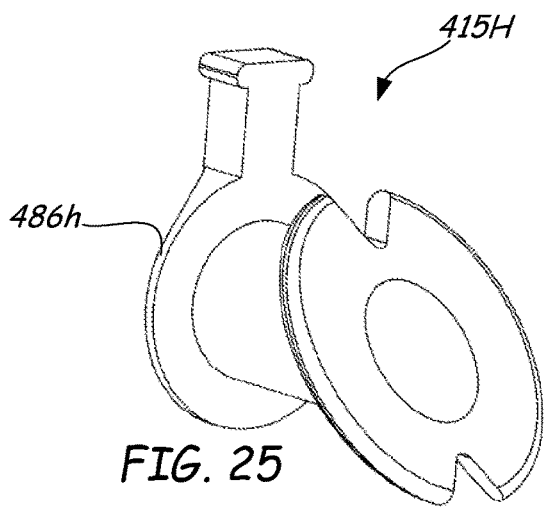
Figure 26:
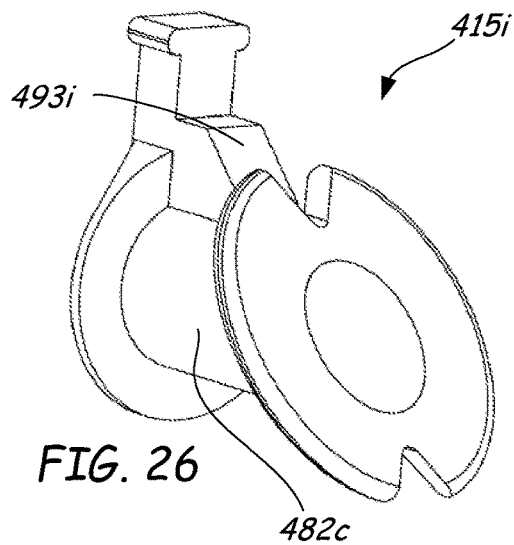
Figure 27:
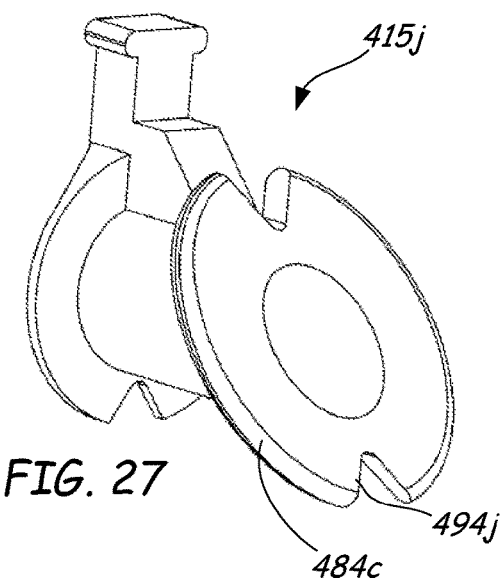

Compared to FIG. 24, FIG. 25 illustrates a tube 415h with a lateral flange 486h of varying thickness according to yet another alternative embodiment. Compared to FIG. 24, FIG. 26 illustrates a tube 415i with a slot interface element 493i located along the length of hollow main body 482c according to yet another alternative embodiment. Slot interface element 493i may provide additional interface area between the tube 415i and a cutting sheath to maintain registration during loading or deployment. Compared to FIG. 26, FIG. 27 illustrates a ventilation tube 415j with a notch 494j in lateral flange 486c. A notch or plurality of notches on lateral flange could provide a material reduction to allow the notch to fold along predictable bends when located into the cutting sheath. In addition, the location of notches, or gaps in the lateral flange could allow for loading tools or accessories to pass along and through the flange at those points. A notch or notches could also allow ventilation tube 415i to be registered to a loading tool or accessory to aid in subsequent registration and loading into a sheath component.

Figure 28:
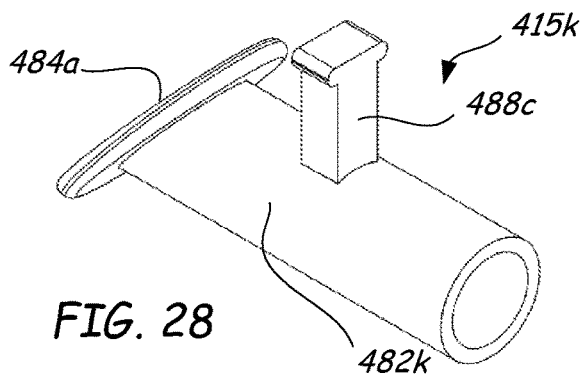
Figure 29:
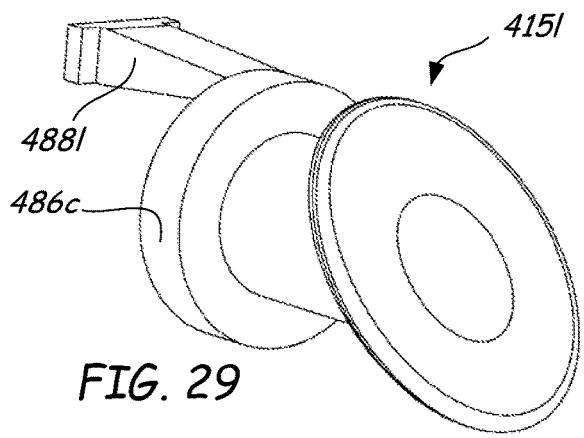

FIG. 28 illustrates a perspective view of yet another alternative embodiment of a ventilation tube 415k. In this embodiment, the hollow main body or lumen 482k of ventilation tube 415k extends from medial flange 484a and beyond visualization tab 488c. In cases where a long hollow main body is desired, as is shown in FIG. 28, the lateral flange or the visual indicator 488c may not be located at the far lateral end of the tube so that the visual indicator can be used to determine correct placement without excessive penetration behind the TM which could damage the back wall of the inner ear. As shown, hollow main body 482k extends past visualization tab 488c to ensure that the tube does not fall inside the TM, even if the device is slightly over-inserted through the TM. FIG. 29 illustrates a perspective view of yet another alternative embodiment of a ventilation tube 415L. Like FIG. 19, tab 488l extends in a lateral direction from the outer diameter of the lateral flange 486c, but includes a tab having a wider distal end than a proximal end.

FIG. 30 illustrates a perspective view of yet another alternative embodiment of a ventilation tube 415m. In this embodiment, like tube 415k, the tube 415m includes hollow main body or lumen 482k that extends from medial flange 484m and beyond visualization tab 488m. As shown, hollow main body 482k extends past the lateral flange or visualization tab 488m to ensure that the tube does not fall inside the TM, even if the device is inserted too far through the TM. FIG. 31 illustrates a perspective view of yet another alternative embodiment of ventilation tube 415n. Ventilation tube 415n is like ventilation tube 415m, except, medial flange 484n is trimmed along edge 490n. Trimmed edge 490n increases the clearance between medial flange 484n and visualization tab 488m, providing more leeway on placement across the TM. FIG. 32 illustrates a perspective view of yet another alternative embodiment of a ventilation tube 415o. Like tube 415n, tube 415o includes a trimmed medial flange 484n and visualization tab 488m. However, hollow main body or lumen 482o extends beyond visualization tab 488m a shorter axial length. To compensate for the shorter axial length, an extra lateral tab 486o, besides the use of visualization tab 488m as a lateral flange, substantially opposes visualization tab 488m to keep the tube from falling inside or behind the TM. In addition, lateral tab 486o can be folded back while it is loaded in the cutting sheath so that it is positioned as far away from the cutting edge of the cutting sheath as possible to ensure that it is deployed last, or as far lateral as possible, minimizing the chance of over-insertion during deployment.

FIG. 33 illustrates a perspective view of yet another alternative embodiment of a ventilation tube 415p. In this embodiment, like tube 415n, tub 415p includes a trimmed medial flange 484n and a lateral flange or visualization tab 488m. However, the portion of hollow main body or lumen 482p that extends past visualization tab 488m is split along its axial length from visualization tab 488m to lateral end 48'7p for preventing the inner lumen from plugging with effusion. The split provides many advantages. For example, the split minimizes the axial length of the inner lumen of tube 415p, the split provides a shorter section of small diameter inner lumen, the split helps to hold the tube from falling into the middle ear post deployment by acting as a lateral flange and the split makes it easier to unplug a tube that has become plugged.

Figure 34:
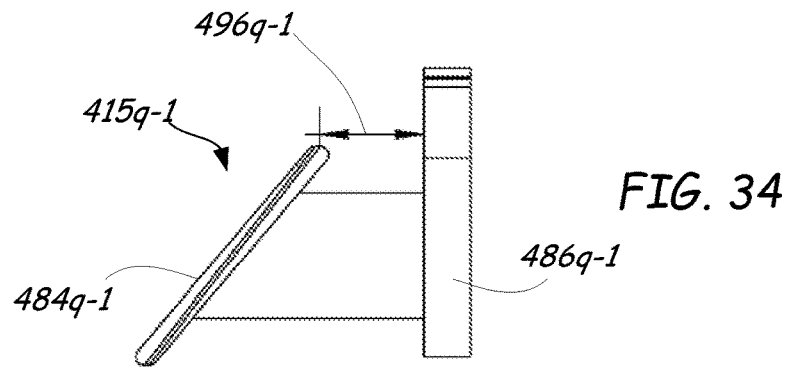
Figure 35:
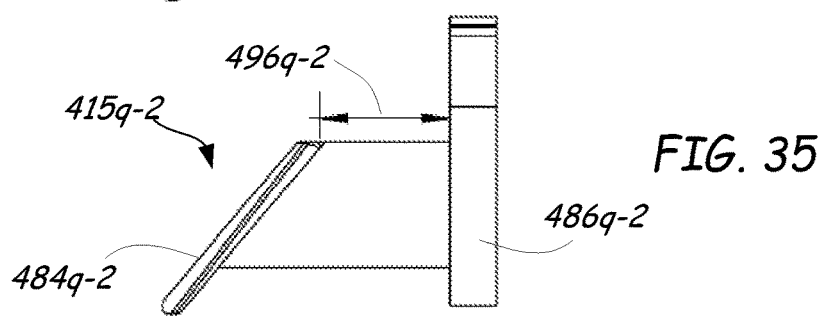
Figure 36:
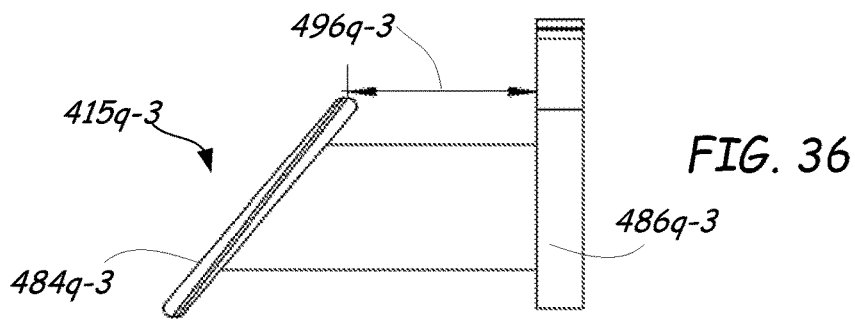

In addition, while the minimum distance between the medial and lateral flanges for the tubes shown in FIGS. 6-17 can only be increased or decreased by changing the length of the hollow main body, as illustrated in FIGS. 34, 35 and 36, this distance 496q-1, 496q-2 and 496q-3 can be modified for the tubes shown in FIGS.—18-27 by changing the placement of either medial flange 484q-1, 484q-2 and 484q-3 or lateral flange 486q-1, 486q-2, and 486q-3 or by removing or trimming the medial flange 484q-2 as illustrated in FIG. 35 (i.e., any flange that is not positioned at a right angle to the axis of the hollow main body of a grommet-type ventilation tube). Placement of the medial flange changes the distance between the lateral and medial flanges (whether smaller or larger) to make insertion of the ventilation tube easier. Because the user must position the device across the TM using visual indicators of depth, a longer hollow main body would allow for a larger range of acceptable positioning of the tube which results in successful deployment across the TM.

Figure 37:
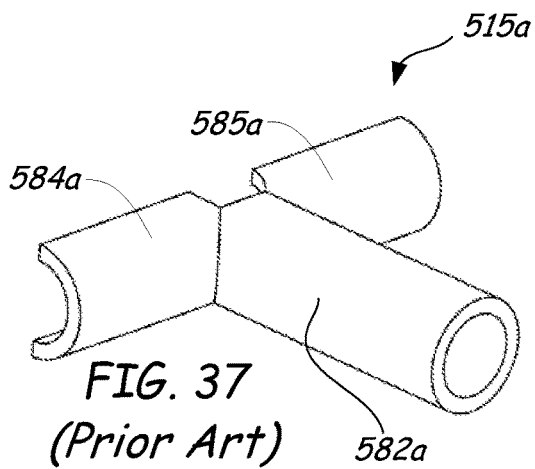
FIG. 37 illustrates a related art ventilation tube having specific features that coordinate with an insertion system, such as the insertion systems illustrated in FIGS. 2 and 3.

FIG. 37 illustrates another exemplary tube style commonly referred to as a T-tube, while FIGS.—38-41 illustrate T-tubes type tubes according to various embodiments of the disclosure. FIG. 37 illustrates exemplary prior art T-tube type ventilation tube 515a, which is commercially available through many ventilation tube manufacturers including, but not limited to Summit Medical, Inc. of St. Paul, Minnesota T-tube 515a includes a hollow main body 582a having a pair of medial flanges 584a and 585a that are to be located internal to the TM (TM) of a patient.

Figure 38:
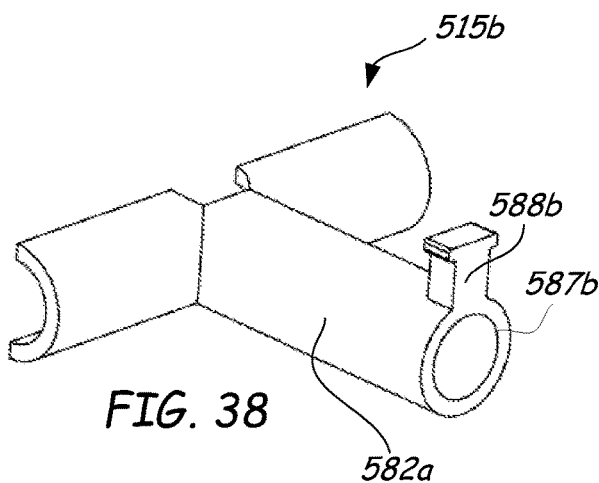
FIGS. 38-43 illustrate still further embodiments of ventilation tubes that coordinate with an insertion system, such as the insertion systems illustrated in FIGS. 2-5.

FIGS.—38-41 illustrate modifications similar in intended function as those shown for grommet style tubes. FIG. 38 shows a T-tube style ventilation tube 515b with a visualization tab 588b located at and extending from lateral end 587b according to one embodiment. Visualization tab 588b is intended to interface with a slot in the cutting sheath component of insertion system 200. In this embodiment, the visualization tab 588b protrudes radially from the hollow main body 582a of ventilation tube 515b (i.e., substantially perpendicular to an axial direction of the tube), but it should be understood that visualization tab 588b could be oriented at any angle to the axis of the hollow main body of the tube. In addition, visualization tab 588b may be located at the lateral end or anywhere along the length of the hollow main body of the tube.

Figure 39:
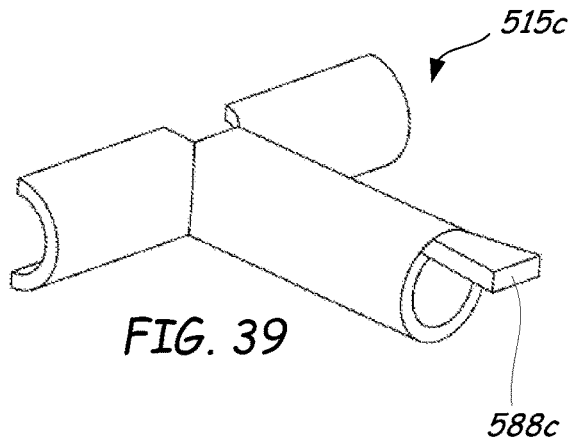
Figure 40:
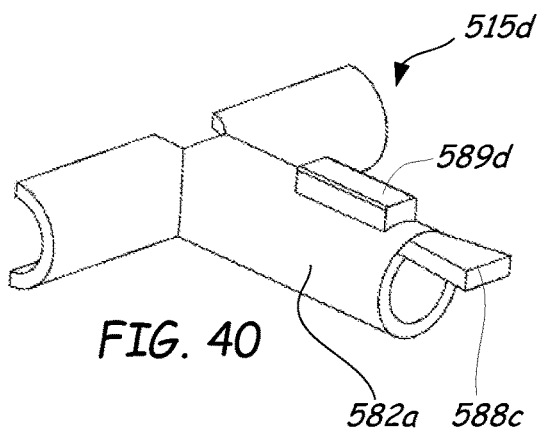

FIG. 39 illustrates another embodiment where the tab intended to interface with a sheath in a sheath element of an insertion device is oriented along or parallel to the main axis of the main body of the ventilation tube. In this embodiment, visualization tab 588c would need to be deformed outward during or after insertion into the sheath so that it would extend radially outward to provide a visual indicator of depth or a physical stop. FIG. 5D illustrates another embodiment with an axially aligned visualization tab 588c and a radially located visualization tab 589d. In this embodiment, the axially aligned visualization tab 588c could be bent or positioned through a slot in the cutting sheath to provide a physical or visual stop. The radially located visualization tab 589d located along hollow main body 582a could additionally register the tube with the slot in the cutting sheath. Furthermore, tab 589d could provide longitudinal strength to hollow main body 582a to prevent the tube from collapsing along its longitudinal axis when the cutting sheath is retracted. In FIG. 5D, the radial tab is located along a portion of the hollow main body of the ventilation tube that would normally be located lateral to the TM, but the visualization tab 589d could extend along the full length of the hollow main body 582a, along the portion normally located behind the TM, or along any other portion thereof.

Figure 41:
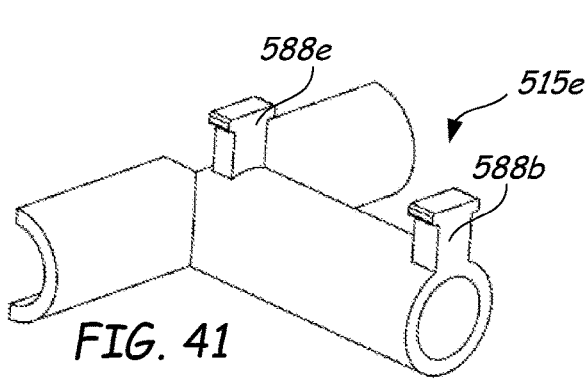

FIG. 41 illustrates a tube 515e with two visualization tabs 588c and 588d shaped to interface with a slot on a cutting sheath of insertion system 200. In instances where the pair of medial flanges are longer compared to the hollow main body of the tube, or in cases where the hollow main body of the tube itself is elongated, having two visualization tabs that extend through a slot on a cutting sheath may be desirable. For example, tube 515e could be inserted so that the medial visualization tab 588d is located just outside the TM, which would ensure that the pair of medial flanges would be located past the TM for correct deployment. The lateral visualization tab 588b could then be used to verify that the tube was fully deployed from the cutting sheath of insertion system 200. In addition, a single tab or registration feature extending along the outside of a ventilation tube and intended to interface with a cutting sheath of an insertion system could be located to provide the same functionality as a number of tabs in indicating correct device positioning with the TM during insertion.

Figure 42:
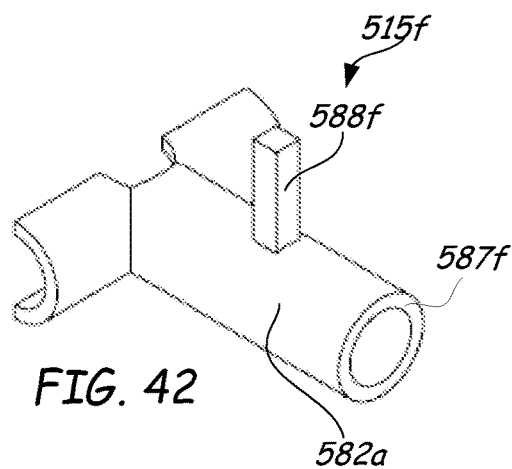
Figure 43:
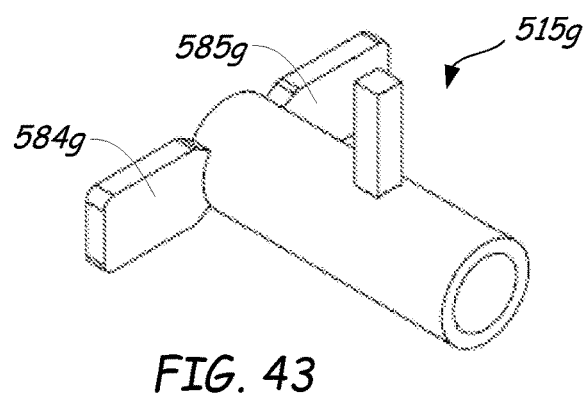

FIG. 42 illustrates a tube 515f having a lateral flange or visualization tab 588f. Tube 515f is similar to tube 515b, however, visualization tab 588f is not located at a lateral end 587f of hollow main body 582a, but along the length of hollow main body 582a. As shown, hollow main body 582a extends past visualization tab 588f. In one embodiment, the extended length ensures that the tube does not fall inside the TM, even if the device is inserted too far through the TM. FIG. 43 illustrates a tube 515g. Tube 515g is similar to tube 515f, however, rather than tube 515g having a pair of medial flanges that are curved as is shown in FIGS. 37-42, tube 515g has a pair of medial flanges 584f and 585f that are flat. Flat medial flanges 584f and 585f are one example of a geometry that provides less frictional forces inside a cutting sheath and make deployment easier.

Figures 44, 45:
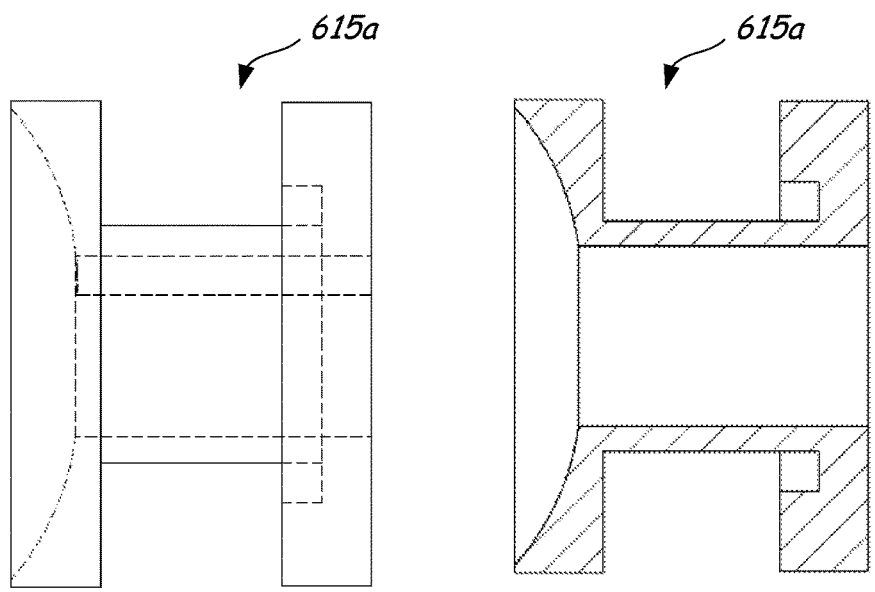
FIGS. 44-47 illustrate embodiments of ventilation tubes comprising medial and lateral flanges with various wall thicknesses.

FIGS. 44-47 illustrate ventilation tubes and corresponding cross sections exhibiting variations in flange thickness and hollow main body thickness. FIG. 44 illustrates a side view of a ventilation tube 615a and FIG. 45 illustrates a section view of ventilation tube 615a. Tube 615a includes a hollow main body and parallel flanges that are of the same outer diameter, but one flange is thinner where it joins the main body than the other. Such a construction could allow for easier deformation and improved folding of the thinner flange during loading and retention in a cutting sheath of an insertion system. In addition, FIGS. 44 and 45 also show a flange that has variable radial thickness (i.e., a flange that is thinner near the hollow main body of the tube and thicker near the outer radius of the flange). The thinner flange section near the hollow main body improves bending or deforming of the tube for loading into a cutting sheath, while the thicker outer edge retains sufficient physical properties to allow the flange to return to its pre-deformed shape upon deployment from the sheath.

Figure 46:
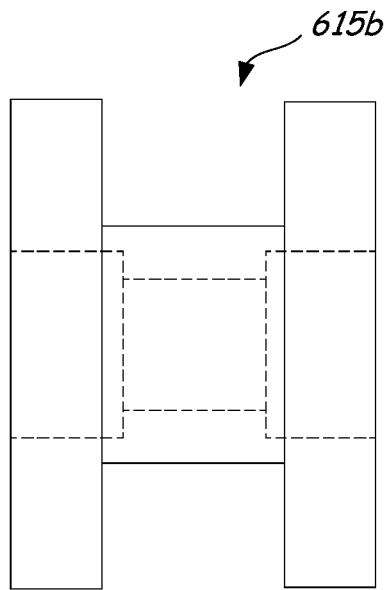
Figure 47:
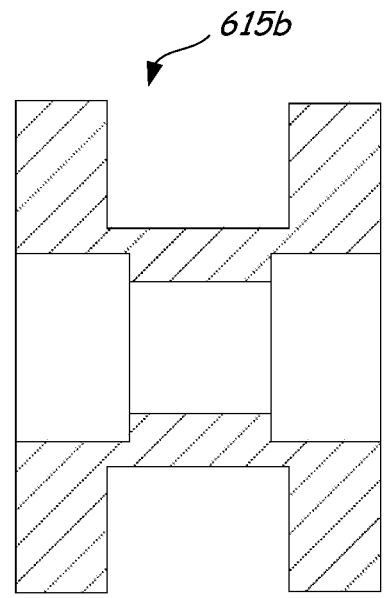

FIG. 46 illustrates a side view of a ventilation tube 615b and FIG. 47 illustrates a section view of ventilation tube 615b. Tube 615b includes parallel flanges that are of the same outer diameter and a hollow main body there between. In FIGS. 46 and 47, the thickness of the hollow main body varies along the tube's axial length. Shown is a thin section of the body located near both the lateral and medial flanges which would improve the bending and deformation of the tube at those points for insertion into a sheath element. It should be noted that the thin section could be at just one end or the other, or if a flange was not fully circumferential, the thin section of the body could be limited to a portion of the circumference of the body. The ability to maintain thicker body sections while providing thinner sections allows the tube to be easily deformed for insertion into a sheath, but still include the necessary axial stiffness to maintain axial length during deployment (i.e. not compressed longitudinally when deployed from a cutting sheath).

Figure 48:
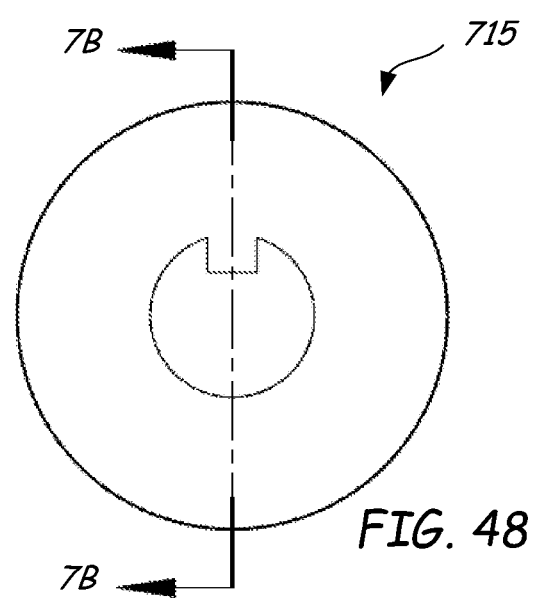
FIGS. 48-49 illustrate embodiments of ventilation tubes comprising main bodies with varying wall thickness.
Figure 49:
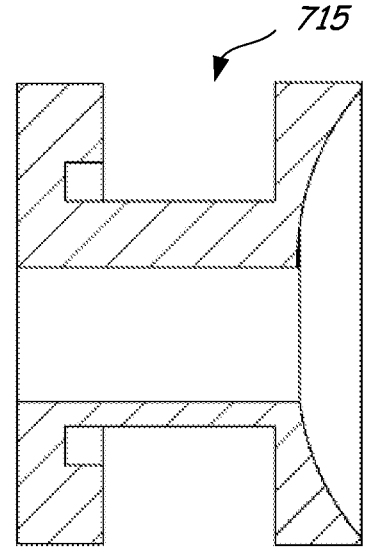

FIG. 48 illustrates an end view of a ventilation tube 715 and FIG. 49 illustrates a section view of ventilation tube 715. Tube 715 includes a thicker portion of the hollow main body running the entire axial length of the tube. This construction allows for a tube that has structural stiffness in an axial direction while providing greater flexibility for compression and folding of the flanges for insertion into a sheath element.

Figure 50:
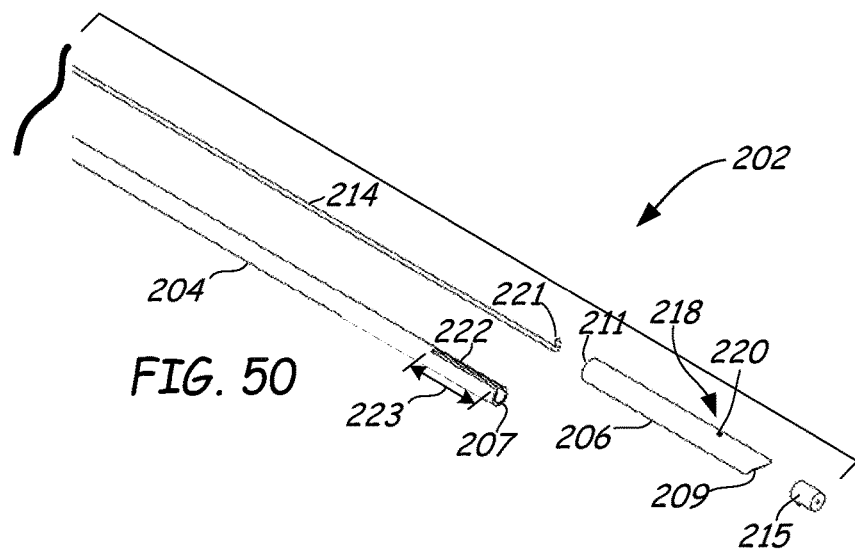
FIG. 50 illustrates an exploded view of the insertion end of the insertion system illustrated in FIGS. 2 and 3.
Figure 51:
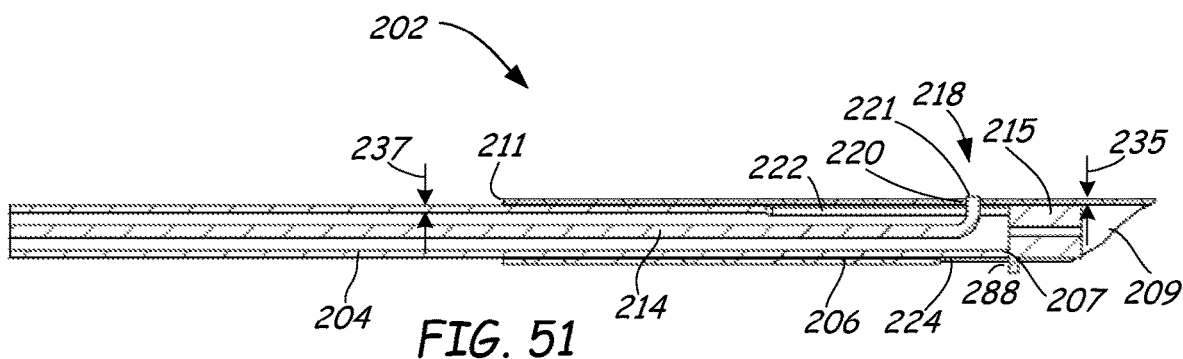
FIGS. 51-52 illustrate various section views of various embodiments of the insertion end illustrated in FIG. 50.

With reference back to insertion systems 200 and 200', FIG. 50 is a partial exploded view of insertion end 202 of insertion system 200 and FIG. 51 is an enlarged sectional view of insertion end 202 of insertion system 200. Although FIGS. 50 and 51 refer back to insertion system 200, it should be understood that FIGS. 50 and 51 also represent the same components in insertion system 200'. Cutting sheath 206 surrounds a distal portion of positioning rod 204 including a distal end 207 and is configured to receive a ventilation tube 215 constrained within the boundaries of cutting sheath 206. Positioning rod 204 is a hollow body that attaches to handle 212 through nose 213, bends along an angle 216 and, in one embodiment, includes a slot or channel 222 in the distal portion. Actuation member 214 can be made of a flexible material, such as but not limited to plastic or thin metal wire, and runs from a portion of an actuation mechanism including rotatable actuating element 210 housed within handle 212, extends through and/or down the inside of positioning rod 204 and cutting sheath 206 and is fixedly attached to cutting sheath 206 at an attachment area 218. In alternative embodiments, the connection between actuation member 214 and cutting sheath 206 can be a removable connection.

Cutting sheath 206 includes an aperture 220 that extends entirely through a thickness 235 of a wall of cutting sheath 206. Aperture 220 allows actuation member 214 to transition from an area internal to cutting sheath 206 to an area external to cutting sheath 206. Aperture 220 also defines attachment area 218 by providing access to form a joint between actuation member 214 and cutting sheath 206, making it possible to weld or otherwise bond actuation member 214 to cutting sheath 206. In one embodiment, a distal end 221 of actuation member 214 is welded to aperture 220 to fixedly attach it to cutting sheath 206. For example, distal end 221 of actuation member 214 can be plug welded to aperture 220. In this embodiment, slot 224, which allows for the protrusion of a tab or visualization tab (such as those visualization tabs discussed in FIGS. 3-7), can also be used to allow access to the plug weld that attaches actuation member 214 to aperture 220 in cutting sheath 206.

Figure 52:
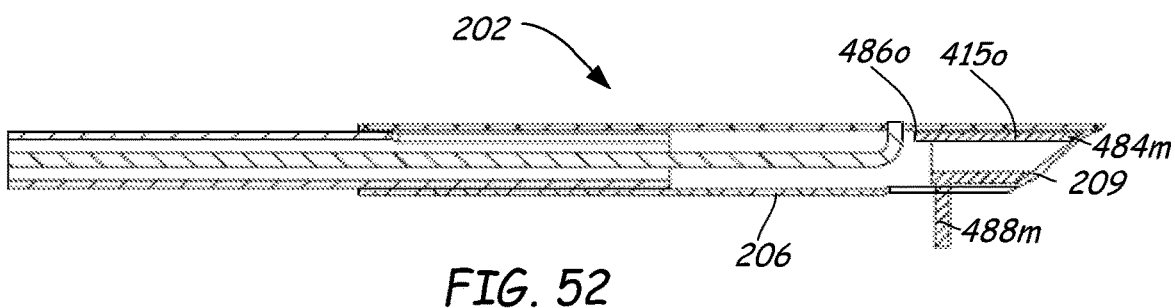

FIG. 52 is similar to FIG. 51, however, rather than ventilation tube 215 being loaded into cutting sheath 206, in FIG. 52, ventilation tube 415o is loaded into cutting sheath 206. In FIG. 52, lateral tab 486o is folded back and visualization tab 488m protrudes through slot 488m. Since tube 415o includes a medial flange 484m that is tapered like the beveled distal edge 209 of cutting sheath 206, tube 415o can be placed closer to distal edge 209 than tube 215, which minimizes the insertion depth required to deploy behind the TM. Minimizing insertion depth is better in situations where the TM is retracted.

Figure 53:
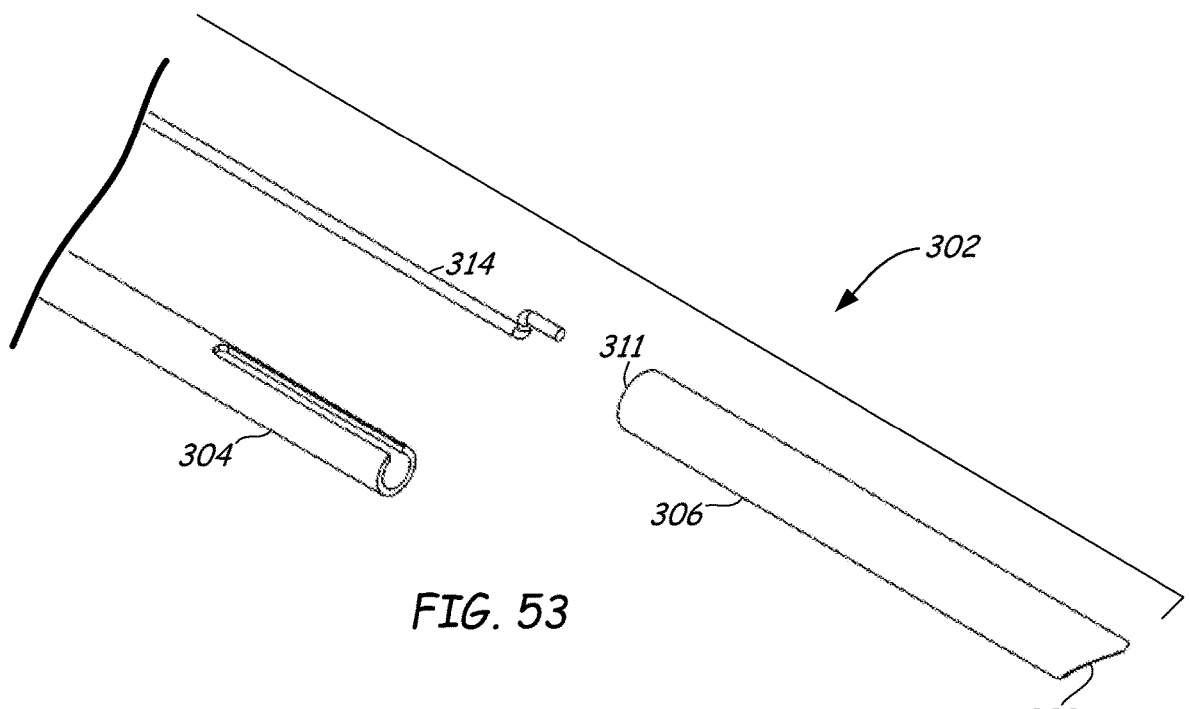
FIG. 53 illustrates an exploded view of an alternative embodiment of an insertion end.
Figure 54:
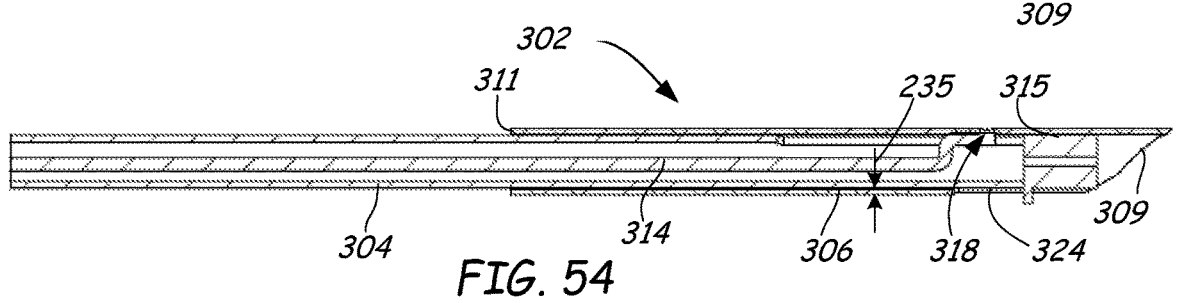
FIG. 54 illustrates a section view of the insertion end illustrated in FIG. 53.

In another embodiment and as illustrated in FIG. 53, which is a partial exploded view of an alternative insertion end 302 of insertion system 200, and in FIG. 54, which is an enlarged sectional view of insertion end 302, it is possible to attach an actuation member 314 to a cutting sheath 306 at an attachment area 318 by allowing access to the attachment area utilizing a slot 324 that extends entirely through the thickness 235 of a wall of cutting sheath 306 that is located opposite of where aperture 220 in cutting sheath 206 is located. Slot 324 spans a length from a distal end or cutting edge 309 of cutting sheath 306 to a termination area and can be used to pass appropriate instruments through the wall of cutting sheath 306 for joining actuation member 314 to an internal wall of cutting sheath 306. For example, actuation member 314 can be joined to cutting sheath 306 by welding or otherwise bonding. In this embodiment, an aperture, such as aperture 220 of insertion end 202, is not needed. Both insertion end 202 and 302 already include slot 224 or 324 to allow for the protrusion of a tab or visualization tab (such as those visualization tabs discussed in FIGS. 6-49) of ventilation tube 215 or 315. In still another embodiment, a different slot could extend entirely through the thickness of a wall of cutting sheath 306, but spans a length from a proximal end 311 to a terminating area of cutting sheath 306 for this same purpose.

With reference back to FIGS. 50-52, in addition, actuation member 214 can travel in slot or channel 222 of positioning rod 204. In one embodiment, slot or channel 222 intersects with distal end 207, extends entirely through a thickness 237 of a wall of positioning rod 204 and includes a length 223 that spans from distal end 207 of positioning rod 204 to a terminating area that is surrounded or covered by cutting sheath 206. Ensuring slot 222 is covered by cutting sheath 206 is important in preventing loss of suction when insertion system undergoes a suction functionality. Slot or channel 222 registers cutting sheath 206 to positioning rod 204. In an alternative embodiment, cutting sheath 206 could extend a larger distance from distal end 207 of positioning rod 204 than that which is illustrated in FIG. 9 such that the entire range of motion of actuation member 214 occurs at a point beyond distal end 207 of positioning rod, such that slot or channel 222 is not required.

In still another embodiment and in instances where actuation member 214 does not interface with a slot or channel 222 in positioning rod 204 to provide a means of registration for cutting sheath 206, the geometry of actuation member 214 could provide a means of registration. For example, a round steel wire would limit the degree of rotation that cutting sheath 206 can achieve. In another example, a flat wire or the use of two or more actuation members attached at different locations on cutting sheath 206 could also be employed to reduce the achievable angle of rotation between cutting sheath 206 and positioning rod 204. Because of the bend that actuation member 214 takes as it travels inside the bend area of positioning rod 204, the torsional rigidity of a flat actuation member 214 could be enhanced further to minimize angular displacement of cutting sheath 206 in relation to positioning rod 204. The geometry of actuation member 214 will be further discussed below.

As illustrated in FIGS. 51 and 52, actuation member 214 is attached to aperture 220 of cutting sheath 206 a sufficient distance from a distal end 209 of cutting sheath 206 so as not to interfere with the placement of tube 215 distal to joint 218. In particular, FIGS. 50-52 show actuation member 214 attached closer to distal end or cutting edge 209 of cutting sheath 206 than to proximal end 211 of cutting sheath 206. In embodiments where actuation member 214 travels in slot or channel 222 in positioning rod 204, the location where actuation member 214 is attached to aperture 220 minimizes the length required of channel 222 in positioning rod 204 and improves manufacturability. It should be realized, however, the attachment between the actuation member 214 and cutting sheath 206 can be located anywhere along the internal lumen or wall of cutting sheath 206.

Figure 55:
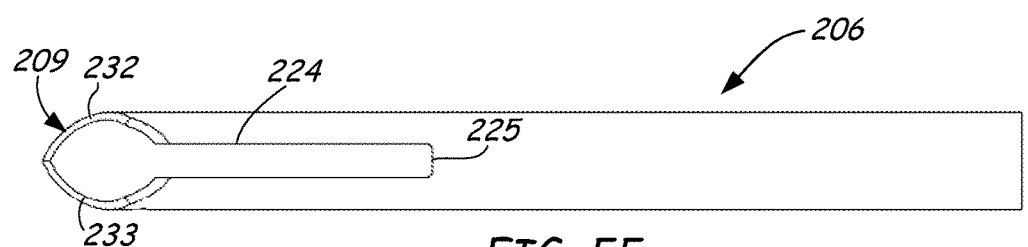
FIG. 55 illustrates a bottom view of the cutting sheath of the insertion system illustrated in FIGS. 2 and 3.
Figure 56:
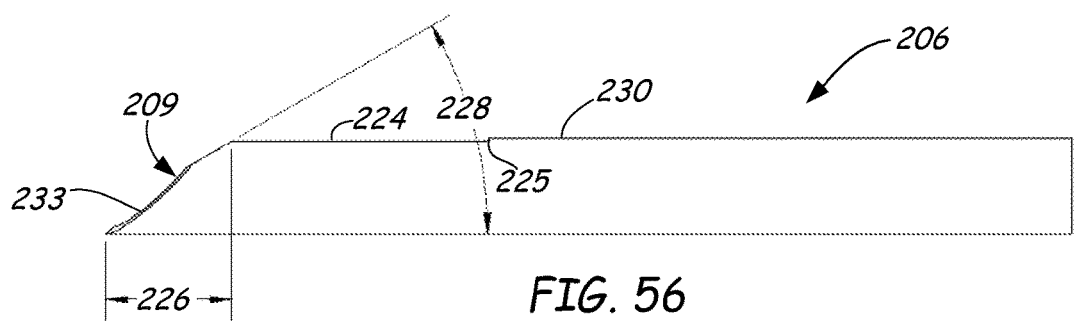
FIG. 56 illustrates a side view of the cutting sheath illustrated in FIG. 55.

FIG. 55 illustrates a bottom view of cutting sheath 206 and FIG. 56 illustrates a side view of cutting sheath 206 according to one embodiment. FIGS. 55 and 56 illustrate cutting sheath 206 with a sharpened, beveled distal end or cutting edge 209 and a slot 224 extending from the sharpened, beveled distal end or cutting edge 209 to a terminating end 225. In one embodiment, the overall length 226 of beveled end 209 is minimized, as this portion must extend past the tympanic membrane into the constrained space of the middle ear during ventilation tube placement and not interfere with the highly sensitive bones and organs in the middle ear. To minimize length 226, beveled end 209 includes a primary bevel angle 228 that is relative to a wall 230 of cutting sheath 206. For example, primary bevel angle 228 can range between approximately 30 degrees and 40 degrees.

Additional grinding steps can be taken to enhance the cutting ability, or sharpness, of beveled distal end or cutting edge 209. As illustrated in FIGS. 55 and 56, at least one set of lancet grinds are used to produce lancet edges 232 and 233. The lancet grinding step is capable of removing additional overall length from the beveled area, which further shortens the portion of the cutting sheath that must extend into the middle ear during ventilation tube placement. In one exemplary embodiment, beveled length 226 of a 15 gauge cutting sheath (outer diameter of 0.072 in. or 1.829 mm) with a 30 degree primary bevel in combination with secondary lancet grinds can be less than 0.10 in. or 2.54 mm. In another exemplary embodiment, beveled length 226 of a 15 gauge cutting sheath (outer diameter of 0.072 in. or 1.83 mm) with a 40 degree primary bevel in combination with secondary lancet grinds can be less than 0.075 in. or 1.905 mm.

In cases where the TM is already perforated or an incision is made with another instrument or when there is insufficient room behind the TM (i.e., severe TM retraction), cutting sheath 206 can include a minimal bevel or no bevel. For example, cutting sheath 206 could be made with an approximate 70 degree bevel and can be combined with a tube having little or no bevel on the medial flange.

A lancet grind, or comparable sharpening procedure which produces cutting edges located along the outer diameter of the cutting sheath are preferred when a ventilation tube is loaded into the cutting sheath 206 by inserting it axially from the distal end or cutting edge 209 of the cutting sheath 206. Sharp edges on the inner diameter of the cutting sheath 206, such as those achieved with a back-grind style of sharpening, tend to catch or cut the tube during such a loading process. Methods of loading a ventilation tube into cutting sheath 206 will be discussed in detail below.

Cutting sheath 206 can be made of thin walled stainless steel tubing having a wall thickness 235. However, other thin-walled metallic tubing can also be suitable. For example, 15 gauge thin-walled tubing (having 0.006 in. or 0.153 mm thick wall) provides sufficient rigidity to constrain ventilation tube 215 in a compressed configuration. In addition, wall thickness 235 provides sufficient material to sharpen into a cutting edge 209.

One important feature of cutting sheath 206 (and also positioning rod 204) is the surface finish. The insertion system 200 can be operated under direct visualization by the user which requires sufficient lighting. In one embodiment, when used with an otoscope, operating microscope, or fiber optic scope, a non-reflective surface finish can reduce the glare off cutting sheath 206 and positioning rod 204, which would hinder visualization. A non-glare surface finish can be achieved by abrasive blasting of the parts, surface passivation, oxidation, or other suitable surface treatment, which reduce or eliminate the reflective properties of materials of cutting sheath 206 and positioning rod 204. In another embodiment, the inner diameter of cutting sheath 206 and/or the outer diameter of positioning rod 204 could be treated with a lubricious coating, such as PTFE, to reduce the friction between the two sliding surfaces during sheath retraction while also providing a non-glare surface.

The slot 224 illustrated in FIGS. 9 and 12 allows a tab or visualization tab 288 of ventilation tube 215 to be visible, or for a tab or visualization tab 288 of ventilation tube 215 to extend outward through cutting sheath 206 to provide a physical or visual indication of tube 215 location for proper placement through the TM. As illustrated in FIGS. 7 and 8, slot 224 extends from distal end or cutting edge 209 to terminating end 225 and is substantially straight.

However, slot 224 is not limited to the configuration illustrated in FIG. 55. FIG. 57 illustrates a bottom view of another embodiment of a cutting sheath 406, slot 424 can have a spiral twist, which could be used to impart a spin on a ventilation tube, such as ventilation tube 215, to improve deployment across the TM. A slot 424 having a twist, or other non-straight geometry could also be used to position a tab on the ventilation tube, such as visualization tab 288 of ventilation tube 215, closer to the longest edge of the cutting sheath (i.e., opposite where the slot 424 intersects with distal end or cutting edge 409) to allow a user to more easily visualize both the tab on the ventilation tube and the longest edge of cutting edge 209 during use. Slot 424 can be formed using a helix that has a pitch ranging between 0.5 inches (12.7 mm) and 1.5 inches (35.1 mm). However, slot 424 can also be a simple curve.

FIG. 57 also illustrates cutting sheath 406 with an unsharpened cutting edge or distal end 409, which allows an insertion system, to be used to insert a ventilation tube into a pre-existing incision in the TM. A primary bevel of between approximately 40 and 60 degrees minimizes the length of cutting sheath 406 that must be inserted into the middle ear to properly position the ventilation tube across the TM. Since cutting sheath 406 doesn't require sharpening, cutting sheath 406 could be manufactured from plastic, such as PEEK, acrylic, poliamide, or suitable alternatives, and could be clear or translucent to allow the user to visualize the ventilation tube loaded in cutting sheath 406. In addition, a light source internal to the positioning rod, for example a fiber optic light source, could be used to illuminate a clear sheath from the inside, thus allowing a tertiary means of determining tube location within the sheath to aid in placement in the TM at the correct depth.

FIG. 58 illustrates a bottom view of yet another embodiment of a cutting sheath 506 with a modified geometry where slot 524 meets sharpened distal end or cutting edge 509. This modified geometry can be achieved during the forming of slot 524, or during the sharpening process. Beveling, or softening the corners 536 where slot 524 meets the sharpened beveled face 538 of cutting sheath 506 solves two problems. First, it reduces the chances of tearing the TM or accidental 'coring' out of a section of the TM and second, it improves the loadability of ventilation tubes if those tubes are inserted into the distal end 509 of the tube. Sharp corners or points created by slot 524 that is cut straight into the beveled end of the sheath can catch, cut, or tear silicone ventilation tubes during loading if not beveled or softened.

FIGS. 59-64 illustrate different embodiments of a cutting sheath with a visual indicator or physical stop so as to provide the user with the ability to determine depth of penetration through the TM relative to the bevel located on the distal end of the cutting sheath. In FIGS. 59 and 60 (where FIG. 59 illustrates a perspective view and FIG. 60 illustrates a side view), a visual indicator 1445 extends outward from cutting sheath 1406 approximately 180 degrees from the top of cutting sheath 1406 and opposite a slot (not illustrated), which is located at a bottom of cutting sheath 1406. In addition, visual indicator 1445 is positioned at the substantially same distance as the distance of the proximal end of the beveled portion (i.e., where the bevel portion begins) of cutting sheath 1406. Visual indicator 1445 allows a user to visually determine the degree of bevel penetration through the TM without being able to see the actual beveled portion of cutting sheath 1406. Visual indicator 1445 could also provide tactile feedback that the correct penetration depth has been achieved by stopping further advancement of the sheath manually through the TM. In FIGS. 61 and 62 (where FIG. 61 illustrates a perspective view and FIG. 62 illustrates a side view), a visual indicator 1545, which encompasses all or a portion of the outer circumference of cutting sheath 1506 and which is located such that visual or physical proximity to the TM indicates that a correct depth of penetration has been achieved such that the entire beveled portion of the sheath has penetrated the TM. FIGS. 63 and 64 (where FIG. 63 illustrates a perspective view and FIG. 64 illustrates a side view) illustrates visual marker bands 1645 that may span all or a portion of the circumference of cutting sheath 1606 such that the user can visually determine the locations of the beveled portion of the sheath or the proximal end of the ventilation tube, or both, from any viewing angle along the positioning rod and sheath. In one embodiment, two visual marker bands can be used to provide a range of acceptable TM locations (e.g., a max/min type indicator). Still further, the cutting sheath, the positioning rod or both can be designed or constructed from materials that have echogenic properties, making it easier to visualize their location using ultrasound in cases where visualization by physical means is not feasible or is not sufficient.

FIG. 65 illustrates an enlarged view of an insertion end 1702 including one embodiment of a visual indicator or physical stop 1745 provided by a cutting sheath or other element 1751 (as is illustrated in FIG. 65) positioned on the outside or over cutting sheath 1706. As shown, cutting sheath 1706 attaches to positioning rod 1704 (shown in phantom) such that the distal end of element 1751 and visual indicator 1745 are located at the same location as the proximal end of the beveled portion of cutting sheath 1706. In the embodiment, element 1751 is a circumferential sheath of which a portion is cut away to maintain visibility of visual indicator 1745 and of a tab 1788 on ventilation tube 1715, which extends through the slot in cutting sheath 1706. Additionally, the attachment point of the circumferential sheath 1751 to cutting sheath 1706 is positioned such that the necessary coaxial motion of cutting sheath along positioning rod 1704 is not impeded by circumferential sheath 1751. Circumferential sheath 1751 could also extend over the complete length of positioning rod 1704 and be attached to the handle assembly or nose of the nose assembly. The same functionality as the functionality of circumferential sheath 1751 could be achieved with other elements, such as wires or partial sheaths which would extend along the sheath element to the beginning of the beveled portion of the cutting sheath.

FIG. 66 illustrates a side view and FIG. 67 illustrates a bottom view of cutting sheath 1806 with a sensing element 1853 for detecting when the cutting sheath has penetrated sufficiently through the TM to allow for tube deployment. Inserting cutting sheath 1806 through the TM far enough so that the lateral flange of the ventilation tube is past the TM at the shallowest point of penetration ensures successful tube placement. Because of the bevel on cutting sheath 1806, a heel 1855 of the bevel will be the point where minimum penetration occurs, and as such, sensing when this point or a point just past this on the cutting sheath is in contact with the TM would allow the user to detect correct depth of penetration for tube deployment. A mechanical sensor to detect the physical resistance created by direct contact with the TM, or an electrical sensor to detect a change in electrical resistance via contact with the TM can be employed. It should be understood that any sensing means capable of detecting contact or proximity could be used. Upon detection of a correct depth of penetration, the insertion device could generate a signal, such as an audible tone, to indicate to the user that tube deployment can be performed. In another embodiment, the insertion device may detect a correct depth of penetration through the TM and automatically retract the cutting sheath thereby deploying the tube and limiting an further penetration into the middle ear. In this embodiment, the user manually advances the device through the TM until the sheath retracts automatically, and then applies suction if necessary or removes the device from the ear canal.

Figure 68:
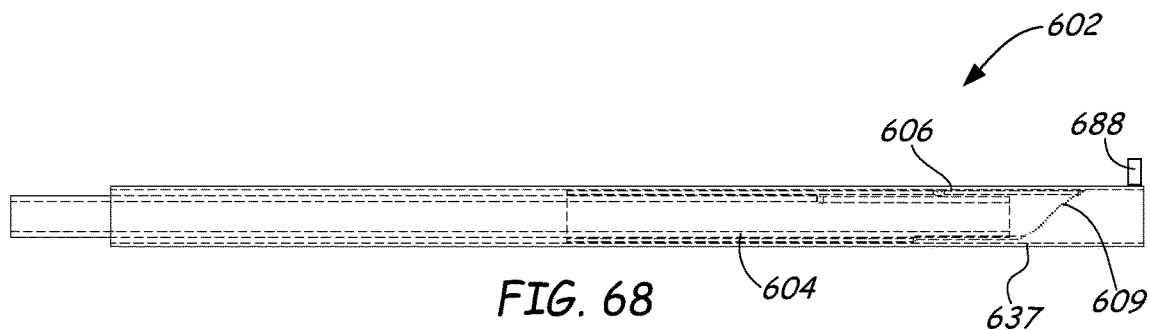
FIG. 68 illustrates another embodiment of an insertion end including a passive safety sheath located over a cutting sheath.

FIG. 68 illustrates a side view of another embodiment of an insertion end 602. In FIG. 68, a passive safety sheath 637 is located over the cutting sheath 606 (shown in phantom). Safety sheath 637 can be held in place by friction, and manually removed by the user immediately before use. This safety sheath 637 protects the cutting edge 609 during shipping, and protects the clinician from inadvertent needle sticks or cuts prior to use. Alternatively, safety sheath 637 can be manually retracted by the user immediately before use, exposing the cutting edge 609 but remaining in place around positioning rod 604. After deploying a ventilation tube across the TM, safety sheath 637 could then be moved back into its original position around cutting sheath 606, again protecting users from inadvertent needle sticks.

Figure 69:
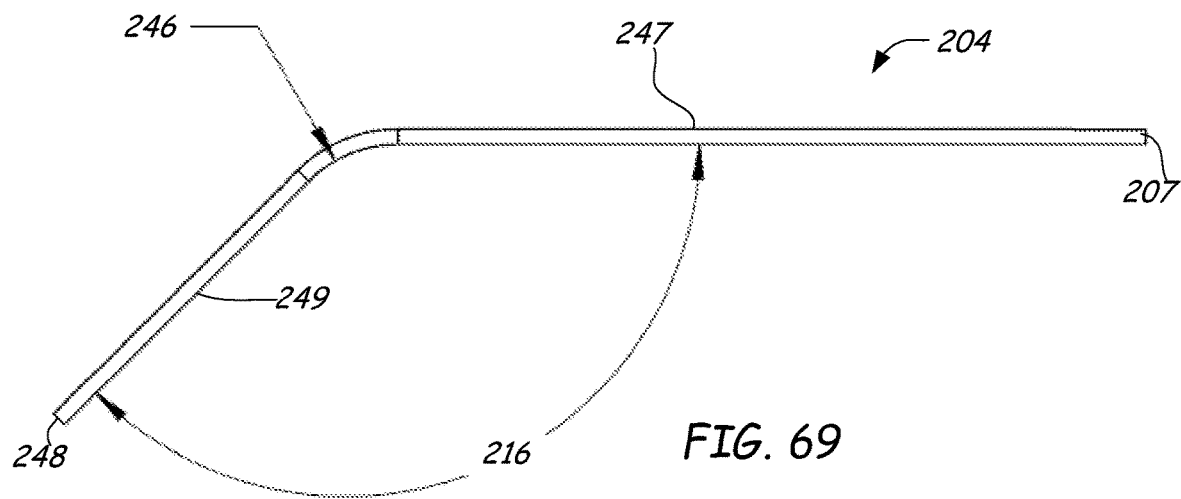
FIG. 69 illustrates a side view of the positioning rod illustrated in FIGS. 2 and 3.

FIG. 69 illustrates a side view of positioning rod 204. Positioning rod 204 is a continuous hollow body including a bend 246 having an angle 216 that divides positioning rod 204 into a first leg 247 and a second leg 249. First leg 247 is greater in length than second leg 249 and includes distal end 207, which is configured to abut against a ventilation tube when loaded in insertion system 200 and when being deployed. A proximal end 248 of second leg 249 engages with nose 213 (FIG. 2) of insertion system 200. The length of the short leg 249 extends through nose piece 250 and between approximately 0.5 and 1.5 inches (i.e., 12.7 and 38.1 mm). The function of short leg 249 is to move longer leg 247 sufficiently far enough away from where nose 213 connects to handle 212 (FIG. 2) to allow the user to maintain sight lines straight down leg 247. The shorter leg 249 ensures that the user does not block these sight lines with their fingers while grasping the front of handle 212. The length of longer leg 247 is between approximately 50 and 100 mm. More particularly, leg 247 is approximately 60-65 mm. This length is sufficient to allow cutting sheath 206 to reach deep enough into the ear canal and the middle ear for a ventilation tube to be positioned and deployed across the TM. The radius of the bend 246 in positioning rod 204 can range between approximately 0.25 and 2 inches (i.e., 6.35 and 50.8 mm). More particularly, the radius of bend 246 can be between approximately 0.4 and 0.8 inches (i.e., 10.16 and 20.32 mm). The bend 246 in positioning rod 204 should be minimized so that the radius portion does not interfere with the a speculum (which will be discussed in detail below) or other interfacing accessories, while being kept large enough such that it allows the sliding of the actuation member 214 along its inner lumen without imposing excessive frictional restraining forces. In a spring-loaded design, where a spring is chosen to set the resistive force, a large radius for the positioning rod to minimize resistance could be used.

FIGS. 70-73 illustrate enlarged views of various embodiments of a distal end of a positioning rod. FIG. 70 illustrates an enlarged view of distal end 207 of positioning rod 204. Positioning rod 204 includes a straight slot or channel 222 formed into positioning rod 204 and intersecting with distal end 207 and extending to a terminating area 239. As previously described, channel 222 provides a passage for actuation member 214 to transition from the inside of positioning rod 204 to an attachment point on the corresponding cutting sheath 206. In addition, a length 223 of channel 222 provides a range of motion for actuation member 214, and can limit the maximum range of motion of cutting sheath 206. Furthermore, channel 222 registers cutting sheath 206 to positioning rod 204. In particular, the angular orientation of cutting sheath 206 is registered relative to positioning rod 204.

FIG. 71 is an enlarged view of an alternative embodiment of a distal end of a positioning rod. Like channel 222, a channel 722 formed in a positioning rod 704 is straight. However, rather than channel 722 intersecting with distal end 207, as is the case in FIG. 70, channel 722 extends from a distal area 741 that does not intersect with distal end 707 to a terminating area 739. The embodiment illustrated in FIG. 71 provides a full circular contact area at the end of positioning rod 704 for positioning against a ventilation tube when a cutting sheath is being retracted during deployment of a ventilation tube.

FIG. 72 is an enlarged view of another alternative embodiment of a distal end of a positioning rod. FIG. 72 illustrates an embodiment where channel 822 includes a straight portion 842 and a j-shaped portion 843. Like channel 222, straight portion 842 of channel 822 intersects with distal end 807 and extends to a terminating area 839. J-shaped portion 843, however, extends as an arcuate slot from terminating area 839 to arcuate end 844. J-shaped portion 843 is configured to capture the actuation member after a ventilation tube is deployed, and preventing the cutting sheath from being displaced forward again towards the TM. In cases where the cutting sheath is retracted sufficiently such that the cutting edge is positioned directly over positioning rod 804 and proximal to distal end 807, positioning rod 804 acts as a safety mechanism which protects the cutting edge of the cutting sheath to prevent accidental needle sticks. Additionally, because positioning rod 804 cannot be returned to a pre-use state, the embodiment illustrated in FIG. 72 can also prevent the re-use of an insertion end when the insertion end is intended to be a single-use device. While a J-shaped portion 843 of channel 822 is shown, other geometries which achieve the same functionality are also considered.

For example, FIG. 73 illustrates an enlarged view of an embodiment where channel 922 of a positioning rod 904 intersects with distal end 907 of positioning rod 904 and extending to a terminating area 939. Unlike channels 222, 722 and 822, channel 922 includes a helical or curved pathway. The helical or curved pathway of channel 922 aids in inserting a ventilation tube into an insertion end by slightly rotating the cutting sheath as it is retracted along positioning rod 904. A helical pathway can be formed using a helix that has a pitch between approximately 0.5 inches (12.7 mm) and 1.5 inches (38.7 mm). It should be understood that any combination of the preceding elements described in FIGS. 70-73 regarding channels in a positioning rod can be used.

FIGS. 74-75 illustrate perspective views of various embodiments of positioning rods that include an interface for receiving an attachment of or positioning of other devices alongside it such that the user can move and position an attached device and the positioning rod with a single hand. The embodiment illustrated in FIG. 74 shows a positioning rod 1004 having a clip 1052 located on the outer surface of the longer leg 1047. For example, clip 1052 can receive a fiber optic scope, a fiber optic light source, drug delivery tubes, devices, or an atomizer or other type of peripheral attachment for enhancing the capabilities of the insertion system. The embodiment illustrated in FIG. 75 shows a positioning rod 1104 having a protuberance 1152 located on the outer surface of the longer leg 1147. For example, protuberance 1153 can interface with a speculum (which will be discussed in detail below) or other interfacing accessories.

FIG. 76 illustrates an end view of insertion end 202 (with nose 213 removed) illustrating the relationship between cutting sheath 206 and positioning rod 204 in a first position or a position A. As illustrated in FIGS. 50-52 and 55-56 cutting sheath 206 is beveled and therefore has one side that is longer in axial length than the other. In addition, slot 224 is cut along one side of cutting sheath 206. In one embodiment, slot 224 is formed along the shorter axial length side rather than the longer axial length side of cutting sheath 206. Because of these features, cutting sheath 206 can be oriented in different angular relationships to the bend 246 in positioning rod 204. In one embodiment, the long edge, or the leading point of cutting sheath 206 is located along the top of bend 246 and slot 224 is located along the bottom of bend 246 as shown in FIG. 76. However, the long edge and therefore slot 224 on the sheath could be located at various angular relations to the bend 246 in positioning rod 204 to improve visualization under different scenarios. For example, the long edge of cutting sheath 206 could be positioned approximately 180 degrees from the top of the bend 246 of positioning rod 204 as indicated by a second position or a position B, or at any angle in between, such as approximately 45 degrees as indicated by a third position or a position C or approximately 90 degrees as indicated by a fourth position or a position D.

As previously discussed and with reference back to FIG. 50, actuation member 214 of insertion system 200 passes through channel 222 in positioning rod 204 to attach to cutting sheath 206. In FIG. 50, actuation member can consist of a round, stainless steel wire with a spring temper or a soft temper that has a diameter of about 0.014 inches or 0.3556 mm. A round cross section allows actuation member 214 to interface with a round plug hole in cutting sheath 206 for ease of manufacturing and for making an attachment such as a weld or a braze between cutting sheath 206 and actuation member 214. The spring temper helps prevent bends from setting during handling, manufacturing and assembly. In the alternative, a smaller diameter actuation member can also be used, such as a diameter of about 0.009 inches or 0.2286 mm, to reduce friction inside the positioning rod. By keeping actuation member 214 consistently straight, or with a known bend profile, the frictional force of actuation member 214 contacting the internal lumen of positioning rod 204 is kept consistent and provides for a consistent degree of resistance during cutting sheath 206 retraction. Actuation member 214 can also include a lubricious coating, such as PTFE, to minimize the frictional force of actuation member 214 sliding inside positioning rod 204. In an alternative embodiment, actuation member 214 can consist of flat wire. Flat wire can provide a greater surface area and potentially improved interface geometry where actuation member 214 attaches to cutting sheath 206 or to actuator mechanism 210 in handle 212.

Figure 77:
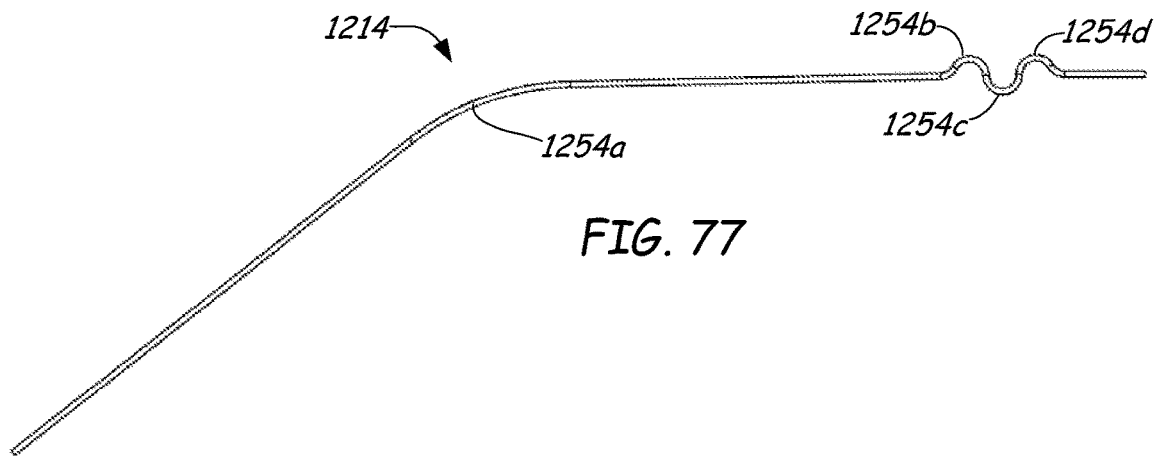
FIG. 77 is a side view of an alternative embodiment of the actuation member of the insertion system illustrated in FIGS. 2 and 3.

FIG. 77 is a side view of an actuation member 1214 that illustrates alternative embodiments to actuation member 214 illustrated in FIG. 50. In one embodiment, actuation member 1214 includes one or more bends 1254 along its length which can increase or decrease the frictional force that actuation member 1214 experiences sliding along the internal lumen of a positioning rod during cutting sheath retraction. Bend 1254a illustrates a bend in a shape closely approximating the bend in a positioning rod, which eliminates most of the friction encountered during initial retraction of the cutting sheath, allowing for an easier start to the retraction process. Bends 1254b, c and d show actuation member 1214 with one or more bends intended to increase the frictional force between actuation member 1214 and a positioning rod. Increasing the force between actuation member 1214 and a positioning rod can be useful for holding the cutting sheath in the retracted position after a ventilation tube has been deployed and preventing unwanted sheath retraction during shipping and handling prior to use. Bends 1254a, b and c can also provide repeatable resistive force during the entire cutting sheath retraction process, and prevent inadvertent 'jumping' of the ventilation tube out of the cutting sheath when the ventilation tube is partially or fully deployed. If the frictional force of the ventilation tube against the inner lumen of the cutting sheath is the governing resistance to sheath retraction, the resisting force will change as the ventilation tube is deployed and the contact surface area is reduced, and may change in a stepwise function as flanges on the ventilation tube are deployed. Using the frictional resistance to motion of the actuation member can moderate this.

It should be noted that in another alternative embodiment, an actuation member could be routed completely outside of the positioning rod rather than partially inside the positioning rod and therefore positioning rod 204 need not be hollow. In such an embodiment, the actuation member exits the handle, such as handle 212, of the insertion system, such as insertion system 200, and travels along the outside of the positioning rod and attaches to a proximal end of the cutting sheath or anywhere along the length of the cutting sheath. Guide tubes or tabs located along the outer diameter of the positioning rod could be used to route and constrain the actuation member. In one embodiment, the actuation member could pass through an aperture or slot in the cutting sheath and protrude into the inner lumen of the positioning rod to thus allow the actuation member to act as a registration mechanism to register the sheath to a slot or aperture located on the positioning rod.

The attachment between an actuation member and a cutting sheath does not need to be permanent. In such an embodiment, the actuation member may include a shorter bent portion on its end that engages reversibly with an aperture in the sheath. A larger bend or 'bow' in the actuation member ensures that the shorter bent portion remains pushed against the inner diameter of the cutting sheath such that at least a portion of the bent section remains engaged with the cutting sheath aperture. This embodiment allows the user to push the actuation member back into or out of the aperture on the cutting sheath, making the cutting sheath removable and/or replaceable. In instances where a bilateral ventilation tube placement is warranted, two cutting sheathes with pre-loaded ventilation tubes could be provided, and the clinician could attach them to a single insertion handle to reduce waste.

Figure 78:
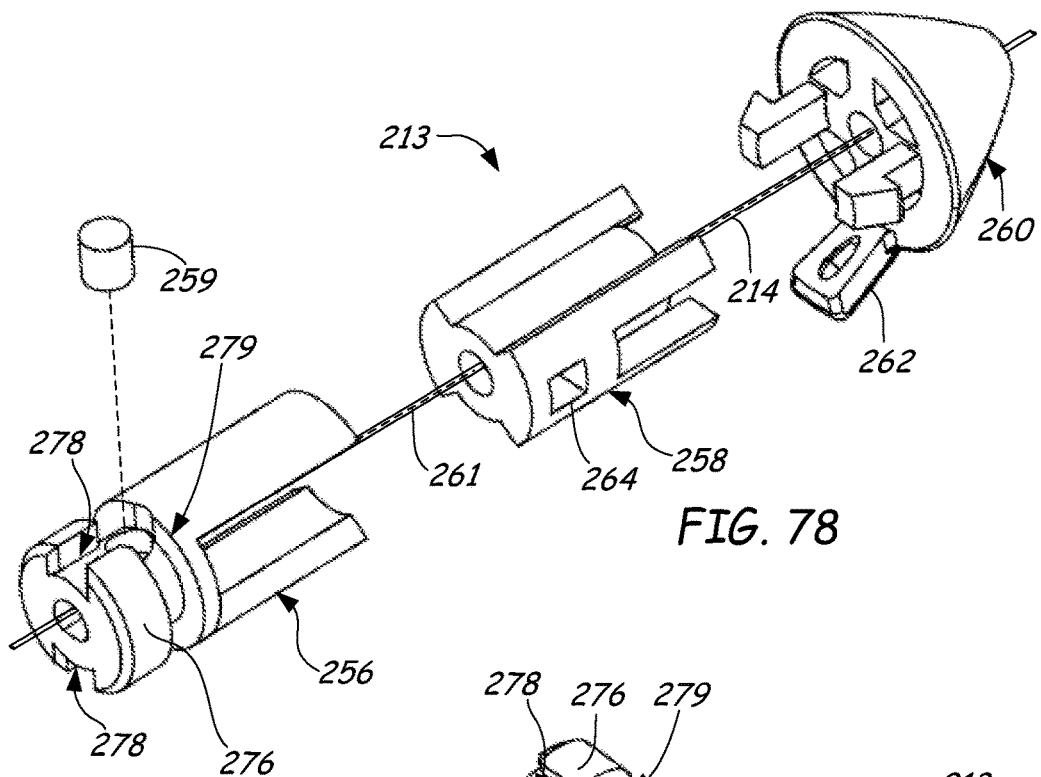
FIG. 78 illustrates an enlarged exploded view of a nose of the nose assembly illustrated in FIGS. 2 and 3.
Figure 79:
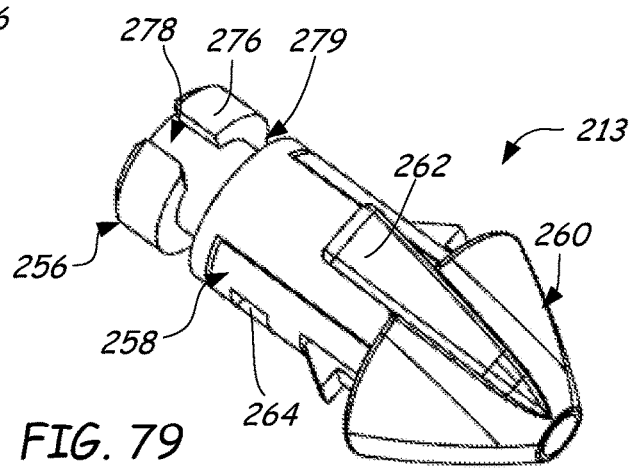
FIG. 79 illustrates enlarged assembled view of the nose of FIG. 78.
Figure 80:
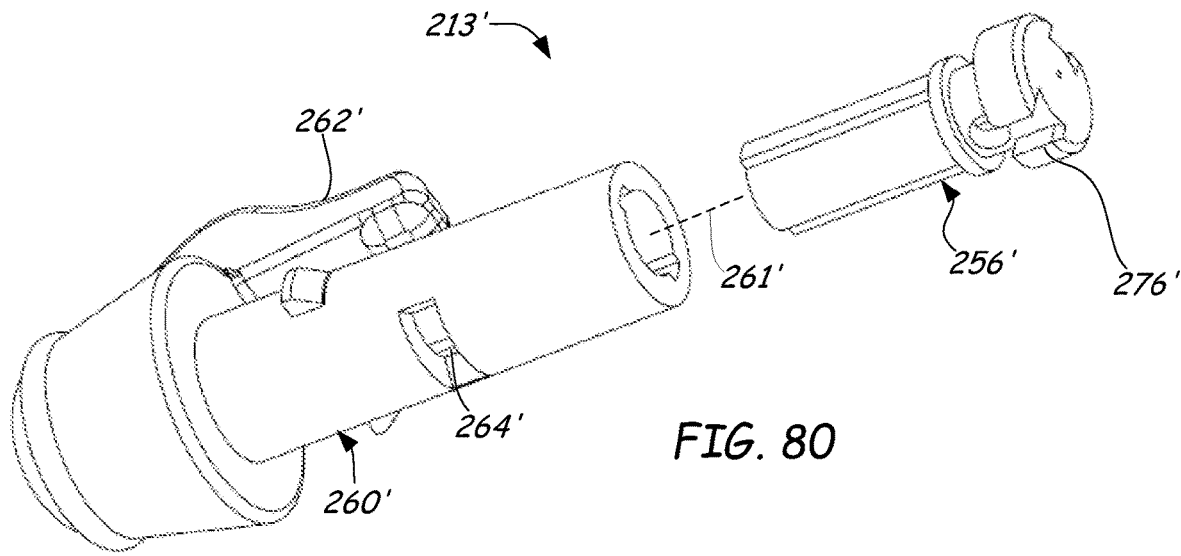
FIG. 80 illustrates an enlarged exploded view of a nose of the nose assembly illustrated in FIGS. 4 and 5.

Besides nose assembly 203 including cutting sheath 206, positioning rod 204 and actuation member 214, nose assembly 203 also includes nose 213, which is illustrated in an enlarged exploded view in FIG. 78 and in an enlarged assembled view in FIG. 79. In regards to insertion system 200', FIG. 80 illustrates an enlarged exploded view of nose 213'. Nose 213 or 213' includes an actuating mechanism interface component or pull 256 or 256', a suction interface component or drain 258 and a nose piece 260. In regards to the insertion system 200 embodiment, drain 258 and nose piece 260 are two separate components. In regards to the insertion system 200' embodiment, drain 258 and nose piece 260 are integral and labeled as drain-nose piece 260'. In other embodiments, drain 258 and nose piece 260 can be overmolded directly onto positioning rod 204 to ensure correct orientation and sufficient bond. Regardless, the use of a suitable high viscosity lubricant, such as silicone grease, can be used between pull 256' and drain-nose piece 260' to eliminate gaps which can cause suction loss without negatively impacting the friction between those parts.

From positioning rod 204 (not illustrated in FIG. 78 or 79), actuation member 214 (illustrated in FIG. 78) attaches to actuating mechanism interface or pull 256 or 256' along central axis 261 or 261' through nose piece 260 and suction interface component or drain 258 or drain-nose piece 260'.

In this embodiment, a fastener 259, such as a threaded set screw (FIGS. 78 and 79), can be used to hold actuating member 214 against an internal face of pull 256 or 256'. In FIGS. 78 and 79, the threaded set screw is advanced through pull 256 in a direction substantially perpendicular to central axis 261 and tightened down In other embodiments, such as the embodiment illustrated in FIG. 80, actuating member 214 can be held against internal face of pull 256 or 256's using an adhesive and then trimmed off. Eliminating a hole in pull 256 or 256' for receiving a fastener or other mechanical fastener would ultimately prevent suction loss. However, assembling actuating member 214 to pull 256 or 256' becomes more difficult. To eliminate the hole and in one embodiment, a mechanical gripping feature, for example a one-way cam gripper, could be over-molded into pull 256 or 256' such that actuating member 214 is advanced through to the correct position during assembly and automatically locks in place.

As illustrated in FIGS. 78 and 80, an aperture in the distal end of pull 256 and 256' allows actuating member or wire 214 to pass through. In FIG. 80, the aperture is smaller than the aperture in FIG. 78. A smaller hole prevents suction loss when insertion system 200' undergoes a suction functionality. Further, actuating member or wire 214 is mechanically sealed in the aperture with, for example, adhesive, to prevent even further suction loss when insertion system 200' undergoes a suction functionality. Positioning rod 204 (again not illustrated in FIG. 78 or 79) attaches to suction interface component or drain 258 or drain-nose piece 260' along central axis 261 or 261' through nose piece 260. In particular, proximal end 248 (FIG. 69) of positioning rod 204 traverses only a partial length of drain 258 or drain-nose piece 260'.

Drain 258 or drain-nose piece 260' includes one or more suction apertures 264 or 264' (of which only one is illustrated in FIGS. 78 and 79 and of which there is only a single suction aperture in FIG. 80). In the embodiments illustrated in FIGS. 78 and 80, suction apertures 264 or 264' are square in shape. However, any shape is possible. Drain 258 or drain-nose piece 260' may also include a suction block to redirect fluid traveling along axis 261 or 261' through suction apertures 264 or 264' and into a fluid channel in the main body of the handle assembly 205 or 205'. In FIG. 78, fastener 259 or an adhesive fastener not only functions as a device for fastening actuation member 214 in place, but also acts as the suction block. In another embodiment, though not illustrated, a suction block can include a thin polymer washer with a small hole or slit cut through it to allow the actuation member 214 to pass through, but still allow actuation member 214 to closely conform to drain 258, thus blocking off any suction losses. In one embodiment, a suction block includes a polyurethane rubber washer with a radial slit extending halfway across the circular face. The physical properties of the suction block, along with the geometry, can be modified to increase or decrease the frictional resistance the actuating member 214 experiences passing through it. Similar to the bends that can be made in actuation member 214 to increase or decrease drag inside positioning rod 204, the aperture size in the suction block, its frictional properties, and its thickness can all be changed to increase or decrease drag on the actuation member 214.

Nose piece 260 or drain-nose piece 260' includes a tab 262 or 262' which interfaces or engages with a stop component 296 or 296' on the handle assembly 205 or 205'. Tab 262 or 262' provides a visual as well as functional means of registering nose assembly 203 or 203' with handle assembly 205 or 205' to achieve desired positioning relative to each other as well as to allow nose assembly 203 or 203' and handle assembly 205 or 205' to assemble or disassemble (connect or disconnect). Details regarding the connection between nose assembly 203 or 203' and handle assembly 205 or 205' will be discussed in detail below.

Figure 81:
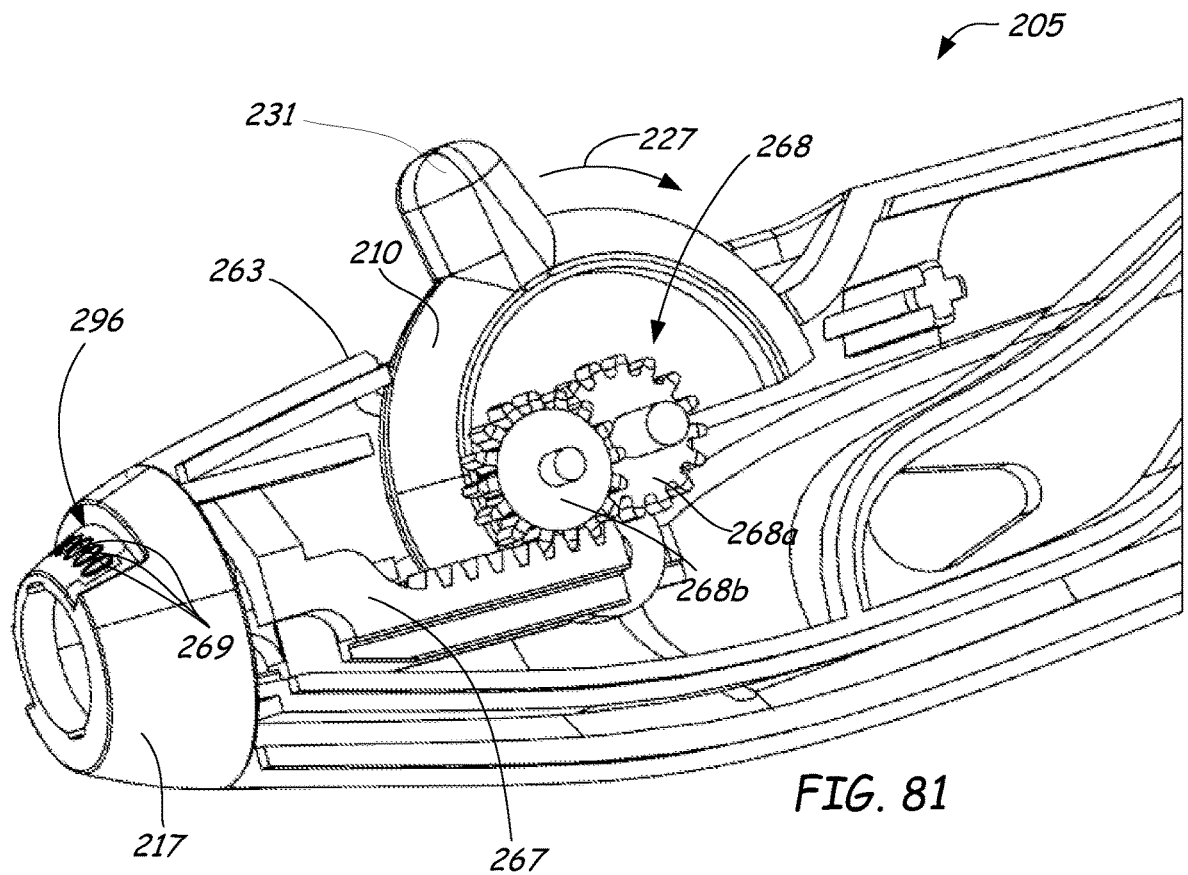
FIG. 81 illustrates a partial perspective cut-away view of the handle assembly of the insertion system illustrated in FIGS. 2 and 3.
Figure 83:
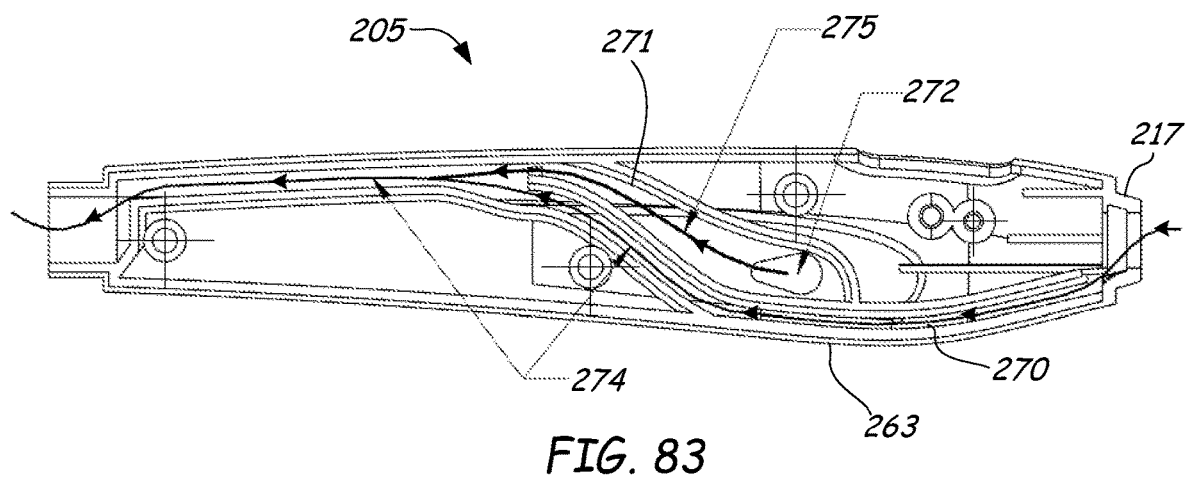
FIG. 83 illustrates a section view of the handle assembly of the insertion system illustrated in FIGS. 2 and 3.

FIG. 81 illustrates a partial perspective cut-away view of handle assembly 205 of insertion system 200 and FIG. 83 illustrates a section view of main body 263 of handle assembly 205 of insertion system 200. Handle assembly 205 includes main body 263, nose interface 217 for interfacing with nose assembly 203, a rotatable actuating element or scroll wheel 210, a rack 267 and one or more drive gears 268 coupling the rotatable actuating element or scroll wheel 210 to rack 267.

As illustrated in FIG. 83, main body 263 includes a primary fluid channel 270, a secondary fluid channel 271 and one or more suction weep holes 272. The proximal end of main body 263 of handle assembly 205 includes an area for receiving a fitting for coupling main body 263 to a source of negative pressure. For example, FIGS. 2 and 3, illustrate the distal end of handle assembly 205 as including a barbed fitting 273.

Suction, as provided by the suction source, passes through the primary and secondary fluid channels 270 and 271 inside main body 263 of handle assembly 205. Primary fluid channel 270 is in fluid communication through apertures 264 in drain 258 and down the positioning rod 204 to cutting edge 209 of cutting sheath 206. Secondary fluid channel 271 branches off primary fluid channel 270 and is in communication with the one more weep holes 272. Weep holes 272 provide the control for delivering suction to distal end 207 (FIGS. 50 and 65) of the positioning rod 204. In one embodiment, a plug, adhesive patch, or other suitable component can be used to block off one of the two weep holes. The user is able to cover the remaining weep hole as desired to direct the application of negative pressure to distal end 207 of positioning rod 204 or insertion end 202. Handle assembly 205 can be provided with a repositionable component, such as a flexible polymer plug or repositionable adhesive patch, for plugging one of the weep holes. The repositionable component can be left in place or removed as desired by the user. In an alternative embodiment, both weep holes 272 could be plugged initially, and the user could remove the plug over the weep hole of their choice prior to use.

With reference to FIG. 83 and in one embodiment, primary fluid channel 270 of main body 263 provides a fluid path 274 that communicates between the suction source (i.e., the barbed fitting 273) and distal end 207 of positioning rod 204. Secondary fluid channel 271 branches off primary channel 270 and provides a fluid path 275 that communicates with the weep holes 272. By placing secondary fluid channel 271 above primary fluid channel 270 and making the intersection of second fluid channel 271 with primary fluid channel 272 such that fluid path 275 is at an acute angle to fluid path 274, the possibility of aspirated fluids passing down secondary channel 271 and out of weep holes 272 is eliminated or reduced.

While the weep holes 272 are positioned along the lateral edges of main body 263 of handle assembly 205, it should be understood that they could be located on the top and/or bottom of main body 263 as well, and that while barbed fitting 273 is oriented along a central axis of main body 263, it could be located along the length of main body 263 at an angle that is not parallel to the central axis of the main body.

It is possible for suction traveling through main body 263 to generate noise which can be transmitted into the ear canal even when the weep holes 272 are not blocked and suction is not being provided to distal end 207 of positioning rod 204, and this noise can be disturbing to the patient. To prevent painful noise, a valve or shutoff can be located between the barbed fitting 273 and weep holes 272 such that negative pressure is still present, but the air flow that generates the noise is prevented.

Nose interface 217 is positioned at a distal end of handle assembly 205 and includes a stop component 296. Stop component 296 includes a recessed area that is recessed into nose interface 217 and partially extends around a peripheral area of nose interface 217. The recessed area includes a shelf portion 265 (illustrated in FIGS. 2 and 3) located at one end of the recessed area and a plurality of spaced apart detents 269 (FIG. 81) extending across the remaining of the recessed area.

Figure 85:
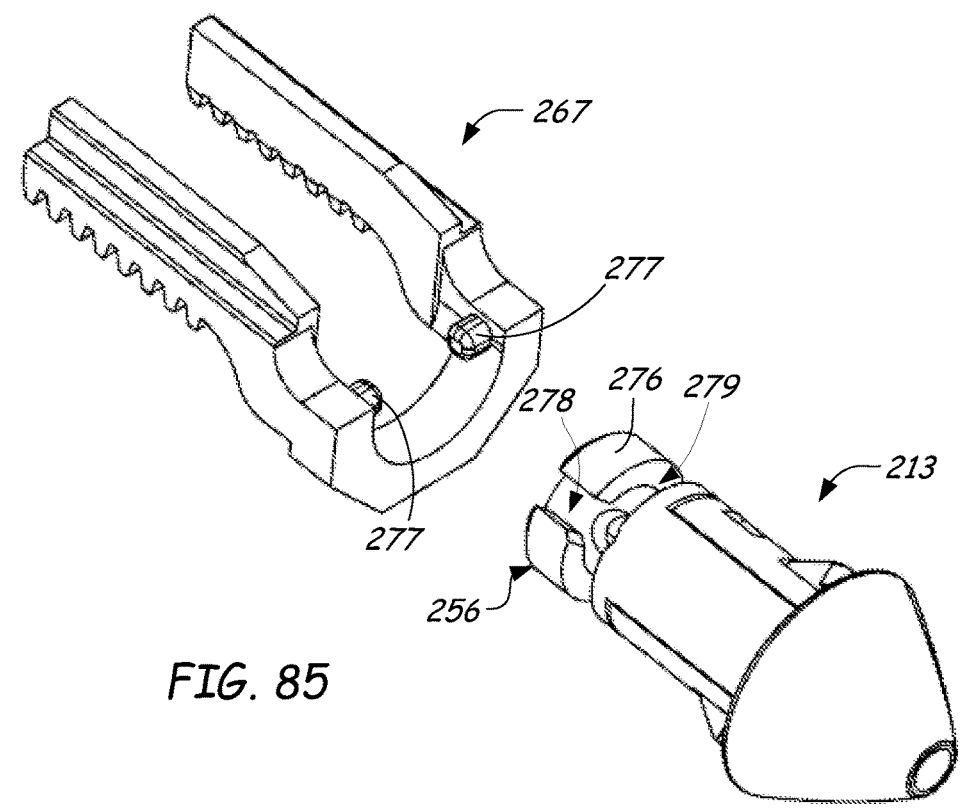
FIG. 85 illustrates an enlarged perspective view of the assembled nose of the nose assembly and the rack of the handle assembly illustrated in FIGS. 2 and 3.

To physically attach nose assembly 203 to handle assembly 205, tab 262 on nose piece 260 of nose assembly 203 engages with shelf portion 265. At the same time, a collar 276 (FIGS. 78 and 79) on pull 256 mates with one or more protrusions 277, such as a pair of protrusions, on rack 267 of handle assembly 205. FIG. 85 illustrates an enlarged perspective view of nose 213 and rack 267 before they mate together. More specifically, collar 276 includes a pair of opposing slots 278. When nose piece 260 is pushed onto shelf portion 265 of nose interface 217, collar 276 slides through protrusions 277 by way of slots 278 and is positioned on an internal side of protrusions 277. Tab 262 is then rotated from shelf portion 265 to engage with a select detent of the plurality of detents 269. Which of the detents is selected depends on the desired position or angle of nose assembly 203 relative to handle assembly 205. When tab 262 is rotated, collar 276 also mates with protrusions 277 so that pull 256 cannot move out of position. In other words, once nose assembly 203 and handle assembly 205 are pushed together, rotating them with respect to one another results in tab 262 engaging with a select detent of the plurality of detents 269 and protrusions 277 on the rack 267 turning into a groove 279 on pull 256.

Therefore, tab 262 provides a physical means of limiting the degree or rotation between nose assembly 203 and handle assembly 205. In addition, tab 262 interfaces with the number of detents 269 on handle assembly 205, which provide positive stops over the range of rotational adjustability between the nose and handle assemblies 203 and 205. The user is able to manually twist nose assembly 203 in relation to handle assembly 205 to achieve the best orientation to achieve ventilation tube placement, while the positive stops provide sufficient resistance to movement so that nose 213 does not inadvertently rotate during tube insertion. In addition, by engaging tab 262 with stop component 296, fluid path 274 through handle assembly 203 and positioning rod 204 is completed. While detents 269 are illustrated, other means of providing frictional resistance to rotation between nose assembly 203 and stop component 296 could be used. For example, merely providing a contact resistance between tab 262 and nose interface 217 of handle assembly 205 is sufficient.

Shelf portion 265 allows for ease of assembly of nose assembly 203 and handle assembly 205 including rotating tab 262 of nose 213 into the detents 269. However, disassembling nose assembly 203 from handle assembly 205 requires increased force to rotate tab 262 of nose 213 back onto shelf portion 265. Tab 262 being located on shelf portion 265 is the requisite position needed to assemble and disassemble nose assembly 203 to handle assembly 205. This feature prevents the user from accidentally adjusting the rotational orientation of the two assemblies so far that the rack 267 and pull 256 are not connected, and therefore nose 213 cannot inadvertently fall off.

Figure 82:
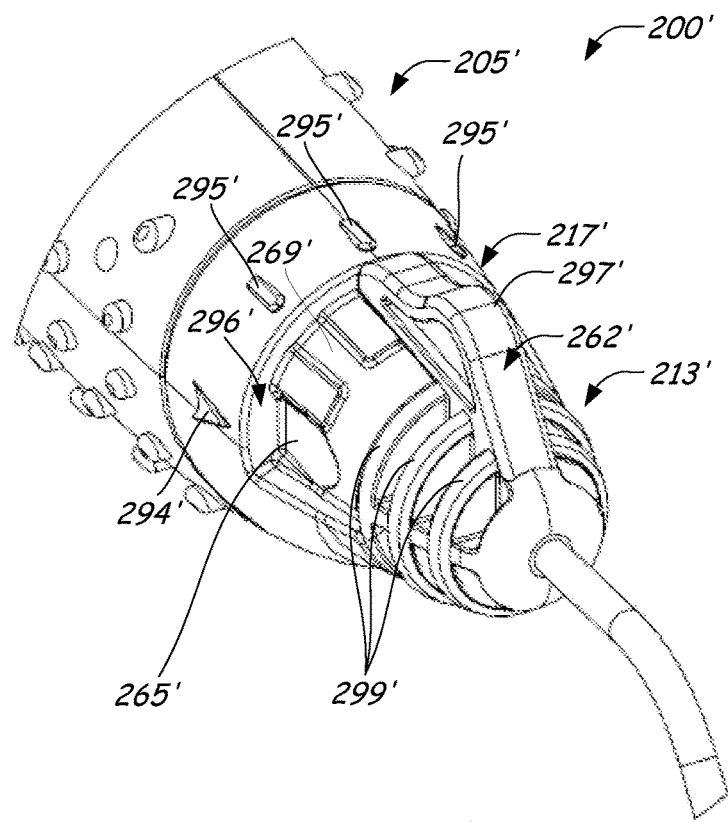
FIG. 82 illustrates a partial perspective enlarged view of the handle assembly of the insertion system illustrated in FIGS. 4 and 5.
Figure 84:
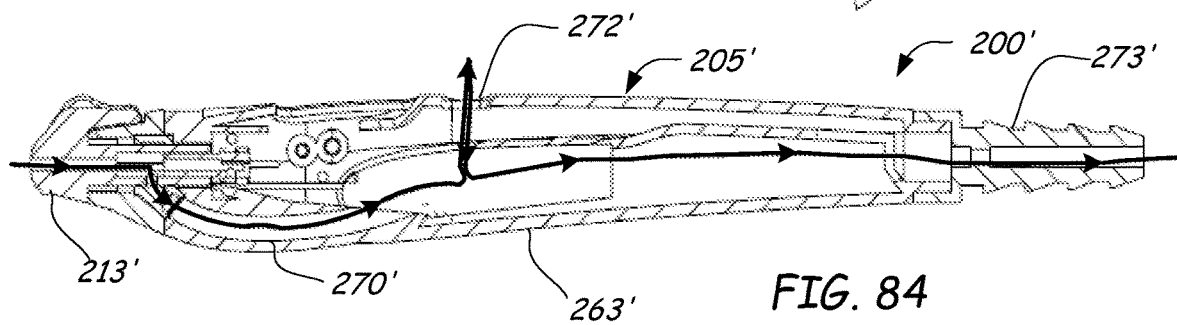
FIG. 84 illustrates a section view of the handle assembly of the insertion system illustrated in FIGS. 4 and 5.

FIG. 82 illustrates a partial perspective view of handle assembly 205' assembled to nose 213' of insertion system 200' and FIG. 84 illustrates a section view of main body 263' of handle assembly 205' and nose 213' of insertion system 200'. Handle assembly 205' includes main body 263' and nose 213'. As illustrated in FIG. 84, main body 263' includes a primary fluid channel 270' and a suction weep hole 272'. Weep hole 272' is located on an upper surface of main body 263'. The proximal end of main body 263' of handle assembly 205' includes fitting 273'. Fitting 273' can comprise soft flexible tubing so as to eliminate transferring any torque or twist created by a vacuum line to handle assembly 205'.

Suction, as provided by the suction source, passes through the primary fluid channel 270' inside main body 263' of handle assembly 205'. Primary fluid channel 270' can be defined by polymer tubing, a t-fitting and a soft polymer double sealed component, which seals around nose 213'. This sealing component goes around nose 213' and allows for replaceable noses while forming a seal and allows for rotation of the nose without breaking the seal. For example, the sealing component can be made of PVC, urethane, silicone or the like. Primary fluid channel 270' is in fluid communication through aperture 264' in drain-nose piece 260' and down the positioning rod to the cutting edge of the cutting sheath and is also in communication with weep hole 272'. Weep hole 272' provides the control for delivering suction to a distal end 207 of the positioning rod. In this embodiment, suction is available regardless of the position of scroll wheel 210' (FIGS. 4 and 5), the cutting sheath or pull 256' (FIG. 80).

Nose 213' is positioned at a distal end of handle assembly 205' and includes a stop component 296'. Stop component 296' includes a recessed area that is recessed into a nose interface 217 and partially extends around a peripheral area of nose interface 217'. The recessed area includes a shelf portion 265' located at one end of the recessed area and a plurality of spaced apart detents 269' (of which only one is visible in FIG. 82) extending across or about the recessed area. Like shelf portion 265, shelf portion 265' engages with tab 262' when nose 213' is initially attached to handle 212'. As illustrated, stop component 296' includes three spaced apart detents. Each detent represents a locking point where tab 262' can be engaged when nose 213' is rotated for operation.

Although not specifically illustrated in FIGS. 4 and 5, FIG. 82 illustrates a plurality of visual markers located at a distal end of handle assembly 205'. In particular, handle assembly 205' can include an insertion marker 294' and stop markers 295'. Insertion marker 294' corresponds with shelf portion 265' and is in the shape of a triangle. In this way, a clinician can easily ascertain where a tab 262' needs to align with and engage with stop component 296' for the insertion or removal of handle 212'. Each stop marker 295' corresponds with a detent 269' and is in the shape of a dash. In this way, a clinician can easily ascertain the different rotational adjustments that tab 262' can make to adjust the alignment of nose assembly 203'.

To physically attach nose assembly 203' to handle assembly 205', tab 262' on drain-nose piece 260' of nose assembly 203' engages with stop component 296'. At the same time, a collar 276' (FIG. 80) on pull 256' mates with component in handle assembly 205' to provide a zero insertion force. Tab 262' is then rotated from the shelf portion in a cam action to tighten nose 213' and engage tab 262' with a select detent of the plurality of detents 269. Which of the detents is selected depends on the desired position or angle of nose assembly 203' relative to handle assembly 205'.

Therefore, tab 262' provides a physical means of limiting the degree or rotation between nose assembly 203' and handle assembly 205'. In addition, tab 262' interfaces with the number of detents 269' on handle assembly 205', which provide positive stops over the range of rotational adjustability between the nose and handle assemblies 203' and 205'. Tab 262' also includes a flange 297' to push during rotational adjustment. Further, nose 213' includes at least one circumferential rib or boss 299' (FIG. 82 illustrate a plurality of ribs or bosses 299') to provide a grip feature for the push or pull or insertion or removal of nose 213'.

After assembly of nose assembly 203 or 203' and handle assembly 205 or 205', axial movement of rack 267 along a central axis 261 results in a corresponding movement of pull 256 or 256', actuation member 214, and therefore cutting sheath 206. As previously described, rack 267 is coupled to actuating element or scroll wheel 210 or 210' through the one or more drive gears 268. Therefore, a user can rotate rotatable actuating element or scroll wheel 210 or 210' in a direction 227 (FIG. 81) from a first position (shown in FIGS. 2, 3, 4 and 5), which is a forward position located toward stop component 296 or 296', to a second position, which is a backward position located toward fitting 273 or 273', to move cutting sheath 206. More specifically, clockwise rotation or backwards rotation of scroll wheel 210 or 210' retracts cutting sheath 206 and therefore deploys ventilation tube 215 since cutting sheath 206 is the element to which ventilation tube 215 is being constrained. While it is possible for scroll wheel 210 or 210' to rotate forwards to deploy a ventilation tube, inadvertent movement imparted to the handle during such a rotation would result in a deeper penetration of the cutting sheath behind the patient and toward the user is a safety feature.

Scroll wheel 210 or 210' can further comprise a physical feature or bump 231 or 231' to provide physical feedback to the user. For example, bump 231 or '231' located on the outer surface of scroll wheel 210 or 231' can be a secondary material overmolded onto scroll wheel 210 or 210' to provide better friction between the user and scroll wheel 210. In particular, bump 231 or 231' can have a width that is larger than a width of scroll wheel 210 or 210' to allow a slight mechanical advantage to the user by providing a longer lever arm about the axis of rotation. Because many ventilation tube placement operations are performed through an operating microscope, it is common for surgeons to be handed instruments 'blindly', and they must be able to orient the device in their hand by feel instead of visually. Bump 231 or 231' shown on scroll wheel 210 or 210' in FIGS. 2, 3, 4, 5 and 87 allows the clinician to feel where scroll wheel 210 or 210' is before and during actuation.

The location of scroll wheel 210 or 210' as illustrated in FIGS. 2, 3, 4 and 5 allows insertion system 200 or 200' to be actuated using a thumb or a forefinger, and in combination with the rotational adjustability of nose assembly 203 or 203' and dual weep holes 272 or single weep hole 272' allows insertion system 200 or 200' to be used in a right-handed or left-handed orientation. When using the thumb to actuate scroll wheel 210, an index finger is used to cover one of the weep holes 272. When using the index finger to actuate scroll wheel 210, the thumb is used to control suction by covering one of the weep holes 272. The location of the single weep hole 272' on insertion system 200' eliminates the need for a means of plugging the unused weep hole. The same digit used to actuate scroll wheel 210' is also used to cover weep hole 272' to apply suction. The symmetrical location of weep hole 272', combined with it's proximity to scroll wheel 210' reduces the amount of hand movement required between the steps of actuation and suction application, and allows the user to employ the same digit to achieve both functions.

As also illustrated in FIG. 81 and as previously discussed, the one or more drive gears 268, which allow the rotational motion of scroll wheel 210 to be translated into linear motion for retracting cutting sheath element 206, includes at least a scroll gear 268*a* and a reversing gear 268*b*. The use of a sequence of gears as shown allows for a change in direction between scroll gear 268*a* and scroll wheel 210. In addition, the use of a sequence of gears allows for a gearing up or down to achieve different mechanical advantages. For example, scroll wheel 210 may rotate through a greater or lesser angle than the final drive gear.

Figure 86:
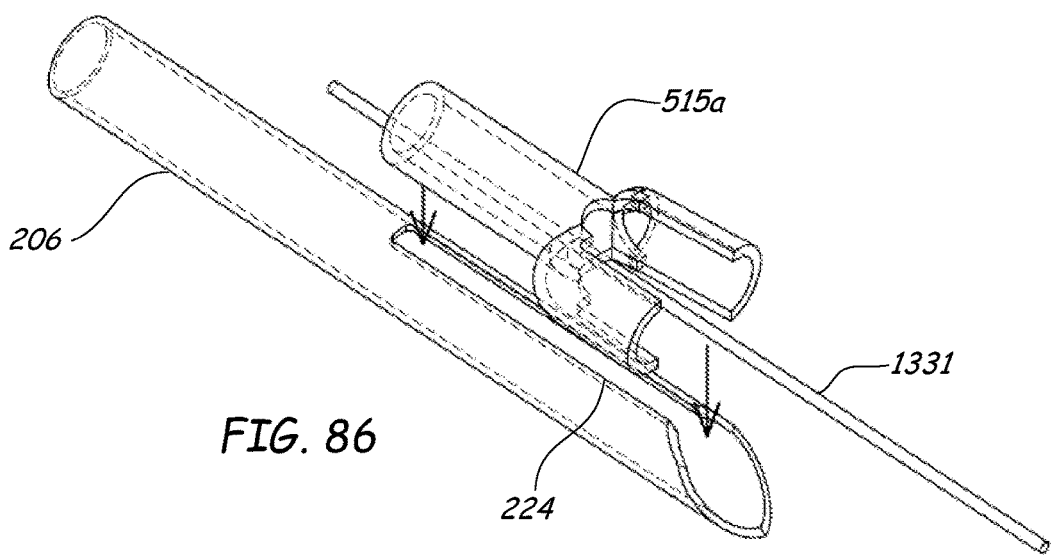
FIG. 86 illustrates a ventilation tube being radially loaded into the cutting sheath of the insertion system illustrated in FIGS. 2 and 3.

FIG. 86 illustrates a flexible polymer ventilation tube, such as T-tube 515*a* of FIG. 37, being radially loaded into cutting sheath 206. Using a mandrel 1331 inserted into the inner lumen of ventilation tube 515*a*, the ventilation tube 515*a* is positioned proximal to slot 224, and then forced through the slot 224 and down into the inner lumen of cutting sheath 206. While T-tube 515*a* is shown in FIG. 29, it should be realized that other types of tubes can be used including grommet type tubes.

Figure 87:
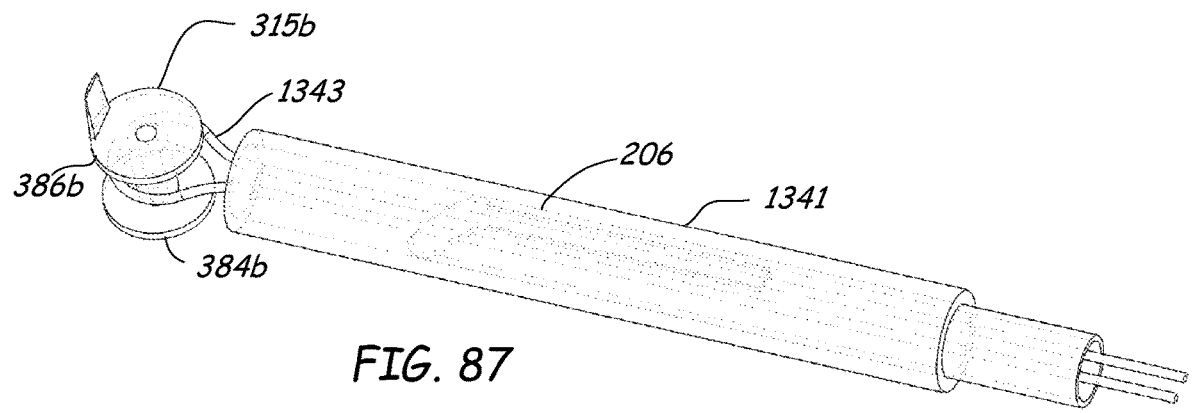
FIG. 87 illustrates a ventilation tube being axially loaded into the cutting sheath of the insertion system illustrated in FIGS. 2 and 3.

FIG. 87 illustrates a flexible polymer ventilation tube, such as grommet tube 315*b* of FIG. 7, being axially loaded into cutting sheath 206. Cutting sheath 206 is inserted into a snug loading tube 1341 (for example a clear or translucent polymer tube) such that the beveled distal end of cutting sheath 206 is inside loading tube 1341. A flexible filament 1343, such as a string or nylon monofilament, is passed through cutting sheath 206 such that a closed loop extends past the beveled distal end of cutting sheath 206 and out of the loading tube 1341 while the free ends extend out the proximal, unbeveled end of cutting sheath 206. A flexible polymer ventilation tube, for example a silicone Paparella style such as tube 315*b*, is passed through the loop in filament loop, and the loop is tightened down around the middle of the tube body. By holding onto the medial flange 384*b* of ventilation tube 315*b* while pulling on filament 1343, the tube 315*b* is pulled into the polymer tube with the lateral flange 386*b* entering first. With ventilation tube 315*b* pulled completely into loading tube 1341, the ventilation tube 315*b* can be rotated within cutting sheath 206 to align any tabs or flanges, such as tab 388*b*, on ventilation tube 315*b* with the slot 224 in cutting sheath 206. Ventilation tube 315*b* is then pulled into cutting sheath 206 with filament 1343. When ventilation tube 315*b* is positioned correctly in cutting sheath 206, one free end of filament 1343 is pulled while the other end is allowed to pull into cutting sheath 206 and around ventilation tube 315*b* so that it can be removed from around the ventilation tube and from inside cutting sheath 206. The loading tube 1341 can then be removed from cutting sheath 206, or it can be left in place to protect the cutting edge if the beveled distal end of cutting sheath 206 is sharpened.

In this loading method, a lancet style grind ensures that any cutting edges on the beveled portion of the sheath are located flush against the inner diameter of the loading tube, minimizing the chance that they will catch on or cut the ventilation tube during loading. A back grind on the cutting sheath would position the cutting edges on the inner diameter of the cutting sheath, which would be spaced away from the wall of a loading tube and could catch on or cut a flexible ventilation tube during the loading process.

Figure 88:
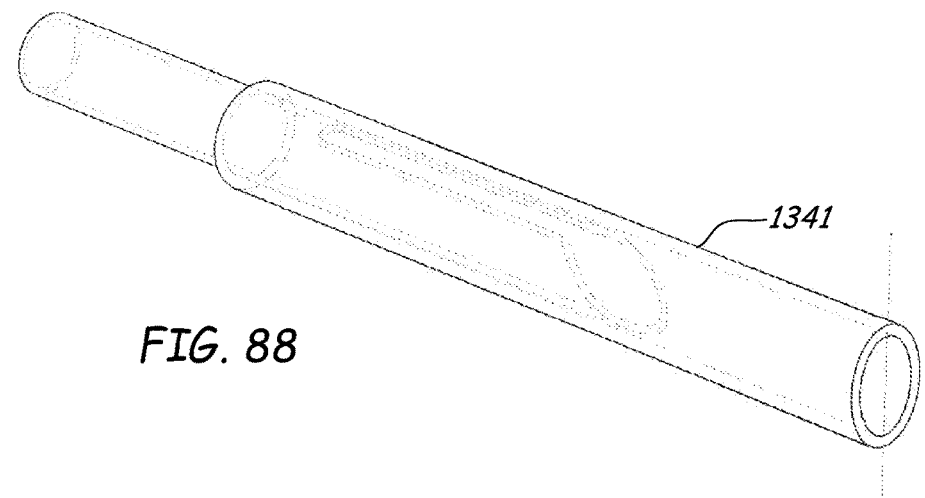
FIG. 88 illustrates an alternative embodiment for the loading tube illustrated in FIG. 30.

As shown in FIG. 87, the loading tube 1341 may be circular along its entire length, or may match the outer geometry of the sheath. In another embodiment, loading tube 1341 may transition from an oval shape at a distal end to a circular shape where the distal end of the cutting sheath is positioned as shown in FIG. 88. An oval shape at the distal end of the loading tube where the ventilation tube is inserted helps ensure the medial and lateral flanges of the ventilation tube fold down in a repeatable fashion. Because medial and lateral flanges on a ventilation tube may be fully circumferential, and the cutting sheath has a slot, it is important to fold the medial and lateral flanges down such that they don't protrude through the slot, but that any tabs that are intended to protrude through the slot are positioned correctly such that they remain protruding.

Figure 89:
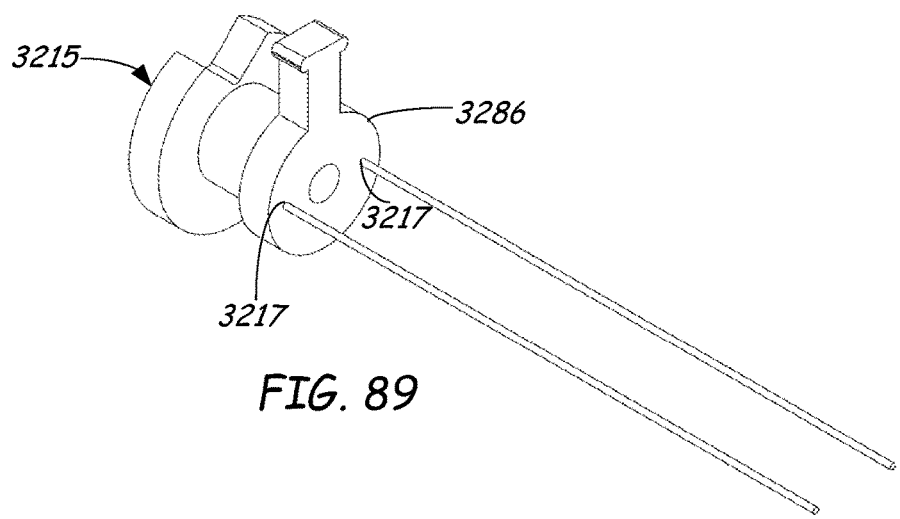
FIG. 89 illustrates an alternative embodiment for a ventilation tube for axially loading the tube into a cutting sheath.

FIG. 89 illustrates an alternative embodiment for a ventilation tube 3215 for axially loading into a cutting sheath. As described above, holes, or other features may be included on the ventilation tube's lateral flange or tabs that make it easier to load the ventilation tube. For example, a ventilation tube could have one or more holes 3217 in the lateral flange 3286 that a filament is passed through during loading that allows it to be pulled into the cutting sheath. Such a filament could then be removed before use, or could be left in place as a safety element which could be used to grasp the ventilation tube in cases where it may inadvertently fall into the inner ear during insertion.

The ability to remove a nose assembly from a handle assembly of an insertion system makes it easier to load ventilation tubes during manufacturing by enabling access to a proximal end of a positioning rod. In this way, it is possible to use a pulling filament to load ventilation tubes axially into the distal end of the cutting sheath. By using a removable attachment (such as a set screw) to anchor the actuating wire inside the nose assembly, the ventilation tube can be loaded before the cutting sheath is assembled onto the positioning rod.

The ventilation tube can also be loaded after the nose assembly and the handle assembly are fully assembled. The pulling filament can be fed through a loading tube and through the slot in the cutting sheath such that the ventilation tube can be pulled into the sheath without access to the proximal end of the cutting sheath for insertion of the pulling filament.

Loading methods that pull the ventilation tube into position by grasping it behind the lateral flange are preferred because they result in the proximal flange folding up and away from the main body of the ventilation tube and the distal flange folding down and away from the main body of the ventilation tube as well as potentially providing a slight stretch to the main body of the tube. This is desirable, because such a configuration increases the spacing between the lateral and medial flanges on the ventilation tube, which makes it easier to position the ventilation tube across the TM. Loading methods that push the ventilation tube axially into the distal end of the cutting sheath may result in the lateral flange of the ventilation tube folding down and toward the main body of the tube.

Figure 90:
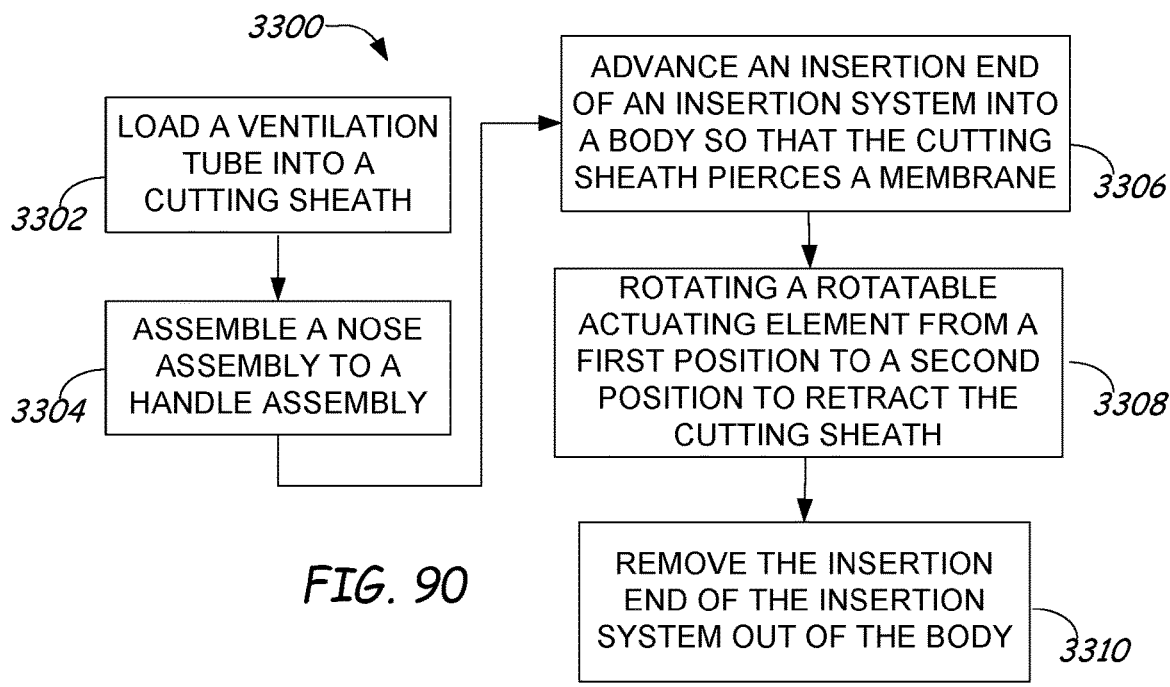
FIG. 90 illustrates a flow chart describing a manual process for inserting a ventilation tube into a tympanic membrane of the body.

FIG. 90 illustrates a flow chart 3300 describing a manual process for inserting a ventilation tube 215 into a TM of the body using insertion system 200. At block 3302, ventilation tube 215 is loaded into cutting sheath 206. At block 3304, nose assembly 203 is assembled to handle assembly 205 by interlocking nose 213 with stop component 264. It should be realized, however, that blocks 3302 and 3304 can be performed in the reverse order as well. Such loading procedures are illustrated and discussed in regards to FIGS. 86-89. At block 3306, insertion end 202 is manually advanced through a body, for example the outer ear, such that distal end 209 of cutting sheath 206 pierces through a membrane, such as a TM. As discussed above, how far to insert insertion end 202 or distal end 209 of cutting sheath 206 into the TM is determined by a visual or physical indicators located at insertion end 202. In one embodiment, a visual indicator can be a tab 288 located on ventilation tube 215 that is protruding through a slot 224 in cutting sheath 206. Other or additional visual or physical indicators can be located on the outer surface of cutting sheath 206 including sensing elements as described in detail above. After insertion end 202 is inserted through the TM, cutting sheath 206 retraction is accomplished by rotating rotatable actuating element 210 on the handle assembly 205 from a first position to a second position (i.e., in a direction toward the user of the insertion system 200) as described in block 3308. This movement causes cutting sheath 206 to fully retract from the TM. Removal of insertion end is then performed at block 3310 by removing insertion end 202 and therefore insertion system 200 out of the body or outer ear.

Figure 91:
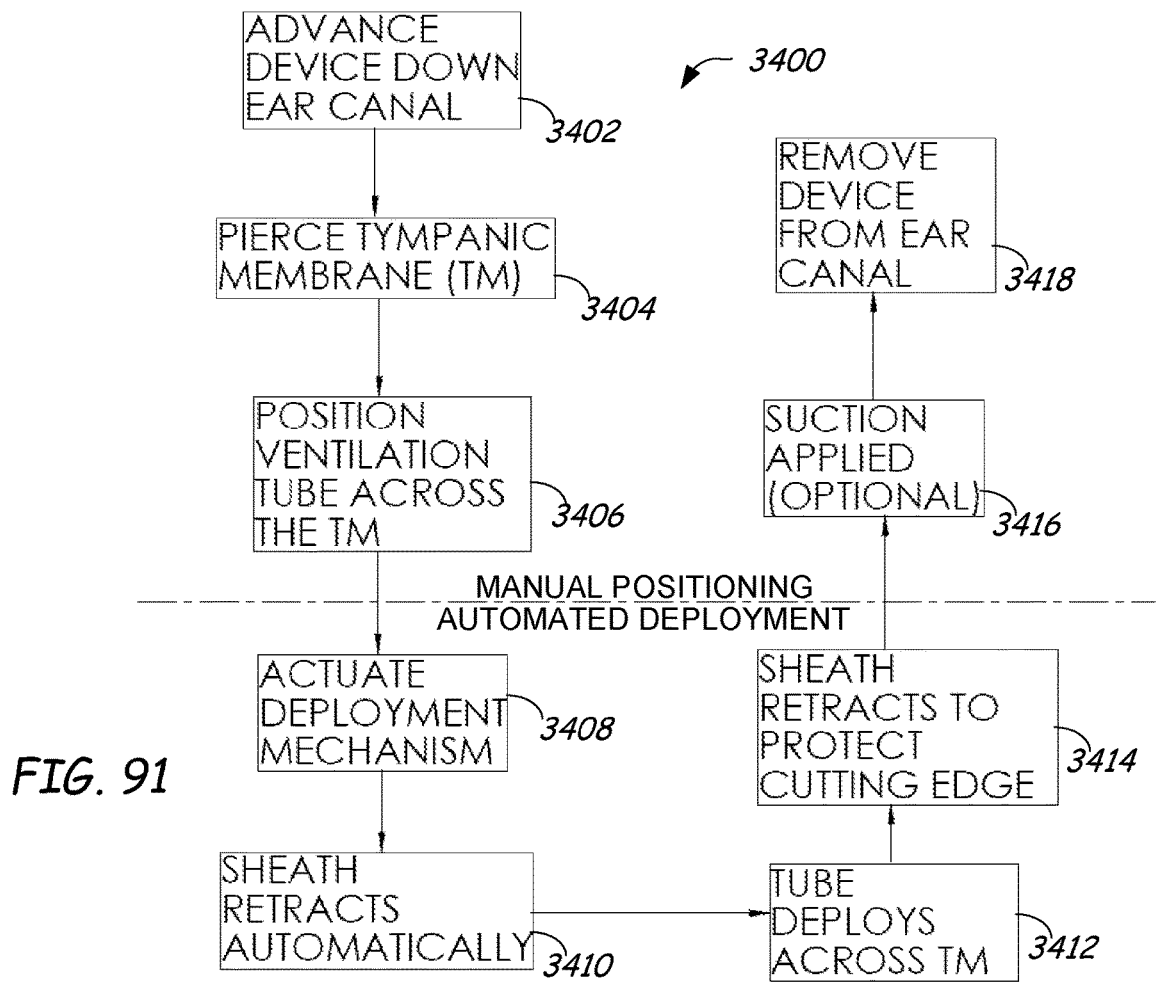
FIG. 91 illustrates a flow chart describing a semi-automatic process for inserting a ventilation tube into a tympanic membrane of the body.

FIG. 91 illustrates a flow chart 3400 describing a semi-automated process for inserting a ventilation tube into a TM of the body using an insertion system. At block 3402, an insertion end is manually advanced through an outer ear such that a distal end of a cutting sheath pierces through the TM as described at block 3404 and the ventilation tube is located across the TM as described in block 3406. As discussed above, how far to insert insertion end 202 or distal end of cutting sheath into the TM is determined by a visual or physical indicator. After the insertion end is inserted through the TM, a deployment mechanism is actuated at block 3408. Actuation of the deployment mechanism provides for the automatic retraction of the cutting sheath as described in block 3410 and therefore the automated deployment of a ventilation tube as described at block 3412. The automated retraction causes cutting sheath 206 to fully retract from the TM as described in block 3414. At block 3416, suction can be optionally applied and at block 3418 the insertion system is manually removed from the ear canal.

Figure 92:
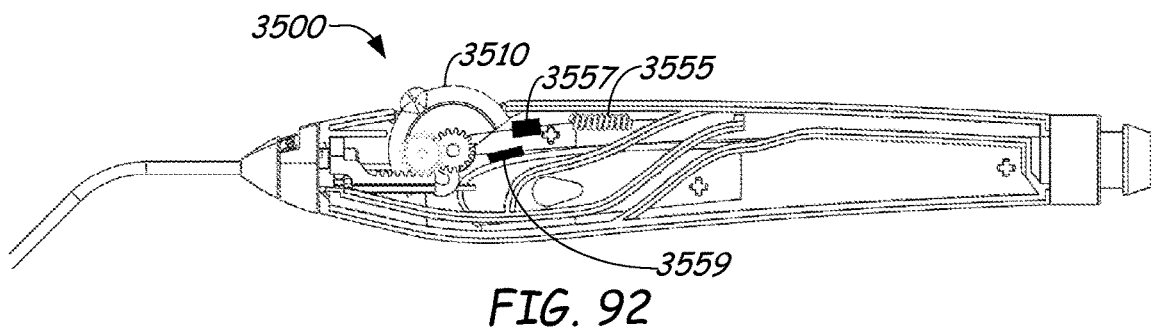
FIG. 92 illustrates an embodiment of an insertion system including elements which facilitate the semi-automated placement of ventilation tubes as illustrated in FIG. 91.

FIG. 92 illustrates an embodiment of an insertion system 3500 comprising elements which facilitate the semi-automated placement of ventilation tubes as described above in FIG. 91. Shown is a spring 3555, which automatically retracts the cutting sheath when a deployment mechanism is depressed. In FIG. 33, spring 3555 is configured to pull back on rotatable element or scroll wheel 3510. Also shown are an optional damper 3557 to slow the cutting sheath retraction to a controlled rate, and a shock absorber 3559, which stops the range of motion of the retraction. Both damper 3557 and shock absorber 3559 by themselves or working in combination can decrease the noise generated by insertion system 3500 during deployment, reducing the noxious stimuli which may cause a patient to move upon ventilation tube deployment. Damper 3557 also allows for the use of an oversized spring 3555 to provide more than sufficient actuation force without a comparable increase in the speed of the cutting sheath retraction or the noise generated by the retraction mechanism during motion or at the end of its range of motion.

Figure 93:
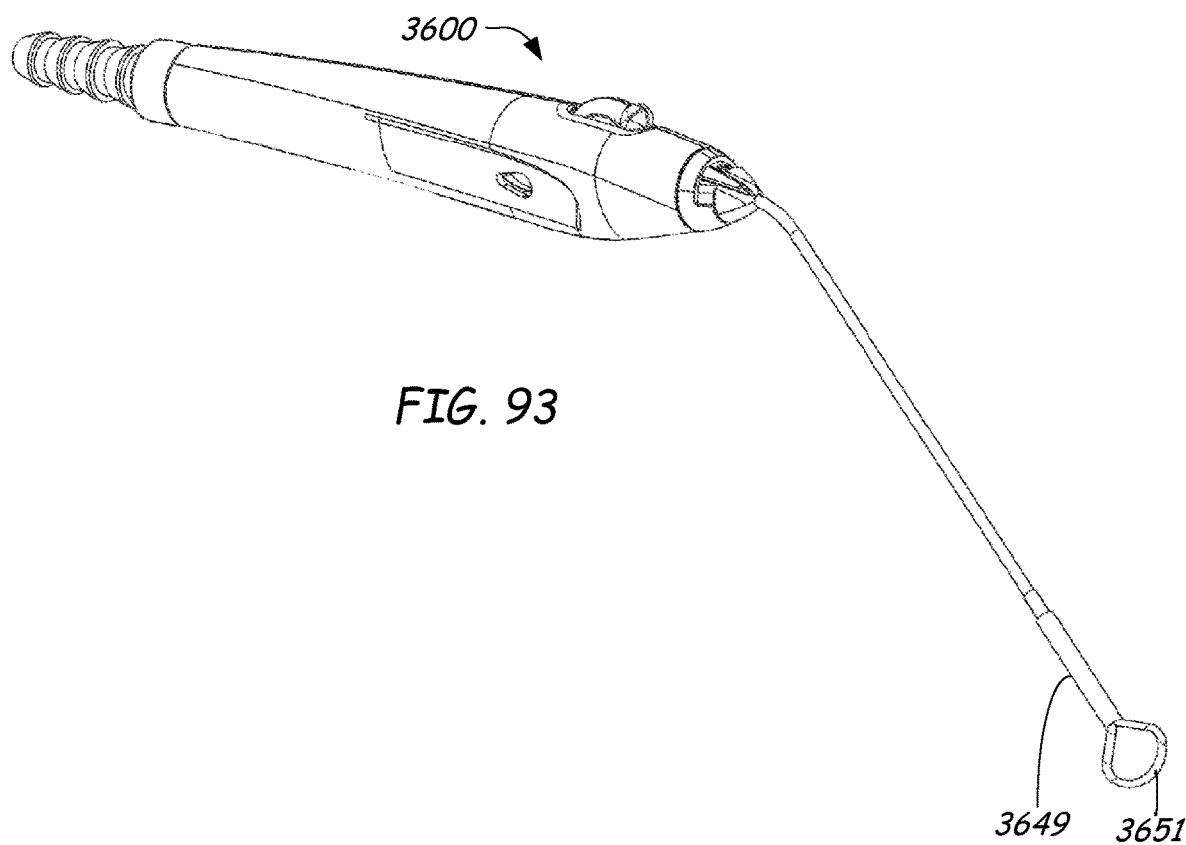
FIG. 93 illustrates yet another embodiment of an insertion system including a removable element that can be slid onto the cutting sheath such that the cutting sheath is covered and protected.

FIG. 93 illustrates yet another embodiment of an insertion system 3600 comprising a removable element 3649 that can be slid onto the cutting sheath (hidden from view in FIG. 93) such that the cutting sheath is covered and protected. The removable covering element 3649 can also include a means for the application of a topical anesthetic or other medication to the ear canal or TM. Shown is a loop 3651 that could be used to apply an anesthetic, such as phenol, to the TM. After application of the anesthetic, the covering element 3649 can be removed such that the cutting sheath is exposed and can be used to implant a ventilation tube. The removable element 3649 could also be shaped so as to function similarly to a curette and could be used to clean the ear canal prior to tube placement. The removable element 3649 could be shaped so as to accept and hold an absorbable element such as a piece of open cell foam or absorbent cloth, which could then be used to transport a medication down the ear canal.

The removable nature of the nose assembly from the 'rack and pull' interface between the nose assembly and the handle assembly allow for function-specific nose assemblies other than the insertion type function of the describe nose assembly 203 for inserting a ventilation tube. For example, a nose assembly that only applies topical analgesic is possible. In such an embodiment, the cutting sheath could be replaced by an absorbent pad, and the actuation mechanism could trigger the release of an analgesic stored within the hollow positioning rod or another element such that it is absorbed into the nose assembly for application. A nose assembly specialized for the creation of myringotomies only without subsequent tube placement is another exemplary function-specific assembly. Such a nose assembly could comprise an element to incise the TM and an element to capture a sample of fluid for laboratory analysis. Upon the incision and capture of a sample, the entire nose assembly could be removed from the handle and sent to a laboratory. A nose assembly for spraying or atomizing medication is another exemplary function-specific assembly. Such a nose assembly could comprise a distribution element for dispersing the medicine located along or in place of the positioning rod. Actuation at the handle would result in the release and distribution of the medication. A viewing nose assembly is still another exemplary function-specific assembly. The viewing nose assembly could comprise a positioning member with a flexible distal portion and a viewing member, such as a fiber optic scope. Actuation of the scroll wheel would move the flexible distal portion of the viewing member, allowing a clinician to change the viewing zone inside the body.

A nose assembly for inserting ear wicks of various length is yet another exemplary function-specific assembly and could comprise all of the components described for nose assembly 203, but also comprises an adjustable visualization element that lets the user adjust a visualization tab independent of the sheath. Because an ear wick may not include a visualization tab, a tab on the cutting sheath, or on a secondary sheath may be necessary. For example, FIG. 68 illustrates a visualization tab 688 on safety sheath 637. A visualization tab on a secondary sheath that is frictionally attached over a cutting sheath would allow the user to manually adjust the depth of the visualization tab, and would also allow the user to rotate the visualization tab around the cutting sheath to for optimal placement and direct visualization. Such an adjustable secondary visualization tab could be used on any nose assembly where adjustability or enhanced depth visualization is desired. Other function-specific removable assemblies than those that are described are possible.

Figure 94:
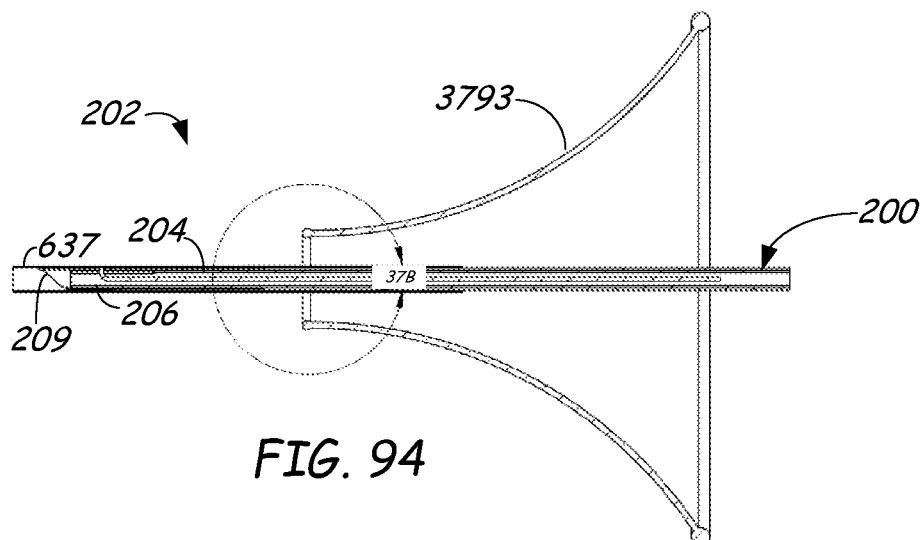
FIG. 94 illustrates a section view and FIG. 95 illustrates an enlarged view of the insertion end of the insertion system of FIGS. 2 and 3 interfacing with a speculum-like device.
Figure 95:
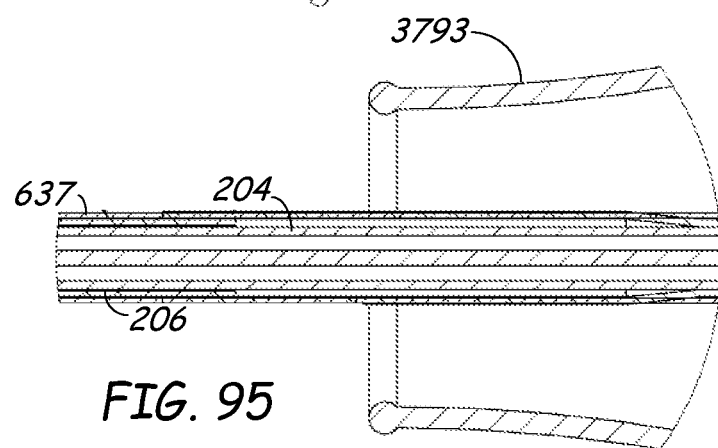

FIG. 94 illustrates a section view of insertion end 202 of insertion system 200 interfacing with a speculum-like device 3793. FIG. 84 illustrates an enlarged view of FIG. 94. In this embodiment, safety sheath 637 serves to cover the joint between the cutting sheath 206 and the positioning rod 204, ensuring that the proximal end of the safety sheath does not contact the front lip of the speculum 3793 during use, which could interfere with the retraction of cutting sheath 206 required for ventilation tube deployment. An alternative embodiment uses a cutting sheath with a tapered proximal end to minimize the potential for interference with a speculum instead of a safety sheath. In the embodiment illustrated in FIGS. 94 and 95, safety sheath 637 may also protect the distal end cutting edge 209 prior to and/or after device use, but it may also just cover the joint between cutting sheath 206 and positioning rod 204, and not need to be repositioned before and/or after ventilation tube deployment.

Figure 96:
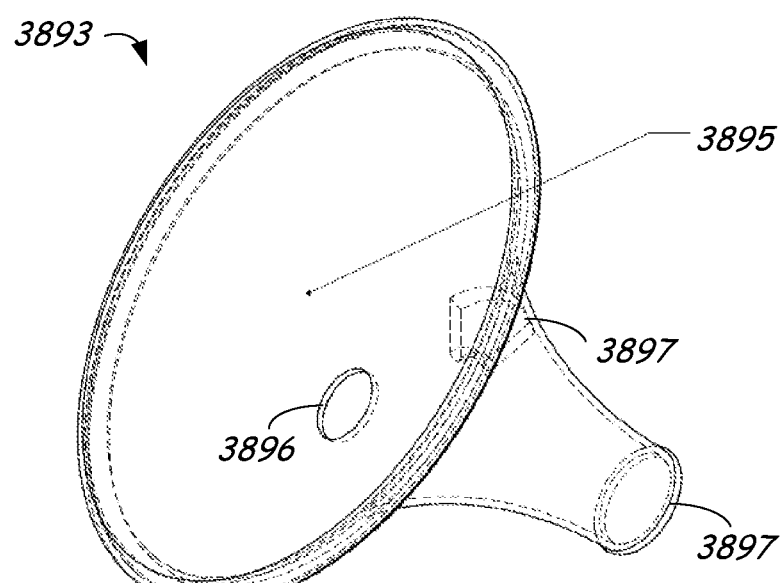
FIGS. 96-98 illustrate an embodiment of a speculum-like device with unique features for interfacing with the insertion system illustrated in FIGS. 2 and 3.
Figure 97:
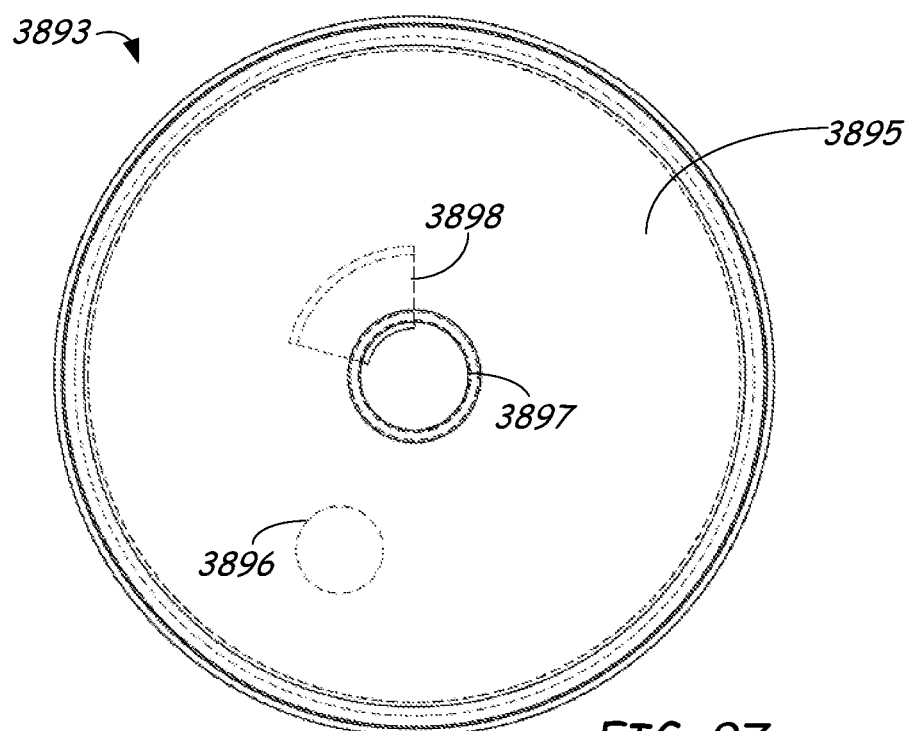
Figure 98:
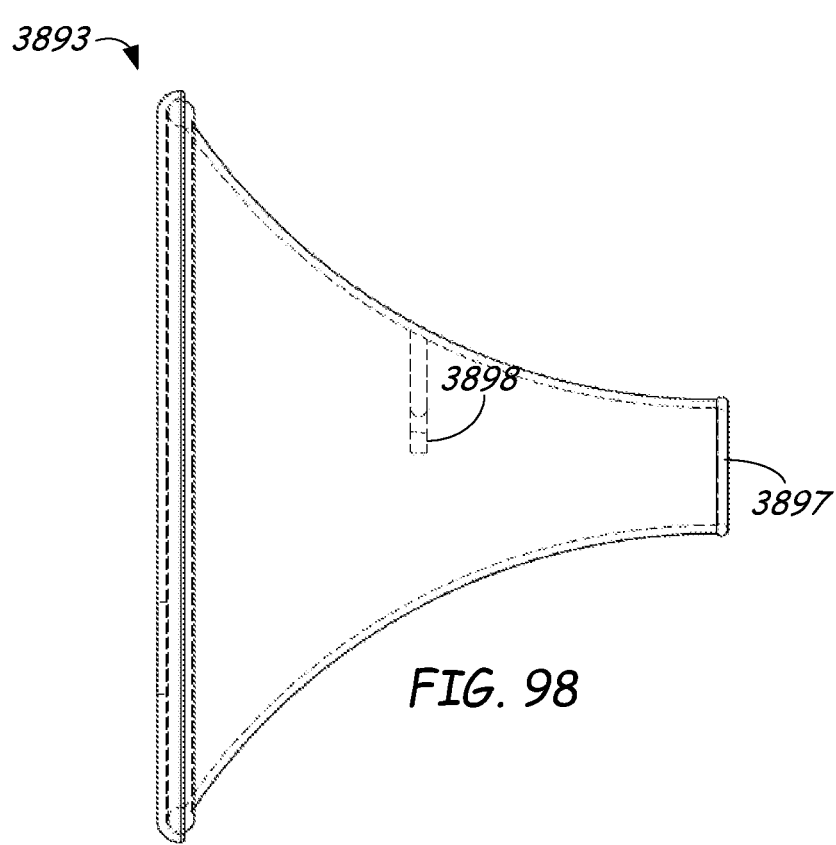

FIGS. 96-98 illustrate an embodiment of a speculum-like device 3893 with unique features for interfacing with an insertion system 200. FIG. 96 is a perspective view, FIG. 97 is a end view and FIG. 98 is a side view. FIGS. 96-98 illustrate speculum 3893 with a clear cover 3895 over the larger opening. This clear cover 3895 has an opening 3896 that is smaller than the normal speculum opening 3897 through which the insertion end 202 of insertion system 200 is passed. This smaller opening 3896 provides for a surface to rest the positioning rod 204 against to improve stability during ventilation tube insertion. Alternatively or in addition to, a brace or rest 3898 may be included on the inner surface of the speculum 3893b, on the positioning rod (not illustrated), or on both.

Speculum 3893 may also include a passage and/or a clip for passage or attachment of one or more fiber-optic scopes or similar visualization tools. While the insertion system can be used under direct visualization or under magnification, such as that provided by an operating otoscope or microscope, the use of fiber optic scopes could also be used. The ability to attach the fiber optic scope to a speculum like device allows the clinician to hold and position both devices with a single hand. These passages and attachments could also be used for passing or attaching tubes for the administration of drugs such as analgesics or antibiotics, or the passages themselves may act as a passage for drugs.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claim.

What is claimed is:

1. A ventilation tube comprising:
   a hollow main body oriented along a central axis and having an inner wall, an outer wall, a medial end and a lateral end;
   a single medial flange located at the medial end of the hollow main body and has an outer peripheral edge that comprises a curved portion and notched portion; and
   a tab having a fixed end directly coupled to the outer wall and extending from the outer wall of the hollow main body to a free end, wherein the fixed end is located between medial and lateral ends and is spaced apart from the medial end and spaced apart from the lateral end of the hollow main body; and
   wherein the notched portion of the outer peripheral edge of the medial flange is located on a same side relative to the central axis of the hollow main body as the tab.

2. The ventilation tube of claim 1, wherein the medial end is beveled such that a first axial length of the inner wall of the hollow main body is greater than an opposing second axial length of the inner wall of the hollow main body.

3. The ventilation tube of claim 1, wherein the curved portion of the outer peripheral edge of the medial flange is positioned outwardly from the medial end and a radial distance from the central axis of the hollow main body.

4. The ventilation tube of claim 1, wherein the notched portion of the outer peripheral edge of the medial flange comprises at least one straight edge.

5. A ventilation tube comprising:
   a hollow structure having a lumen that is oriented about a central axis and including an outer wall, an inner wall, a medial end, a lateral end and an axial length defined between the medial end and the lateral end, wherein the medial end is beveled such that the axial length includes a first axial length and an opposing second axial length along the wall that is greater than the first axial length;
   a medial flange located at the beveled medial end and has an outer peripheral edge that comprises a curved portion and notched portion;
   a tab having a fixed end directly coupled to the outer wall and located between and spaced apart from the medial end and the lateral end and radially extending from the outer wall of the hollow structure to a free end, wherein the free end is located a distance from the outer wall that is greater than a distance that the medial flange extends from the outer wall; and
   wherein the notched portion of the outer peripheral edge of the medial flange is located on a same side relative to the central axis of the hollow main body as the tab.

6. The ventilation tube of claim 5, wherein the tab is oriented perpendicularly from the central axis of the hollow structure.

7. The ventilation tube of claim 5, wherein the curved portion of the outer peripheral edge of the medial flange is positioned outwardly from the medial end and a radial distance from the central axis of the hollow structure.

8. The ventilation tube of claim 5, wherein the notched portion of the outer peripheral edge of the medial flange comprises at least one straight edge.

9. The ventilation tube of claim 5, wherein a location of the notched portion of the outer peripheral edge with respect to the outer wall of the hollow structure aligns with a location of the tab extending from the outer wall of the hollow structure.

10. A ventilation tube comprising:
    a hollow structure having a lumen that is oriented about a central axis and including an outer wall, an inner wall, a medial end and a lateral end;
    a medial flange located at the medial end, wherein the medial flange comprises an outer peripheral edge that comprises at least one curved portion and at least one notched portion; and
    a visualization tab having a fixed end directly coupled to the outer wall of the hollow structure and extending from the outer wall to a free end, wherein the fixed end of the visualization tab is located between and spaced apart from the medial end and the lateral end of the hollow structure.

11. The ventilation tube of claim 10, wherein a location of the at least one notched portion of the outer peripheral edge with respect to the outer wall of the hollow structure aligns with a location of the visualization tab extending from the outer wall of the hollow structure.

12. The ventilation tube of claim 10, wherein the visualization tab extends from the outer wall of the hollow structure a distance that is greater than a distance that the at least one notched portion of the medial flange extends from the medial end of the hollow structure.

* * * * *